United States Patent
Hayashi et al.

(10) Patent No.: US 11,225,605 B2
(45) Date of Patent: *Jan. 18, 2022

(54) POLYMERIZABLE LIQUID CRYSTAL COMPOUND, METHOD FOR PRODUCING POLYMERIZABLE LIQUID CRYSTAL COMPOUND, POLYMERIZABLE LIQUID CRYSTAL COMPOSITION, OPTICALLY ANISOTROPIC FILM, OPTICAL FILM, POLARIZING PLATE, AND IMAGE DISPLAY DEVICE

(71) Applicant: FUJIFILM Corporation, Tokyo (JP)

(72) Inventors: Daisuke Hayashi, Kanagawa (JP); Satoshi Shimamura, Kanagawa (JP); Keita Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 78 days.

This patent is subject to a terminal disclaimer.

(21) Appl. No.: 16/529,163

(22) Filed: Aug. 1, 2019

(65) Prior Publication Data

US 2019/0352567 A1    Nov. 21, 2019

Related U.S. Application Data

(63) Continuation of application No. PCT/JP2018/006248, filed on Feb. 21, 2018.

(30) Foreign Application Priority Data

Feb. 21, 2017 (JP) .............................. JP2017-030116

(51) Int. Cl.
*G02F 1/1333* (2006.01)
*C09K 19/34* (2006.01)
*C09K 19/04* (2006.01)

(52) U.S. Cl.
CPC ...... *C09K 19/3497* (2013.01); *C09K 19/3405* (2013.01); *C09K 2019/0448* (2013.01)

(58) Field of Classification Search
CPC ............ C09K 19/3405; C09K 19/3497; C09K 2019/0448; C09K 2019/0444; C09K 19/38; G02F 1/1333
USPC ..................................................... 252/299.61
See application file for complete search history.

(56) References Cited

U.S. PATENT DOCUMENTS

| | | | |
|---|---|---|---|
| 2010/0045901 A1 | 2/2010 | Uehira et al. | |
| 2015/0175564 A1 | 6/2015 | Sakamoto et al. | |
| 2019/0352567 A1* | 11/2019 | Hayashi | ............... C07D 339/06 |
| 2020/0140758 A1* | 5/2020 | Shimamura | ............ C09K 19/56 |
| 2020/0140759 A1* | 5/2020 | Shimamura | ........... C07C 69/753 |
| 2020/0369959 A1* | 11/2020 | Hayashi | ............... G02B 5/3016 |

FOREIGN PATENT DOCUMENTS

| | | |
|---|---|---|
| JP | 2008-273925 A | 11/2008 |
| JP | 2010-030979 A | 2/2010 |
| JP | 2010-031223 A | 2/2010 |
| JP | 2013-033248 A | 2/2013 |
| JP | 2016-047813 A | 4/2016 |
| JP | 2016-081035 A | 5/2016 |
| JP | 2016-194693 A | 11/2016 |
| WO | 2008/072794 A1 | 6/2008 |
| WO | 2014/010325 A1 | 1/2014 |

OTHER PUBLICATIONS

Office Action, issued by the Japanese Patent Office dated Jun. 2, 2020, in connection with Japanese Patent Application No. 2019-501378.
International Search Report issued in PCT/JP2018/006248 dated Apr. 17, 2018.
Written Opinion issued in PCT/JP2018/006248 dated Apr. 17, 2018.
International Preliminary Report on Patentability completed by WIPO on Aug. 27, 2019 in connection with International Patent Application No. PCT/JP2018/006248.

* cited by examiner

*Primary Examiner* — Geraldina Visconti
(74) *Attorney, Agent, or Firm* — Edwards Neils LLC; Jean C. Edwards, Esq.

(57) ABSTRACT

An object of the present invention is to provide a polymerizable liquid crystal compound having excellent solubility, which is used for the formation of an optically anisotropic film having excellent durability, a method for producing the same, a polymerizable liquid crystal composition, an optically anisotropic film, an optical film, a polarizing plate, and an image display device. The polymerizable liquid crystal compound of the embodiment of the present invention is a polymerizable liquid crystal compound represented by Formula (1), $L^1\text{-}SP^1\text{-}A^1\text{-}D^3\text{-}G^1\text{-}D^1\text{-}Ar\text{-}D^2\text{-}G^2\text{-}D^4\text{-}A^2\text{-}SP^2\text{-}L^2$ . . . (1) In Formula (1), the ClogP value of the group represented by $L^1\text{-}SP^1\text{-}A^1\text{-}D^3\text{-}G^1\text{-}D^1$ and the ClogP value of the group represented by $L^2\text{-}SP^2\text{-}A^2\text{-}D^4\text{-}G^2\text{-}D^2$ are different from each other, and at least one of the ClogP values is 3.3 or more.

20 Claims, 1 Drawing Sheet

POLYMERIZABLE LIQUID CRYSTAL COMPOUND, METHOD FOR PRODUCING POLYMERIZABLE LIQUID CRYSTAL COMPOUND, POLYMERIZABLE LIQUID CRYSTAL COMPOSITION, OPTICALLY ANISOTROPIC FILM, OPTICAL FILM, POLARIZING PLATE, AND IMAGE DISPLAY DEVICE

CROSS-REFERENCE TO RELATED APPLICATIONS

This application is a Continuation of PCT International Application No. PCT/JP2018/006248 filed on Feb. 21, 2018, which was published under PCT Article 21(2) in Japanese, and which claims priority under 35 U.S.C. § 119(a) to Japanese Patent Application No. 2017-030116 filed on Feb. 21, 2017. The above applications are hereby expressly incorporated by reference, in their entirety, into the present application.

BACKGROUND OF THE INVENTION

1. Field of the Invention

The present invention relates to a polymerizable liquid crystal compound, a method for producing a polymerizable liquid crystal compound, a polymerizable liquid crystal composition, an optically anisotropic film, an optical film, a polarizing plate, and an image display device.

2. Description of the Related Art

A polymerizable compound exhibiting reverse-wavelength dispersion properties enables, for example, conversion of accurate light ray wavelengths over a wide wavelength range and reduction in the thickness of a retardation film due to its high refractive index, and therefore, the polymerizable compound has been actively studied.

Furthermore, T-type molecular design guidelines have generally been applied to the polymerizable compound exhibiting reverse-wavelength dispersion properties, and the polymerizable compound has been required to decrease the wavelength of a long molecular axis and increase the wavelength of a short axis positioned at the center of the molecule.

In this regard, it is known that a cycloalkylene skeleton having no absorption wavelength is used for the connection between a skeleton of the short axis positioned at the center of a molecule (hereinafter also referred to as a "reverse-wavelength dispersion expressing portion") and the long axis of the molecule (see, for example, JP2008-273925A, JP2010-031223A, WO2014/010325A, and JP2016-081035A).

SUMMARY OF THE INVENTION

The present inventors have conducted studies investigations on JP2008-273925A, JP2010-031223A, WO2014/010325A, and JP2016-081035A, and have thus found that the solubility of a polymerizable compound is deteriorated in some cases, depending on the type of the polymerizable compound, and that there is a problem in durability, that is, a change in the birefringence of an optically anisotropic film thus formed in a case where the optically anisotropic film is exposed to a high temperature and a high humidity, depending on polymerization conditions such as the type of the polymerizable compound, the type of a polymerization initiator, and a curing temperature.

Therefore, the present invention has an object to provide a polymerizable liquid crystal compound having excellent solubility, which is used for the formation of an optically anisotropic film having excellent durability, a method for producing the same, a polymerizable liquid crystal composition, an optically anisotropic film, an optical film, a polarizing plate, and an image display device.

The present inventors have conducted extensive studies to achieve the object, and as a result, they have found that in a case of using a polymerizable liquid crystal compound having an asymmetric structure, in which an aromatic ring constituting a reverse-wavelength dispersion expressing portion has a sterically hindered group, the structures of two groups extending in the long-axis direction from a center at the reverse-wavelength dispersion expressing portion are different from each other, and at least one of the groups is hydrophobic, the solubility becomes good and the durability of an optically anisotropic film thus formed is also improved, thereby completing the present invention.

That is, the present inventors have found that the object can be accomplished by the following configurations.

[1] A polymerizable liquid crystal compound represented by Formula (1),

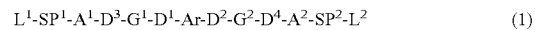

$$L^1\text{-}SP^1\text{-}A^1\text{-}D^3\text{-}G^1\text{-}D^1\text{-}Ar\text{-}D^2\text{-}G^2\text{-}D^4\text{-}A^2\text{-}SP^2\text{-}L^2 \quad (1)$$

in Formula (1), the C log P value of the group represented by $L^1$-$SP^1$-$A^1$-$D^3$-$G^1$-$D^1$ and the C log P value of the group represented by $L^2$-$SP^2$-$A^2$-$D^4$-$G^2$-$D^2$ are different from each other, and at least one of the C log P values is 3.3 or more.

[2] The polymerizable liquid crystal compound as described in [1], in which in Formula (1), the C log P value of the group represented by $L^2$-$SP^2$-$A^2$-$D^4$-$G^2$-$D^2$ is higher than the C log P value of the group represented by $L^1$-$SP^1$-$A^1$-$D^3$-$G^1$-$D^1$.

[3] The polymerizable liquid crystal compound as described in [1] or [2], in which in Formulae (Ar-1) to (Ar-8), $Z^1$ represents a monovalent aliphatic hydrocarbon group having 3 to 20 carbon atoms.

[4] A method for producing a polymerizable liquid crystal compound, used to synthesize the polymerizable liquid crystal compound as described in [1], comprising:

a first esterification step of reacting a compound represented by Formula (2) with a compound represented by Formula (3) to produce a phenol compound; and a second esterification step of reacting the phenol compound obtained in the first esterification step with a compound represented by Formula (4) to obtain the polymerizable liquid crystal compound as described in [1],

$$\text{HO—Ar—OH} \quad (2)$$

$$L^1\text{-}SP^1\text{-}A^1\text{-}D^3\text{-}G^1\text{-}COOH \quad (3)$$

$$L^2\text{-}SP^2\text{-}A^2\text{-}D^4\text{-}G^2\text{-}COOH \quad (4).$$

[5] A polymerizable liquid crystal composition comprising:

the polymerizable liquid crystal compound as described in any one of [1] to [3].

[6] The polymerizable liquid crystal composition as described in [5], further comprising:

a polymerizable compound having two or more polymerizable groups, which is different from the polymerizable liquid crystal compound.

[7] An optically anisotropic film obtained by polymerization of the polymerizable liquid crystal composition as described in [5] or [6].

[8] An optical film comprising:
the optically anisotropic film as described in [7].

[9] A polarizing plate comprising:
the optical film as described in [8]; and
a polarizer.

[10] An image display device comprising:
the optical film as described in [8] or the polarizing plate as described in [9].

According to the present invention, it is possible to provide a polymerizable liquid crystal compound having excellent solubility, which is used for the formation of an optically anisotropic film having excellent durability, a method for producing the same, a polymerizable liquid crystal composition, an optically anisotropic film, an optical film, a polarizing plate, and an image display device.

DESCRIPTION OF THE PREFERRED EMBODIMENTS

Figure 1A:
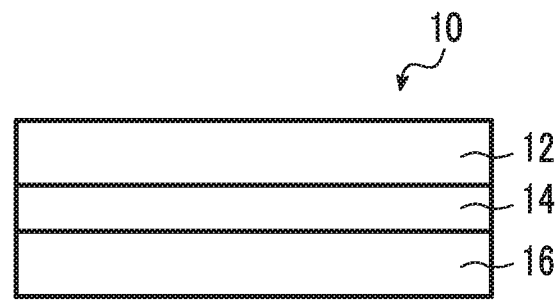
FIG. 1A is a schematic cross-sectional view showing an example of an optical film of an embodiment of the present invention.

Hereinafter, the present invention will be described in detail.

The following description of the constitutional requirements is made based on representative embodiments of the present invention in some cases, but it should not be construed that the present invention is limited to such embodiments.

Furthermore, in the present specification, a numerical range expressed using "to" means a range that includes the preceding and succeeding numerical values of "to" as the lower limit value and the upper limit value, respectively.

In the present specification, the bonding direction of a divalent group (for example, —O—CO—) expressed is not particularly limited, and for example, in a case where $D^1$ in Formula (1) which will be described later is —O—CO—, $D^1$ may be either *1-O—CO—*2 or *1-CO—O—*2, in which *1 represents a bonding position with the Ar side and *2 represents a bonding position with the $G^1$ side.

[Polymerizable Liquid Crystal Compound]

The polymerizable liquid crystal compound of an embodiment of the present invention is a compound represented by Formula (1).

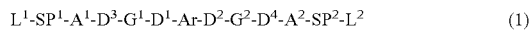  (1)

Furthermore, in the polymerizable liquid crystal compound of the embodiment of the present invention, the C log P value of a group represented by $L^1$-$SP^1$-$A^1$-$D^3$-$G^1$-$D^1$ (hereinafter also simply referred to as a "X group") in Formula (1) and the C log P value of a group represented by $L^2$-$SP^2$-$A^2$-$D^4$-$G^2$-$D^2$ (hereinafter also simply referred to as a "Y group") are different from each other, and at least one of the C log P values is 3.3 or more.

Here, the C log P value is a value determined by calculation of a common logarithm log P of a partition coefficient P between 1-octanol and water. With regard to a method or software used for the calculation of the C log P value, well-known methods or software can be used, but in the present invention, a C log P program combined into ChemBioDraw Ultra 13.0 from Cambridge Soft is used unless otherwise specified.

In addition, the expression that the C log P values of the X group and the Y group are different from each other is intended to denote that the structures of the X group and the Y group are different from each other and the structures of two groups extending in the long-axis direction from a center at the aromatic ring constituting the reverse-wavelength dispersion expressing portion, that is, Ar in Formula (1), in the polymerizable liquid crystal compound are different from each other in the polymerizable liquid crystal compound represented by Formula (1). Further, in a case where the structures of the X group and the Y group are the same structures or structural isomers, the C log P values of the X group and the Y group represent the same values.

In the present invention, in Formula (1), Ar has a sterically hindered group ($Z^1$ in Formulae (Ar-1) to (Ar-8) which will be described later), the structures of the X group and the Y group in Formula (1) are different from each other, and in a case of using the polymerizable liquid crystal compound having a C log P value of at least one of the groups of 3.3 or more, the solubility is improved, and the durability of an optically anisotropic film thus formed becomes good, as described above.

A reason therefor is not specifically clear, but is presumed to be as follows by the present inventors.

That is, it is presumed that by incorporating a sterically hindered group into the aromatic ring constituting the reverse-wavelength dispersion expressing portion, the melting point of the polymerizable liquid crystal compound is lowered, and further, by making the polymerizable liquid crystal compound into an asymmetric structure, the packing among the molecules is inhibited, and as a result, the solubility of the polymerizable liquid crystal compound in an organic solvent is improved.

In addition, it is presumed that due to the presence of the sterically hindered group incorporated into the aromatic ring constituting the reverse-wavelength dispersion expressing portion, water can be inhibited from approaching a central part of the polymerizable liquid crystal compound, and by setting at least one of the two groups extending in the long-axis direction from a center at the aromatic ring constituting the reverse-wavelength dispersion expressing portion to be hydrophobic, moisture absorption of an optically anisotropic film thus formed is decreased, and as a result, the durability of the optically anisotropic film is improved. Hereinafter, with regard to the polymerizable liquid crystal compound of the embodiment of the present invention, the structure of Formula (1) will be described in detail.

The polymerizable liquid crystal compound of the embodiment of the present invention is a polymerizable liquid crystal compound represented by Formula (1), as described above.

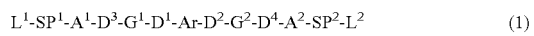  (1)

In Formula (1), $D^1$, $D^2$, $D^3$, and $D^4$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—NR$^1$—. $R^1$, $R^2$, $R^3$, and $R^4$ each independently represent a hydrogen atom, a fluorine atom, or an alkyl group having 1 to 4 carbon atoms.

Incidentally, in Formula (1), $G^1$ and $G^2$ each independently represent a divalent alicyclic hydrocarbon group having 5 to 8 carbon atoms, which may have a substituent, and one or more of —CH$_2$-'s constituting the alicyclic hydrocarbon group may be substituted with —O—, —S—, or —NH—.

Furthermore, in Formula (1), $A^1$ and $A^2$ each independently represent an aromatic ring having 6 or more carbon atoms, which may have a substituent, or a cycloalkane ring having 6 or more carbon atoms, which may have a substituent.

Moreover, in Formula (1), $SP^1$ and $SP^2$ each independently represent a single bond, a linear or branched alkylene group having 1 to 12 carbon atoms, or a divalent linking group in which one or more of —CH$_2$-'s constituting the linear or branched alkylene group having 1 to 12 carbon atoms are substituted with —O—, —S—, —NH—, —N(Q)-, or —CO—, and Q represents a substituent.

In addition, in Formula (1), $L^1$ and $L^2$ each independently represent a monovalent organic group, and at least one of $L^1$ or $L^2$ represents a polymerizable group, provided that in a case where Ar is an aromatic ring represented by Formula (Ar-4), at least one of $L^1$, $L^2$, or $L^3$ or $L^4$ in Formula (Ar-4) represents a polymerizable group.

In Formula (1), the divalent alicyclic hydrocarbon group having 5 to 8 carbon atoms represented by each of $G^1$ and $G^2$ is preferably a 5- or 6-membered ring. Further, the alicyclic hydrocarbon group may be saturated or unsaturated, but is preferably a saturated alicyclic hydrocarbon group. With respect to the divalent alicyclic hydrocarbon group represented by each of $G^1$ and $G^2$, reference can be made to, for example, the description in paragraph 0078 of JP2012-021068A, the contents of which are incorporated herein by reference.

In addition, examples of the substituent which may be contained in the divalent alicyclic hydrocarbon group having 5 to 8 carbon atoms include the same ones as the substituents which may be contained in $Y^1$ in Formula (Ar-1) which will be described later.

In Formula (1), examples of the aromatic ring having 6 or more carbon atoms represented by each of $A^1$ and $A^2$ include aromatic hydrocarbon rings such as a benzene ring, a naphthalene ring, an anthracene ring, and a phenanthroline ring; and aromatic heterocyclic rings such as a furan ring, a pyrrole ring, a thiophene ring, a pyridine ring, a thiazole ring, and a benzothiazole ring. Among those, the benzene ring (for example, a 1,4-phenyl group) is preferable.

Furthermore, in Formula (1), examples of the cycloalkane ring having 6 or more carbon atoms represented by each of $A^1$ and $A^2$ include a cyclohexane ring, a cycloheptane ring, a cyclooctane ring, a cyclododecane ring, and a cyclodocosane ring. Among those, the cyclohexane ring (for example, a 1,4-cyclohexylene group) is preferable, and a trans-1,4-cyclohexylene group is more preferable.

In addition, examples of the aromatic ring having 6 or more carbon atoms or the substituent which may be contained in the cycloalkane ring having 6 or more carbon atoms include the same ones as the substituents which may be contained in $Y^1$ in Formula (Ar-1) which will be described later.

In Formula (1), suitable examples of the linear or branched alkylene group having 1 to 12 carbon atoms represented by each of $SP^1$ and $SP^2$ include a methylene group, an ethylene group, a propylene group, and a butylene group.

Furthermore, in $SP^1$ and $SP^2$, one or more of —CH$_2$-'s constituting the alkylene group as described above may be a divalent linking group substituted with —O—, —S—, —NH—, —N(Q)-, or —CO—, and examples of the substituent represented by Q include the same ones as the substituent which may be contained in $Y^1$ in Formula (Ar-1) which will be described later.

In Formula (1), the polymerizable group represented by at least one of $L^1$ or $L^2$ is not particularly limited, but is preferably a polymerizable group capable of radical polymerization or cationic polymerization.

A generally known radically polymerizable group can be used as the radically polymerizable group, and suitable examples thereof include an acryloyl group and a methacryloyl group. In this case, it is generally known that the acryloyl group exhibits a fast polymerization rate, and thus, the acryloyl group is preferable from the viewpoint of improvement of productivity, but the methacryloyl group can also be used as the polymerizable group of a highly birefringent liquid crystal.

A generally known cationically polymerizable group can be used as the cationically polymerizable group, and specific examples thereof include an alicyclic ether group, a cyclic acetal group, a cyclic lactone group, a cyclic thioether group, a spiroorthoester group, and a vinyloxy group. Among those, the alicyclic ether group or the vinyloxy group is preferable, and the epoxy group, the oxetanyl group, or the vinyloxy group is particularly preferable.

Particularly preferred examples of the polymerizable groups include the following ones.

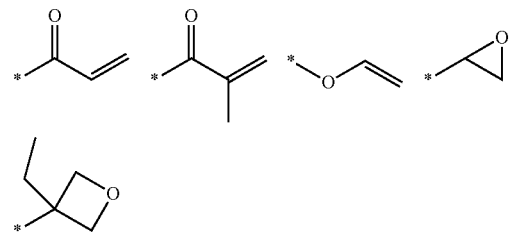

On the other hand, in Formula (1), Ar represents any one aromatic ring selected from the group consisting of groups represented by Formulae (Ar-1) to (Ar-8). Further, in Formulae (Ar-1) to (Ar-8), *1 represents a bonding position with $D^1$ and *2 represents a bonding position with $D^2$.

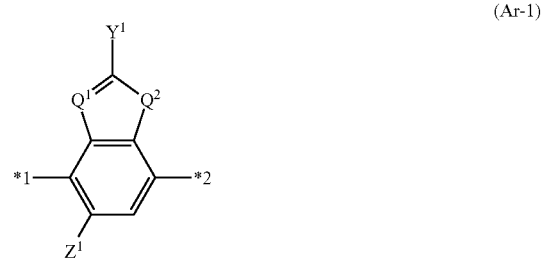

(Ar-1)

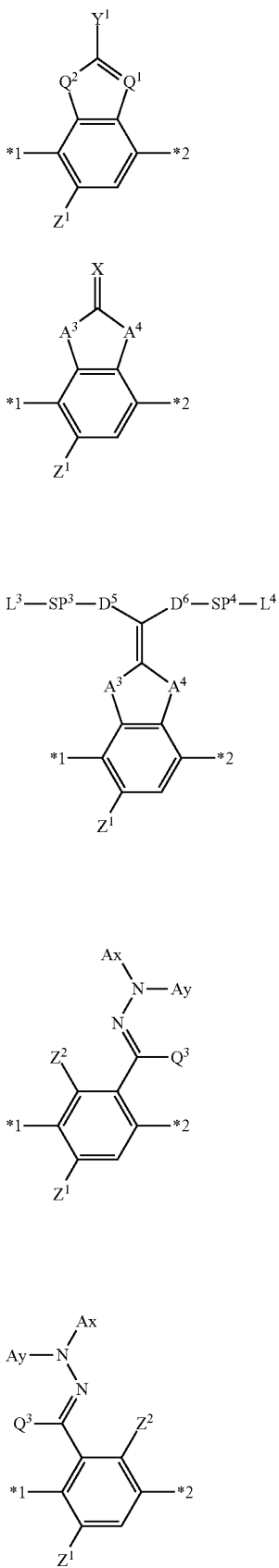

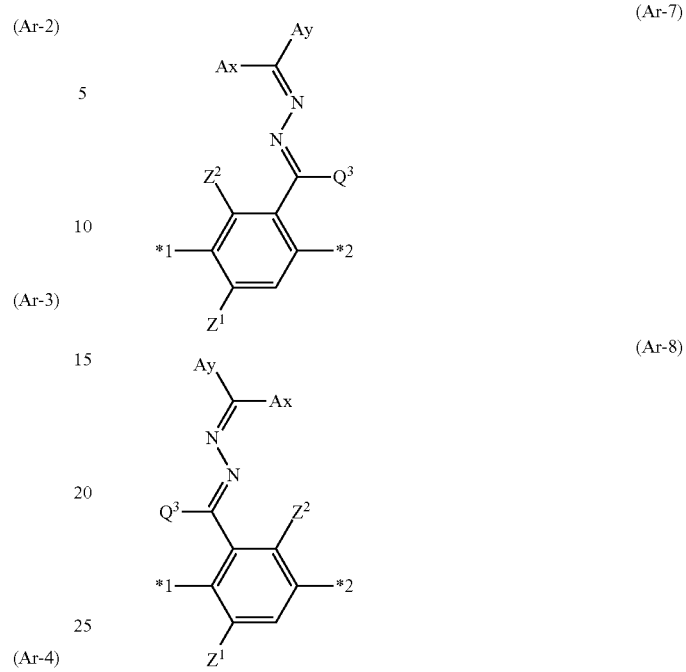

Here, in Formulae (Ar-1) and (Ar-2), $Q^1$ represents N or CH, $Q^2$ represents —S—, —O—, or —N($R^5$)—, $R^5$ represents a hydrogen atom or an alkyl group having 1 to 6 carbon atoms, and $Y^1$ represents an aromatic hydrocarbon group having 6 to 12 carbon atoms or an aromatic heterocyclic group having 3 to 12 carbon atoms, each of which may have a substituent. Specific examples of the alkyl group having 1 to 6 carbon atoms represented by $R^5$ include a methyl group, an ethyl group, a propyl group, an isopropyl group, an n-butyl group, an isobutyl group, a sec-butyl group, a tert-butyl group, an n-pentyl group, and an n-hexyl group.

Examples of the aromatic hydrocarbon group having 6 to 12 carbon atoms represented by $Y^1$ include aryl groups such as a phenyl group, a 2,6-diethylphenyl group, and a naphthyl group.

Examples of the aromatic heterocyclic group having 3 to 12 carbon atoms represented by $Y^1$ include heteroaryl groups such as a thienyl group, a thiazolyl group, a furyl group, and a pyridyl group.

Furthermore, examples of the substituent which may be contained in $Y^1$ include an alkyl group, an alkoxy group, and a halogen atom.

As the alkyl group, for example, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a tert-butyl group, and a cyclohexyl group) is more preferable, an alkyl group having 1 to 4 carbon atoms is still more preferable, and the methyl group or the ethyl group is particularly preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, and a methoxy ethoxy group) is more preferable, an alkoxy group having 1 to 4 carbon atoms is still more preferable, and the methoxy group or the ethoxy group is particularly preferable.

Examples of the halogen atom include a fluorine atom, a chlorine atom, a bromine atom, and an iodine atom, and among those, the fluorine atom or the chlorine atom is preferable.

In addition, in Formulae (Ar-1) to (Ar-8), $Z^1$ is a group representing the above-mentioned sterically hindered group, and represents a monovalent aliphatic hydrocarbon group having 3 to 20 carbon atoms, a monovalent aromatic hydrocarbon group having 6 to 20 carbon atoms, a halogen atom, —$OR^6$, —$NR^7R^8$, or —$SR^9$, and $R^6$ to $R^9$ each independently represent a monovalent aliphatic hydrocarbon group having 3 to 20 carbon atoms or a monovalent aromatic hydrocarbon group having 6 to 20 carbon atoms.

As the monovalent aliphatic hydrocarbon group having 3 to 20 carbon atoms represented by $Z^1$, an alkyl group having 3 to 15 carbon atoms is preferable, an alkyl group having 3 to 8 carbon atoms is more preferable, and specifically, an isopropyl group, a tert-pentyl group (1,1-dimethylpropyl group), a tert-butyl group, or a 1,1-dimethyl-3,3-dimethyl-butyl group is still more preferable, and a tert-butyl group is particularly preferable.

Specific examples of the monovalent aromatic hydrocarbon group having 6 to 20 carbon atoms represented by $Z^1$ include a phenyl group, a 2,6-diethylphenyl group, a naphthyl group, and a biphenyl group, and an aryl group having 6 to 12 carbon atoms (particularly a phenyl group) is preferable.

Examples of the halogen atom represented by $Z^1$ include a fluorine atom, a chlorine atom, a bromine atom, and an iodine atom, and among those, the fluorine atom, the chlorine atom, or the bromine atom is preferable.

On the other hand, as the monovalent aliphatic hydrocarbon group having 3 to 20 carbon atoms represented by each of $R^6$ to $R^9$, an alkyl group having 3 to 15 carbon atoms is preferable, an alkyl group having 3 to 8 carbon atoms is more preferable, and specifically, an isopropyl group, a tert-pentyl group (1,1-dimethylpropyl group), a tert-butyl group, or a 1,1-dimethyl-3,3-dimethyl-butyl group is more preferable, and a tert-butyl group is particularly preferable.

Furthermore, specific examples of the monovalent aromatic hydrocarbon group having 6 to 20 carbon atoms represented by each of $R^6$ to $R^9$ include a phenyl group, a 2,6-diethylphenyl group, a naphthyl group, and a biphenyl group, and the aryl group having 6 to 12 carbon atoms (particularly a phenyl group) is preferable.

In addition, in Formulae (Ar-5) to (Ar-8), $Z^2$ represents a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$OR^{10}$, —$NR^{11}R^{12}$, or —$SR^{13}$, and $R^{10}$ to $R^{13}$ each independently represent a hydrogen atom or an alkyl group having 1 to 6 carbon atoms.

As the monovalent aliphatic hydrocarbon group having 1 to 20 carbon atoms represented by $Z^2$, an alkyl group having 1 to 15 carbon atoms is preferable and an alkyl group having 1 to 8 carbon atoms is more preferable. Specifically, a methyl group, an ethyl group, an isopropyl group, a tert-pentyl group (1,1-dimethylpropyl group), a tert-butyl group, or a 1,1-dimethyl-3,3-dimethyl-butyl group is still more preferable, and the methyl group, the ethyl group, or the tert-butyl group is particularly preferable.

Examples of the monovalent alicyclic hydrocarbon group having 3 to 20 carbon atoms represented by $Z^2$ include monocyclic saturated hydrocarbon groups such as a cyclopropyl group, a cyclobutyl group, a cyclopentyl group, a cyclohexyl group, a cycloheptyl group, a cyclooctyl group, a cyclodecyl group, a methylcyclohexyl group, and an ethylcyclohexyl group; monocyclic unsaturated hydrocarbon groups such as a cyclobutenyl group, a cyclopentenyl group, a cyclodecenyl group, a cycloheptenyl group, a cyclooctenyl group, a cyclodecenyl group, a cyclopentadienyl group, a cyclohexadienyl group, a cyclooctadienyl group, and cyclodecadiene; and polycyclic saturated hydrocarbon groups such as a bicyclo[2.2.1]heptyl group, a bicyclo[2.2.2]octyl group, a tricyclo[5.2.1.0$^{2,6}$]decyl group, a tricyclo[3.3.1.1$^{3,7}$]decyl group, a tetracyclo[6.2.1.1$^{3,6}$.0$^{2,7}$] dodecyl group, and an adamantyl group.

Specific examples of the monovalent aromatic hydrocarbon group having 6 to 20 carbon atoms represented by $Z^2$ include a phenyl group, a 2,6-diethylphenyl group, a naphthyl group, and a biphenyl group, and an aryl group having 6 to 12 carbon atoms (particularly a phenyl group) is preferable.

Examples of the halogen atom represented by $Z^2$ include a fluorine atom, a chlorine atom, a bromine atom, and an iodine atom, and among those, the fluorine atom, the chlorine atom, or the bromine atom is preferable.

On the other hand, specific examples of the alkyl group having 1 to 6 carbon atoms represented by each of $R^{10}$ and $R^{13}$ include a methyl group, an ethyl group, a propyl group, an isopropyl group, an n-butyl group, an isobutyl group, a sec-butyl group, a tert-butyl group, and an n-pentyl group and an n-hexyl group.

In addition, in Formulae (Ar-3) and (Ar-4), $A^3$ and $A^4$ each independently represent a group selected from the group consisting of —O—, —N($R^{14}$)—, —S—, and —CO—, and $R^{14}$ represents a hydrogen atom or a substituent.

Examples of the substituent represented by $R^{14}$ include the same substituents which may be contained in $Y^1$ in Formula (Ar-1).

Furthermore, in Formula (Ar-3), X represents a non-metal atom of Groups 14 to 16 to which a hydrogen atom or a substituent may be bonded.

Moreover, examples of the non-metal atom of Groups 14 to 16 represented by X include an oxygen atom, a sulfur atom, a nitrogen atom having a substituent, and a carbon atom having a substituent, and specific examples of the substituent include an alkyl group, an alkoxy group, an alkyl-substituted alkoxy group, a cyclic alkyl group, an aryl group (for example, a phenyl group and a naphthyl group), a cyano group, an amino group, a nitro group, an alkylcarbonyl group, a sulfo group, and a hydroxyl group.

Furthermore, in Formula (Ar-4), $D^5$ and $D^6$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—. $R^1$, $R^2$, $R^3$, and $R^4$ each independently represent a hydrogen atom, a fluorine atom, or an alkyl group having 1 to 4 carbon atoms.

Moreover, in Formula (Ar-4), $SP^3$ and $SP^4$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent. Examples of the substituent include the same ones as those for the substituent which may be contained in $Y^1$ in Formula (Ar-1).

Furthermore, in Formula (Ar-4), $L^3$ and $L^4$ each independently represent a monovalent organic group, and at least one of $L^3$, $L^4$, or $L^1$ or $L^2$ in Formula (1) represents a polymerizable group.

Moreover, in Formulae (Ar-5) to (Ar-8), Ax represents an organic group having 2 to 30 carbon atoms, which has at least one aromatic ring selected from the group consisting of an aromatic hydrocarbon ring and an aromatic heterocyclic ring.

Furthermore, in Formulae (Ar-5) to (Ar-8), Ay represents a hydrogen atom, an alkyl group having 1 to 12 carbon atoms which may have a substituent, or an organic group having 2 to 30 carbon atoms, which has at least one aromatic ring selected from the group consisting of an aromatic hydrocarbon ring and an aromatic heterocyclic ring.

Here, the aromatic rings in Ax and Ay may have a substituent, and Ax and Ay may be bonded to each other to form a ring.

In addition, $Q^3$ represents a hydrogen atom or an alkyl group having 1 to 6 carbon atoms which may have a substituent.

Examples of Ax and Ay include ones described in paragraphs [0039] to [0095] of WO2014/010325A.

Incidentally, specific examples of the alkyl group having 1 to 6 carbon atoms represented by $Q^3$ include a methyl group, an ethyl group, a propyl group, an isopropyl group, an n-butyl group, an isobutyl group, a sec-butyl group, a tert-butyl group, an n-pentyl group, and an n-hexyl group. Examples of the substituent include the same ones as the substituents which may be contained in $Y^1$ in Formula (Ar-1).

Examples of the polymerizable liquid crystal compound represented by Formula (1) include compounds represented by Formulae (I) to (IV), and specifically the compounds represented by Formulae (I) to (IV), in which $OR^1$ (X group) and $OR^2$ (Y group) have a group shown in Tables 1 to 4.

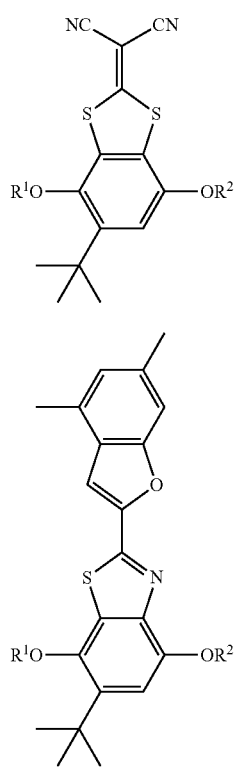

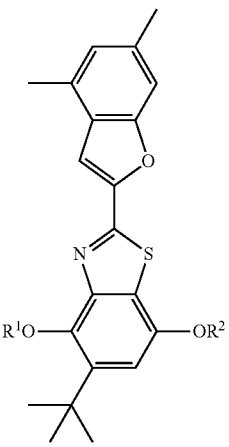

TABLE 1

| X group | |
|---|---|
| $OR^1 =$ | ClogP value |
| [structure] | 3.156 |

TABLE 1-continued

| Structure | Value |
|---|---|
| [cyclohexane-1,4-dicarboxylate-phenyl-ethyl-succinate-ethyl acrylate] | 2.847 |
| [cyclohexane-1,4-dicarboxylate-phenyl-O-(CH2)5-O-acrylate] | 4.057 |
| [benzoate-O-(CH2)4-O-acrylate] | 2.075 |
| [cyclohexane-1,4-dicarboxylate-(CH2)4-O-acrylate] | 1.611 |
| [bicyclohexyl-4,4'-dicarboxylate-(CH2)4-O-acrylate] | 4.164 |
| [cyclohexane-1,4-dicarboxylate-phenyl-ethyl-succinate-neopentyl-acrylate] | 3.156 |
| [cyclohexane-1,4-dicarboxylate-phenyl-ethyl-succinate-ethyl acrylate] | 2.847 |
| [cyclohexane-1,4-dicarboxylate-phenyl-O-(CH2)5-O-acrylate] | 4.057 |
| [benzoate-O-(CH2)4-O-acrylate] | 2.075 |
| [cyclohexane-1,4-dicarboxylate-(CH2)4-O-acrylate] | 1.611 |

TABLE 1-continued

| OR² = | ClogP value |
|---|---|
| (bicyclohexyl dicarboxylate with butanediyl acrylate) | 4.164 |

Y group

| OR² = | ClogP value |
|---|---|
| (cyclohexyl-cyclohexyl-Et ester) | 5.189 |
| (cyclohexyl-cyclohexyl-Et ester) | 5.189 |
| (cyclohexyl-cyclohexyl-Et ester) | 5.189 |
| (cyclohexyl-cyclohexyl-Et ester) | 5.189 |
| (cyclohexyl-cyclohexyl-Et ester) | 5.189 |
| (cyclohexyl-cyclohexyl-Et ester) | 5.189 |
| (cyclohexyl-propyl ester) | 3.697 |
| (cyclohexyl-propyl ester) | 3.697 |
| (cyclohexyl-propyl ester) | 3.697 |

TABLE 1-continued
| | |
|---|---|
| 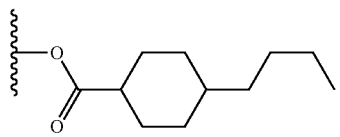 [SMILES: *OC(=O)C1CCC(CCCC)CC1] | 3.697 |
| 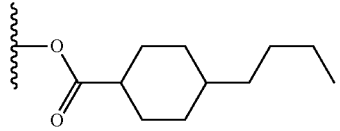 [SMILES: *OC(=O)C1CCC(CCCC)CC1] | 3.697 |
| 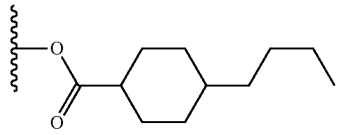 | 3.697 |
TABLE 2
X group
| OR¹ = | ClogP value |
|---|---|
| 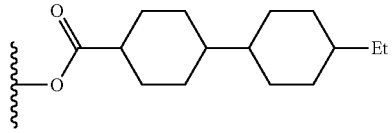 | 5.189 |
| 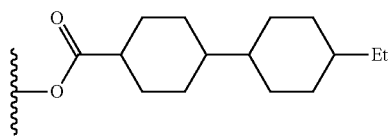 [SMILES: *OC(=O)C1CCC(C2CCC(CC)CC2)CC1] | 5.189 |
| 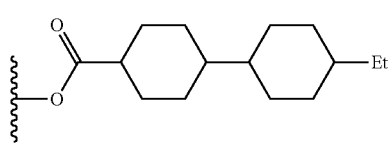 [SMILES: *OC(=O)C1CCC(C2CCC(CC)CC2)CC1] | 5.189 |
| 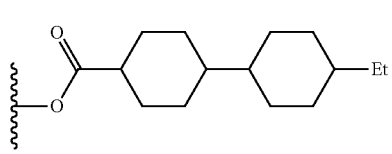 [SMILES: *OC(=O)C1CCC(C2CCC(CC)CC2)CC1] | 5.189 |
| 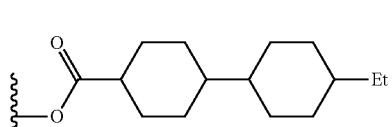 | 5.189 |
| 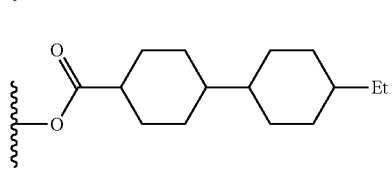 | 5.189 |

TABLE 2-continued
| | ClogP value |
|---|---|
| 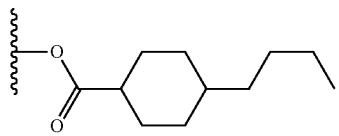 [SMILES: *OC(=O)C1CCC(CCCC)CC1] | 3.697 |
| 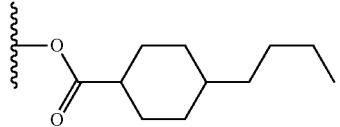 [SMILES: *OC(=O)C1CCC(CCCC)CC1] | 3.697 |
| 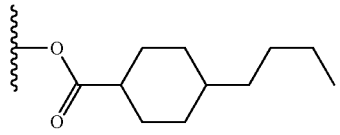 [SMILES: *OC(=O)C1CCC(CCCC)CC1] | 3.697 |
| 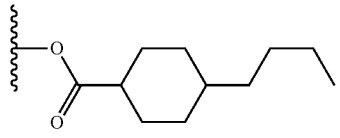 [SMILES: *OC(=O)C1CCC(CCCC)CC1] | 3.697 |
| Y group | |
|---|---|
| $OR^2 =$ | ClogP value |
| 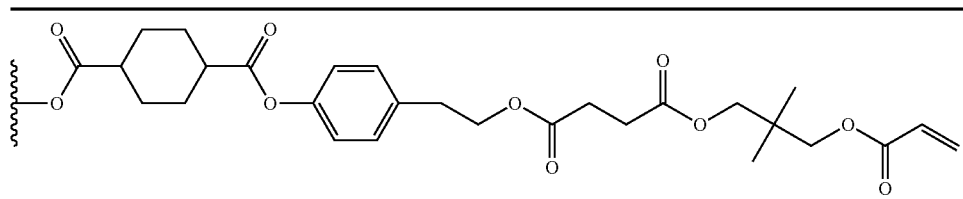 | 3.156 |
| 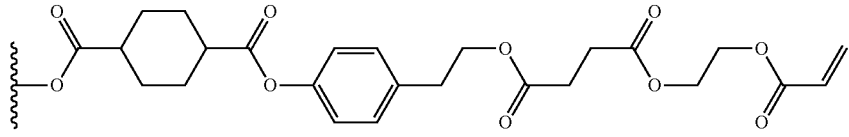 [SMILES: *OC(=O)C1CCC(C(=O)Oc2ccc(CCOC(=O)CCC(=O)OCCOC(=O)C=C)cc2)CC1] | 2.847 |
| 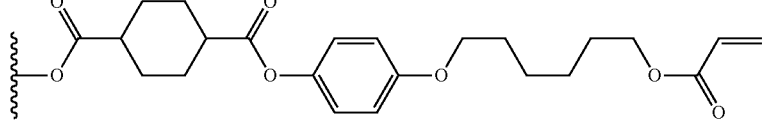 | 4.057 |
| 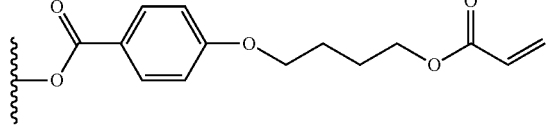 | 2.075 |
| 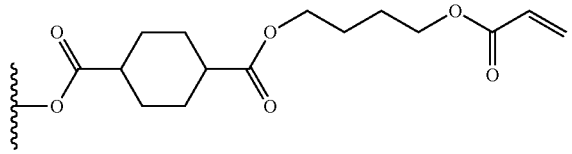 [SMILES: *OC(=O)C1CCC(C(=O)OCCCCOC(=O)C=C)CC1] | 1.611 |
| 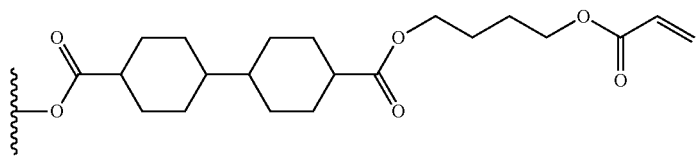 [SMILES: *OC(=O)C1CCC(C2CCC(C(=O)OCCCCOC(=O)C=C)CC2)CC1] | 4.164 |

TABLE 2-continued

| Structure | Value |
|---|---|
| (structure) | 3.156 |
| (structure) | 2.847 |
| (structure) | 4.057 |
| (structure) | 2.075 |

TABLE 3

| X group | |
|---|---|
| OR$^1$ = | ClogP value |
| (structure) | 3.697 |
| (structure) | 3.697 |
| (structure) | 4.057 |
| (structure) | 4.164 |
| (structure) | 4.057 |

TABLE 3-continued

| OR² = | ClogP value |
|---|---|
| [structure: cyclohexyl-cyclohexyl with ester linkages and butyl acrylate] | 4.164 |
| [structure: cyclohexyl with ester linkages and butyl acrylate] | 1.611 |
| [structure: cyclohexyl with ester linkages and butyl acrylate] | 1.611 |
| [structure: phenyl with ester and ether linkages and butyl acrylate] | 2.075 |
| [structure: phenyl with ester and ether linkages and butyl acrylate] | 2.075 |

| Y group | |
|---|---|
| OR² = | ClogP value |
| [structure: cyclohexyl with ester linkages and butyl acrylate] | 1.611 |
| [structure: cyclohexyl-cyclohexyl with ester linkages and butyl acrylate] | 4.164 |
| [structure: cyclohexyl with ester linkages and butyl acrylate] | 1.611 |
| [structure: cyclohexyl with ester linkages and butyl acrylate] | 1.611 |

TABLE 3-continued

| OR¹ = (structure) | ClogP value |
|---|---|
| [structure: benzoate-O-(CH₂)₄-O-acrylate] | 2.075 |
| [structure: benzoate-O-(CH₂)₄-O-acrylate] | 2.075 |
| [structure: bis-cyclohexyl dicarboxylate-phenylene-O-(CH₂)₅-O-acrylate] | 4.057 |
| [structure: bicyclohexyl dicarboxylate-(CH₂)₄-O-acrylate] | 4.164 |
| [structure: bis-cyclohexyl dicarboxylate-phenylene-O-(CH₂)₅-O-acrylate] | 4.057 |
| [structure: bicyclohexyl dicarboxylate-(CH₂)₄-O-acrylate] | 4.164 |

TABLE 4

X group

| OR¹ = | ClogP value |
|---|---|
| [structure with succinate and neopentyl-acrylate group] | 3.156 |
| [structure with succinate and ethyl-acrylate group] | 2.847 |
| [structure: cyclohexyl-cyclohexyl-phenylene-O-(CH₂)₅-O-acrylate] | 4.057 |

TABLE 4-continued
| | |
|---|---|
| 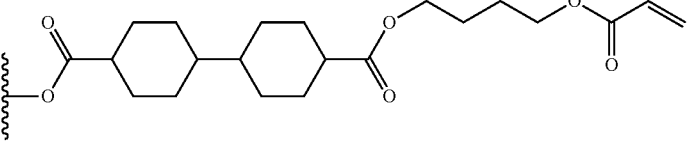 | 4.164 |
| 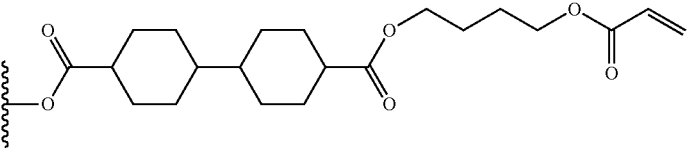 [SMILES: *OC(=O)C1CCC(C2CCC(C(=O)OCCCCOC(=O)C=C)CC2)CC1] | 4.164 |
| 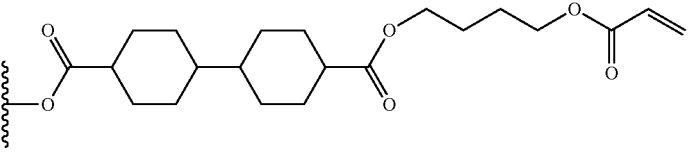 [SMILES: *OC(=O)C1CCC(C2CCC(C(=O)OCCCCOC(=O)C=C)CC2)CC1] | 4.164 |
| 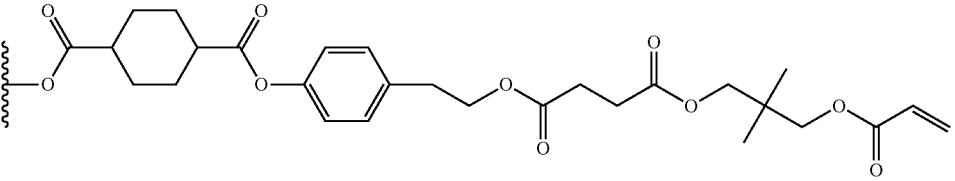 [SMILES: *OC(=O)C1CCC(C(=O)Oc2ccc(CCOC(=O)CCC(=O)OCC(C)(C)COC(=O)C=C)cc2)CC1] | 3.156 |
| 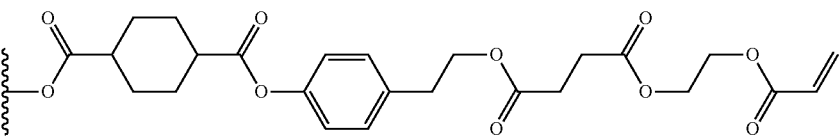 [SMILES: *OC(=O)C1CCC(C(=O)Oc2ccc(CCOC(=O)CCC(=O)OCCOC(=O)C=C)cc2)CC1] | 2.847 |
| 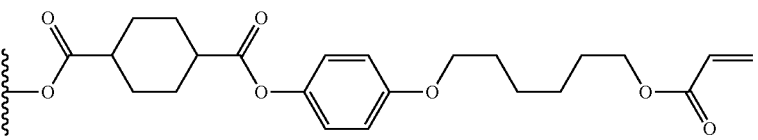 [SMILES: *OC(=O)C1CCC(C(=O)Oc2ccc(OCCCCCCOC(=O)C=C)cc2)CC1] | 4.057 |
| 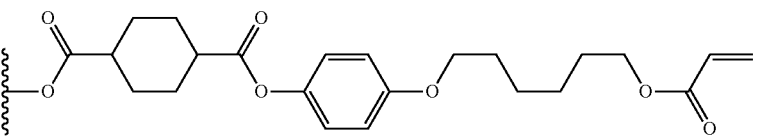 | 4.057 |
| 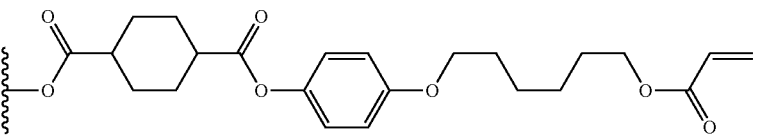 [SMILES: *OC(=O)C1CCC(C(=O)Oc2ccc(OCCCCCCOC(=O)C=C)cc2)CC1] | 4.057 |
| 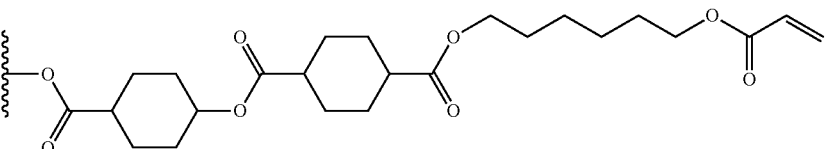 | 3.559 |
| 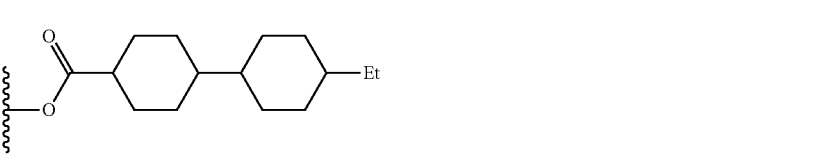 [SMILES: *OC(=O)C1CCC(C2CCC(CC)CC2)CC1] | 5.189 |

TABLE 4-continued

| OR² = | ClogP value |
|---|---|
| (structure with cyclohexane-COO-cyclohexane-COO-(CH₂)₆-O-acrylate) | 3.559 |

Y group

| OR² = | ClogP value |
|---|---|
| (bicyclohexyl diester with -(CH₂)₄-O-acrylate) | 4.164 |
| (bicyclohexyl diester with -(CH₂)₄-O-acrylate) | 4.164 |
| (bicyclohexyl diester with -(CH₂)₄-O-acrylate) | 4.164 |
| (cyclohexane diester-phenyl-CH₂CH₂-O-succinate-O-CH₂-C(CH₃)₂-CH₂-O-acrylate) | 3.156 |
| (cyclohexane diester-phenyl-CH₂CH₂-O-succinate-O-CH₂CH₂-O-acrylate) | 2.847 |
| (cyclohexane diester-phenyl-O-(CH₂)₄-O-acrylate) | 4.057 |
| (cyclohexane diester-phenyl-O-(CH₂)₅-O-acrylate) | 4.057 |
| (cyclohexane diester-phenyl-O-(CH₂)₄-O-acrylate) | 4.057 |

TABLE 4-continued

| Structure | Value |
|---|---|
| (structure 1) | 3.156 |
| (structure 2) | 2.847 |
| (structure 3) | 3.559 |
| (structure 4) | 4.057 |
| (structure 5) | 3.559 |
| (structure 6) | 5.189 |

Moreover, in the polymerizable liquid crystal compound of the embodiment of the present invention, at least one of the group represented by $L^1$-$SP^1$-$A^1$-$D^3$-$G^1$-$D^1$ (X group) or the group represented by $L^2$-$SP^2$-$A^2$-$D^4$-$G^2$-$D^2$ (Y group) in Formula (1) has a C log P value of 3.3 or more, preferably has a C log P value of 4.0 or more, and more preferably has a C log P value of 5.0 to 6.5.

In the present invention, for a reason that the durability of an optically anisotropic film thus formed is more improved, it is preferable that the C log P value of the group represented by $L^2$-$SP^2$-$A^2$-$D^4$-$G^2$-$D^2$ (Y group) is higher than the C log P value of the group represented by $L^1$-$SP$-$A^1$-$D^3$-$G^1$-$D^1$ (X group) in Formula (1), it is more preferable that the C log P value of the Y group is higher than the C log P value of the X group by 0.1 to 4.0, and it is still more preferable that the C log P value of the Y group is higher than the C log P value of the X group by 0.1 to 3.0.

Furthermore, in the present invention, with regard to the sterically hindered group contained in Ar in Formula (1), for a reason that the durability of an optically anisotropic film thus formed is further improved, $Z^1$ in Formulae (Ar-1) to (Ar-8) is preferably a monovalent aliphatic hydrocarbon group having 3 to 20 carbon atoms, more preferably an alkyl group having 3 to 8 carbon atoms, still more preferably a branched alkyl group having 3 to 8 carbon atoms (for example, an isopropyl group, an n-butyl group, an isobutyl group, a sec-butyl group, and a t-butyl group), and particularly preferably a t-butyl group.

[Method for Producing Polymerizable Liquid Crystal Compound]

The method for producing a polymerizable liquid crystal compound of an embodiment of the present invention (hereinafter also simply referred to as "the production method of the embodiment of the present invention") includes:

a first esterification step of reacting a compound represented by Formula (2) with a compound represented by Formula (3) to produce a phenol compound, and a second esterification step of reacting the phenol compound obtained in the first esterification step with a compound represented by Formula (4) to obtain the polymerizable liquid crystal compound of the embodiment of the present invention,

HO—Ar—OH (2)

$L^1$-$SP^1$-$A^1$-$D^3$-$G^1$-COOH (3)

$L^2$-$SP^2$-$A^2$-$D^4$-$G^2$-COOH (4).

Here, Ar in Formula (2), all of $L^1$, $SP^1$, $A^1$, $D^3$, and $G^1$ in Formula (3), and $L^2$, $SP^2$, $A^2$, $D^4$, and $G^2$ in Formula (4) are the same as those described in Formula (1). In particular, in the first esterification step in which the compound represented by Formula (2) is reacted with the compound represented by Formula (3), for a reason that the yield of the phenol compound thus produced is improved, it is preferable that Ar in Formula (2) is the same as in Formula (1) and $Z^1$ in Formulae (Ar-1) to (Ar-8) represents a monovalent aliphatic hydrocarbon group having 3 to 20 carbon atoms.

In addition, the polymerizable liquid crystal compound obtained by the production method of the embodiment of the present invention is the polymerizable liquid crystal compound represented by Formula (1), in which both of $D^1$ and $D^2$ in Formula (1) represent ester bonds (—O—CO—).

[First Esterification Step]

The first esterification step is a step of reacting the compound represented by Formula (2) with the compound represented by Formula (3) to produce a phenol compound, and is specifically, a step of producing a phenol compound represented by Formula (5).

$$L^1\text{-}SP^1\text{-}A^1\text{-}D^3\text{-}G^1\text{-}COO\text{—}Ar\text{—}OH \qquad (5)$$

Here, in Formula (5), all of $L^1$, $SP^1$, $A^1$, $D^3$, and $G^1$ are the same as those described in Formula (1).

The reaction condition for the reaction of the compound represented by Formula (2) with the compound represented by Formula (3) is not particularly limited, and a reaction condition for esterification known in the related art can be appropriately adopted.

For example, the reaction is preferably performed at a temperature of −10° C. to 40° C., more preferably performed at a temperature of −5° C. to 30° C., and still more preferably performed at a temperature of 0° C. to 20° C.

In addition, the reaction is preferably performed for a period of 10 minutes to 24 hours, more preferably performed for a period of 1 hour to 10 hours, and still more preferably performed for a period of 1 hour to 8 hours.

[Second Esterification Step]

The second esterification step is a step in which the phenol compound obtained in the first esterification step is reacted with the compound represented by Formula (4) to obtain the polymerizable liquid crystal compound of the embodiment of the present invention, and is specifically a step in which the phenol compound represented by Formula (5) is reacted with the compound represented by Formula (4) to obtain a polymerizable liquid crystal compound represented by Formula (1A).

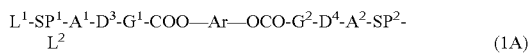

$$L^1\text{-}SP^1\text{-}A^1\text{-}D^3\text{-}G^1\text{-}COO\text{—}Ar\text{—}OCO\text{-}G^2\text{-}D^4\text{-}A^2\text{-}SP^2\text{-}L^2 \qquad (1A)$$

Here, in Formula (1A), all of $L^1$, $SP^1$, $A^1$, $D^3$, and $G^1$, and $L^2$, $SP^2$, $A^2$, $D^4$ and $G^2$ are the same as those described in Formula (1).

The condition for the reaction of the phenol compound represented by Formula (5) with the compound represented by Formula (4) is not particularly limited, and a reaction condition for esterification known in the related art can be appropriately adopted.

For example, the reaction is preferably performed at a temperature of −10° C. to 40° C., more preferably performed at a temperature of −5° C. to 30° C., and still more preferably performed at a temperature of 0° C. to 20° C.

In addition, the reaction is preferably performed for a period of 10 minutes to 24 hours, more preferably performed for a period of 1 hour to 10 hours, and still more preferably performed for a period of 1 hour to 8 hours.

[Polymerizable Liquid Crystal Composition]

The polymerizable liquid crystal composition of an embodiment of the present invention is a polymerizable liquid crystal composition containing the above-mentioned polymerizable liquid crystal compound of the embodiment of the present invention, and can contain other polymerizable compounds, polymerization initiators, solvents, or the like which will be described later, in addition to the polymerizable liquid crystal compound of the embodiment of the present invention.

[Other Polymerizable Compounds]

The polymerizable liquid crystal composition of the embodiment of the present invention may include other polymerizable compounds, in addition to the above-mentioned polymerizable liquid crystal compound of the embodiment of the present invention.

Here, a polymerizable group contained in such other polymerizable compounds is not particularly limited, and examples thereof include a (meth)acryloyl group, a vinyl group, a styryl group, and an allyl group. Among those, the (meth)acryloyl group is preferably contained.

For a reason that the durability of an optically anisotropic film thus formed is further improved, such other polymerizable compounds are preferably polymerizable compounds having 2 to 4 polymerizable groups, and more preferably polymerizable compounds having 2 polymerizable groups.

Examples of such other polymerizable compounds include the compounds described in paragraphs [0073] and [0074] of JP2016-053709A.

Furthermore, examples of such other polymerizable compounds include the compounds represented by Formulae (M1), (M2), and (M3) described in paragraphs [0030] to [0033] of JP2014-077068A, and more specifically, the specific examples described in paragraphs [0046] to [0055] of the same publication.

In addition, as such other polymerizable compounds, compounds having the structures of Formulae (1) to (3) described in JP2014-198814A can also be preferably used, and more specifically, examples of such other polymerizable compounds include the specific examples described in paragraphs [0020] to [0035], to [0050], and [0057] of the same publication.

Moreover, examples of such other polymerizable compounds include by-products in the first esterification step in the production method of the embodiment of the present invention.

Examples of such by-products include a polymerizable liquid crystal compound represented by Formula (6), that is, a polymerizable liquid crystal compound in which the structures of two groups extending in the long-axis direction from a center at Ar of the reverse-wavelength dispersion expressing portion are the same as each other.

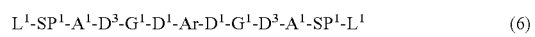

$$L^1\text{-}SP^1\text{-}A^1\text{-}D^3\text{-}G^1\text{-}D^1\text{-}Ar\text{-}D^1\text{-}G^1\text{-}D^3\text{-}A^1\text{-}SP^1\text{-}L^1 \qquad (6)$$

Here, in Formula (6), all of $L^1$, $SP^1$, $A^1$, $D^3$, and $G^1$ are the same as those described in Formula (1).

Specific examples of the polymerizable liquid crystal compound represented by Formula (6) include the liquid crystal compounds described below. Further, the 1,4-cyclohexylene groups in the following formulae are all trans-1,4-cyclohexylene groups.

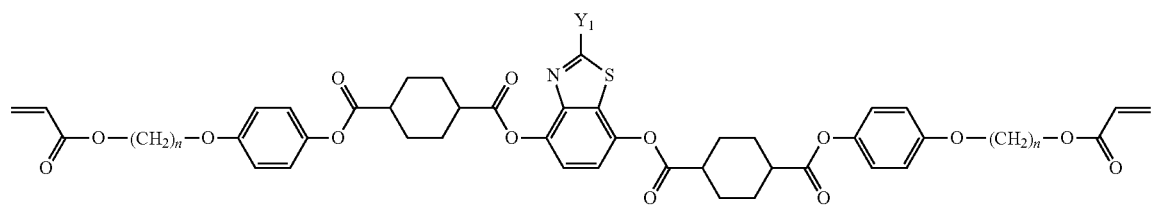
| No | Y1 | n |
|---|---|---|
| II-1-1 | phenyl | 6 |
| II-1-2 | 4-CN-phenyl | 6 |
| II-1-3 | 4-NO₂-phenyl | 6 |
| II-1-4 | 4-pyridyl | 6 |
| II-1-5 | 4-(styryl)phenyl | 6 |
| II-1-6 | 4-NO₂-phenyl | 11 |

-continued
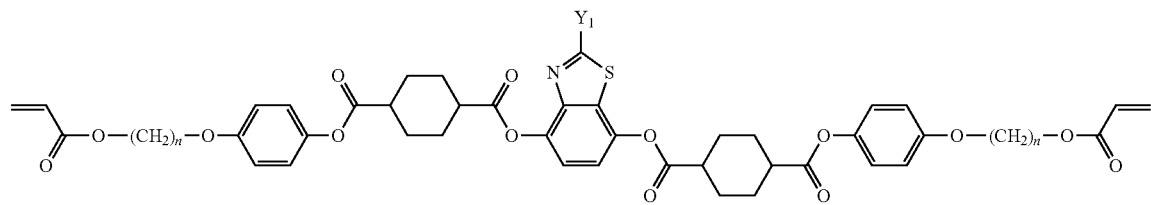
| No | Y1 | n |
|---|---|---|
| II-1-7 | 4-nitrophenyl | 8 |
| II-1-8 | 4-nitrophenyl | 4 |
| II-1-9 | thiophen-2-yl | 6 |
| II-1-10 | 3-methyl-4-nitrophenyl | 6 |
| II-1-11 | 4,6-dimethylbenzofuran-2-yl | 6 |
| II-1-12 | furan-2-yl | 6 |
| II-1-13 | 5-chlorothiophen-2-yl | 6 |

-continued
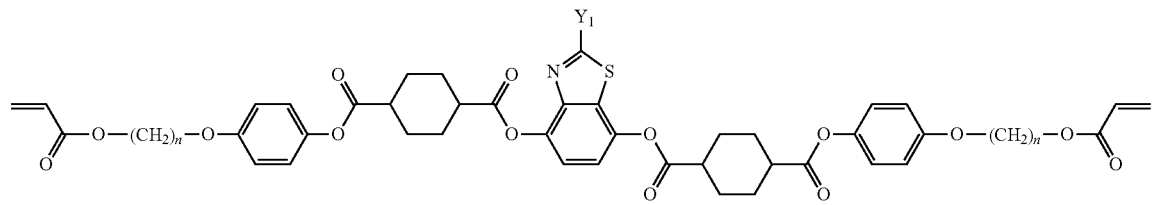
| No | Y1 | n |
|---|---|---|
| II-1-14 | 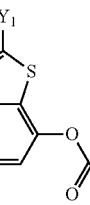 | 6 |
| II-1-15 | 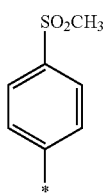 | 6 |
II-1-16
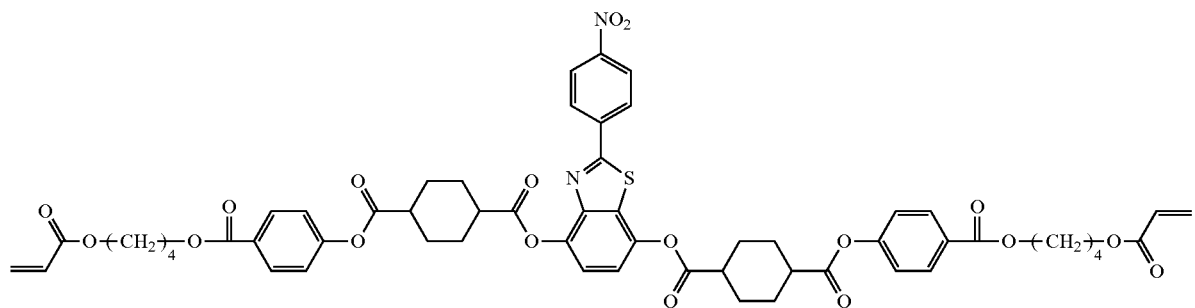
II-1-17
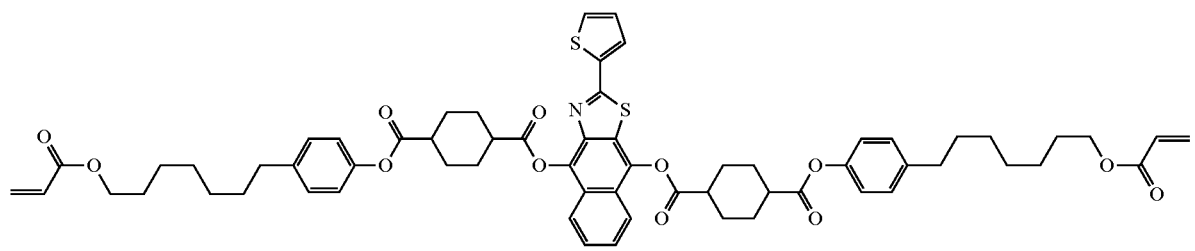
II-1-18
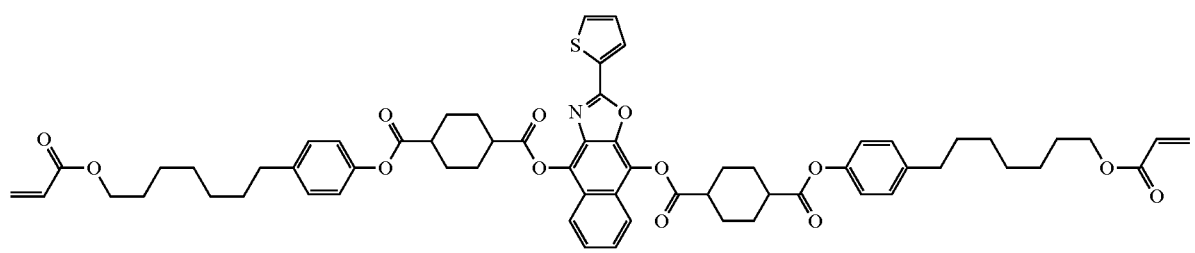

| No | X | R1 |
|---|---|---|
| II-2-1 | NC—*—CN | H |
| II-2-2 | NC—*—C(O)—O—CH₃ | H |
| II-2-3 | NC—*—C(O)—O—butyl | H |
| II-2-4 | NC—*—C(O)—O—CH₂CH₂—O—C(CH₃)₂—OH | H |
| II-2-5 | NC—*—CN | CH₃ |
| II-2-6 | NC—*—CN | C(CH₃)₃ |
| II-2-7 | S | H |

Furthermore, in the formulae. "*" represents a bonding position.

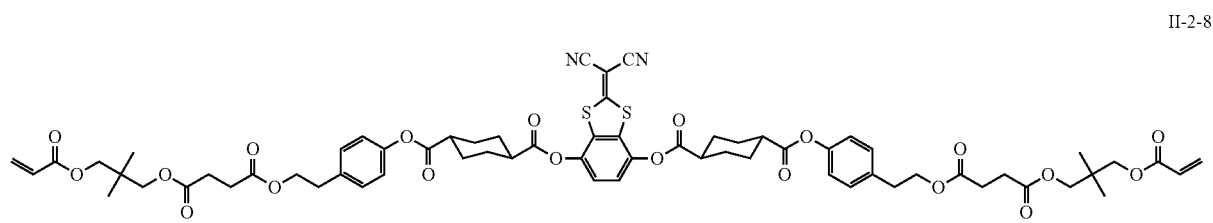

II-2-8

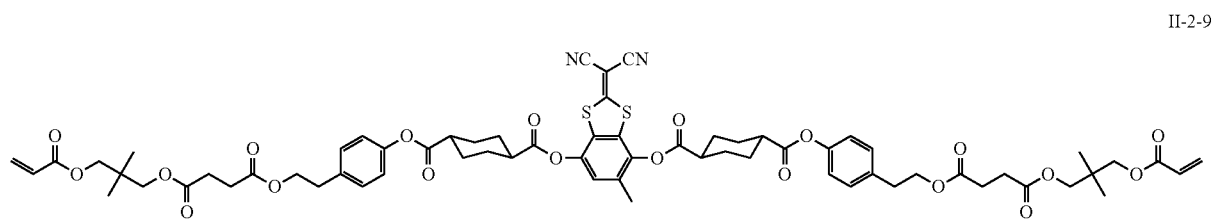

II-2-9

Moreover, a group adjacent to the acryloyloxy group in Formulae II-2-8 and II-2-9 represents a propylene group (a group in which a methyl group is substituted with an ethylene group), and represents a mixture of position isomers in which the positions of the methyl groups are different.

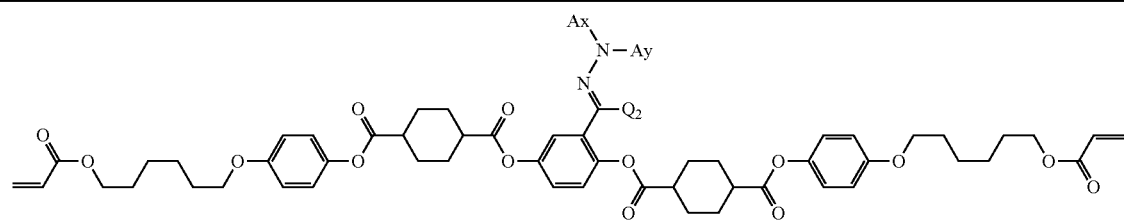
| No | Ax | Ay | Q2 |
|---|---|---|---|
| II-3-1 | benzothiazol-2-yl | H | H |
| II-3-2 | benzothiazol-2-yl | H | H |
| II-3-3 | naphthalen-1-yl | H | H |
| II-3-4 | Ph | Ph | H |
| II-3-5 | quinolin-2-yl | H | H |
| II-3-6 | phthalazin-1-yl | H | H |
| II-3-7 | benzothiazol-2-yl | CH₃ | H |
| II-3-8 | benzothiazol-2-yl | C₄H₉ | H |
| II-3-9 | benzothiazol-2-yl | C₆H₁₃ | H |
| II-3-10 | benzothiazol-2-yl | acryloyl | H |
| II-3-11 | benzothiazol-2-yl | benzothiazol-2-yl | H |
| II-3-12 | benzothiazol-2-yl | CH₂CN | H |

-continued
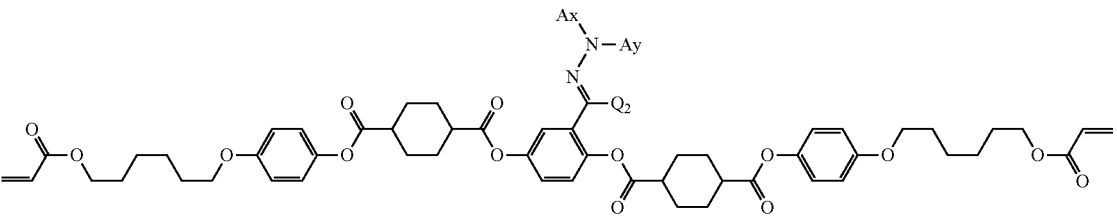
| No | Ax | Ay | Q2 |
|---|---|---|---|
| II-3-13 | 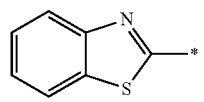 [SMILES: *c1nc2ccccc2s1] | 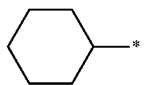 | H |
| II-3-14 | 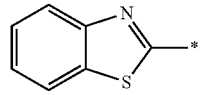 [SMILES: *c1nc2ccccc2s1] | 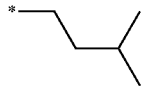 | H |
| II-3-15 | 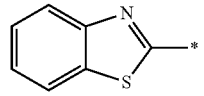 [SMILES: *c1nc2ccccc2s1] | $CH_2CH_2OH$ | H |
| II-3-16 | 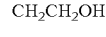 | H | H |
| II-3-17 | 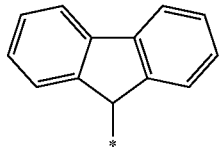 | $CH_2CF_3$ | H |
| II-3-18 | 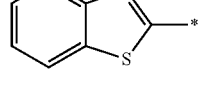 | H | $CH_3$ |
| II-3-19 |  | 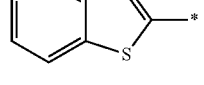 | H |
| II-3-20 |  | 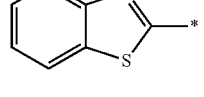 | H |
| II-3-21 | 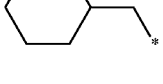 | 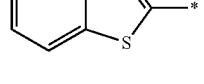 | H |
| II-3-22 | 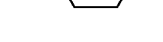 | 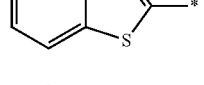 | H |
| II-3-23 | 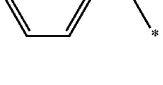 | 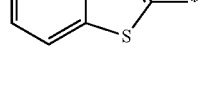 | H |

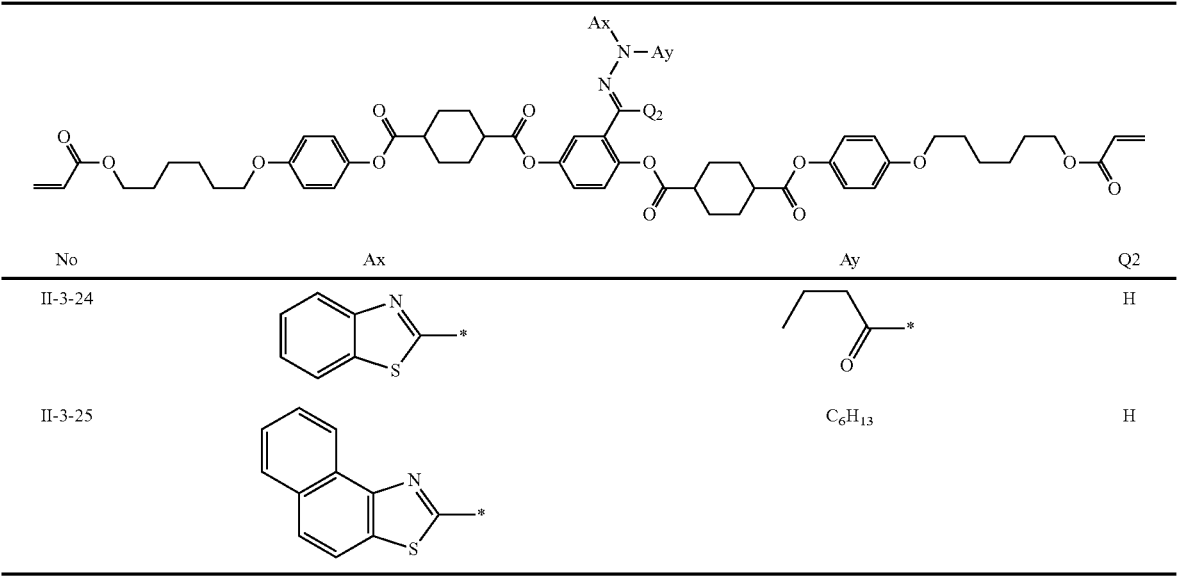
| No | Ax | Ay | Q2 |
|---|---|---|---|
| II-3-24 | benzothiazol-2-yl | propanoyl | H |
| II-3-25 | naphtho[2,1-d]thiazol-2-yl | $C_6H_{13}$ | H |
II-3-26
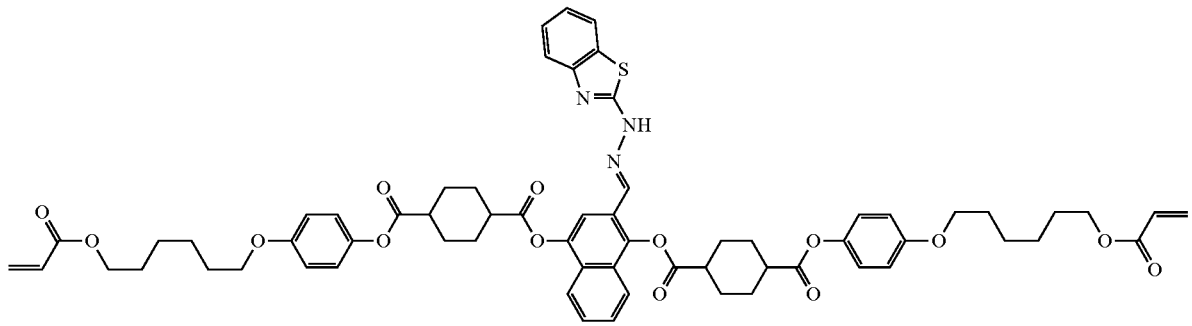
II-3-27
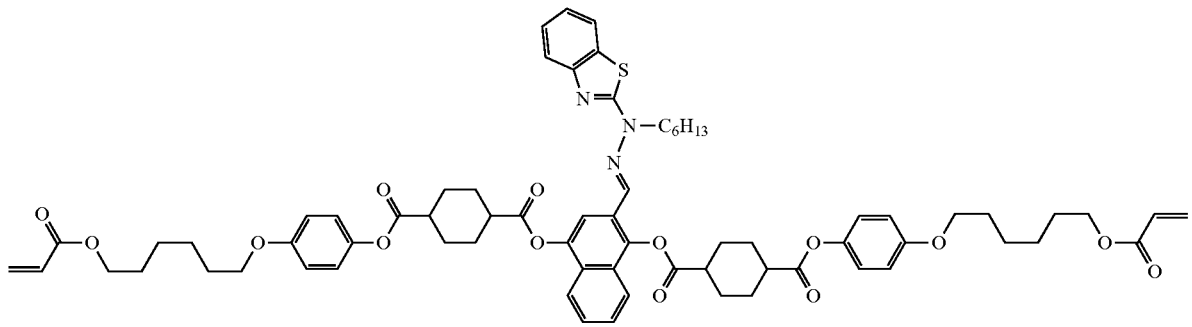

II-3-28
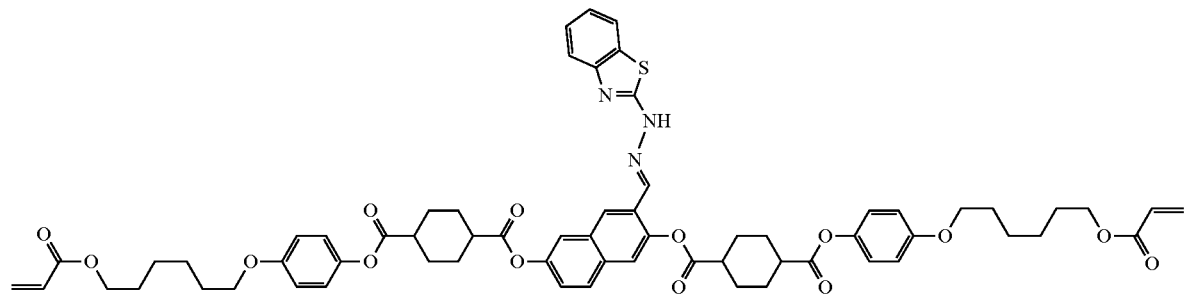
II-3-29
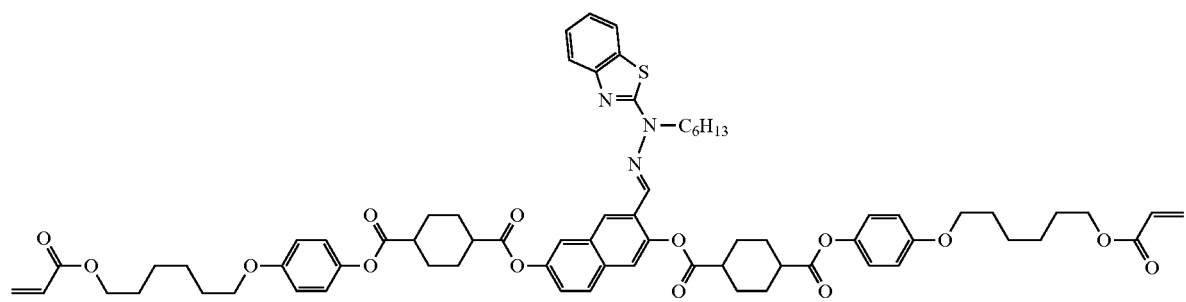
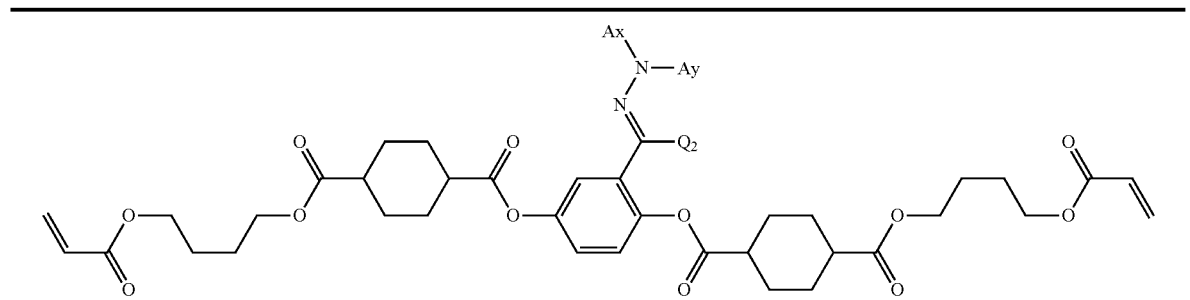
| No | Ax | Ay | Q2 |
|---|---|---|---|
| II-3-30 | benzothiazol-2-yl | H | H |
| II-3-31 | benzoxazol-2-yl | H | H |
| II-3-32 | naphthalen-1-yl | H | H |
| II-3-33 | Ph | Ph | H |
| II-3-34 | quinolin-2-yl | H | H |

-continued
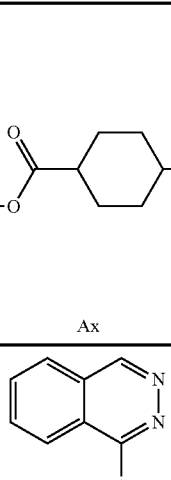
| No | Ax | Ay | Q2 |
|---|---|---|---|
| II-3-35 | 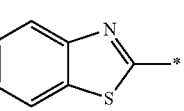 | H | H |
| II-3-36 | 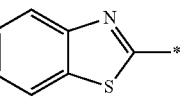 | CH$_3$ | H |
| II-3-37 | 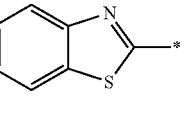 | C$_4$H$_9$ | H |
| II-3-38 | 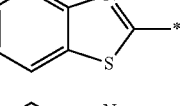 | C$_6$H$_{13}$ | H |
| II-3-39 | 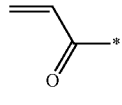 | 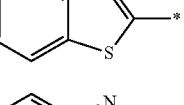 | H |
| II-3-40 |  | 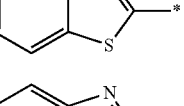 | H |
| II-3-41 | 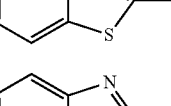 | CH$_2$CN | H |
| II-3-42 | 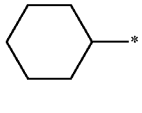 [SMILES: *C1CCCCC1] | 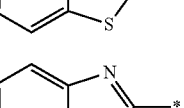 | H |
| II-3-43 | 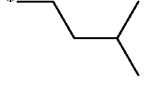 | 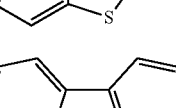 | H |
| II-3-44 | 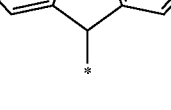 | CH$_2$CH$_2$OH | H |
| II-3-45 |  | H | H |

-continued
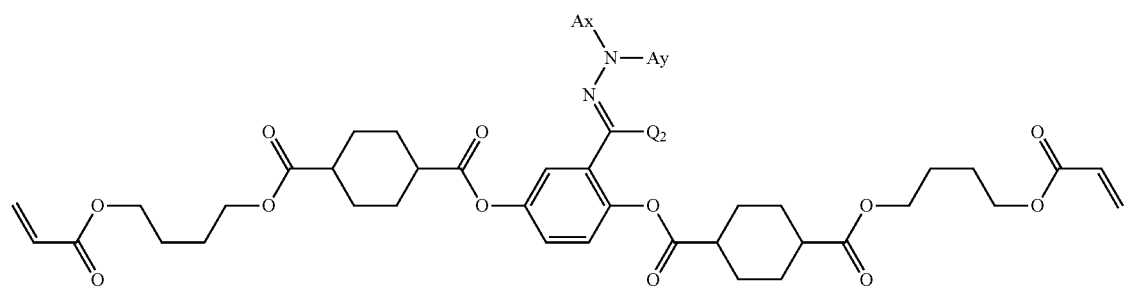
| No | Ax | Ay | Q2 |
|---|---|---|---|
| II-3-46 | 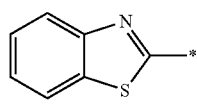 [SMILES: *c1nc2ccccc2s1] | CH$_2$CF$_3$ | H |
| II-3-47 | 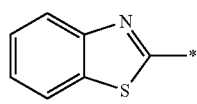 [SMILES: *c1nc2ccccc2s1] | H | CH$_3$ |
| II-3-48 | 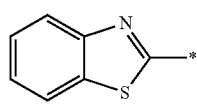 [SMILES: *c1nc2ccccc2s1] | 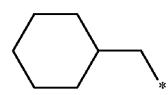 [SMILES: *CC1CCCCC1] | H |
| II-3-49 | 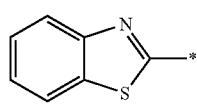 [SMILES: *c1nc2ccccc2s1] | 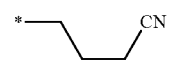 [SMILES: *CCCC#N] | H |
| II-3-50 | 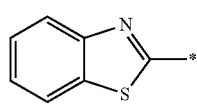 [SMILES: *c1nc2ccccc2s1] | 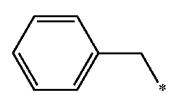 | H |
| II-3-51 | 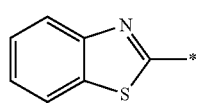 [SMILES: *c1nc2ccccc2s1] | 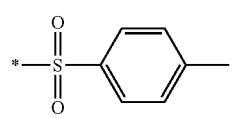 [SMILES: *S(=O)(=O)c1ccc(C)cc1] | H |
| II-3-52 | 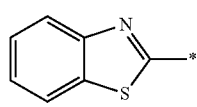 [SMILES: *c1nc2ccccc2s1] | 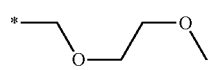 | H |
| II-3-53 | 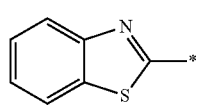 [SMILES: *c1nc2ccccc2s1] | 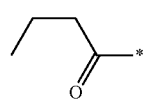 [SMILES: *C(=O)CCC] | H |
| II-3-54 | 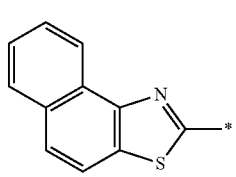 [SMILES: *c1nc2c(ccc3ccccc32)s1] | C$_6$H$_{13}$ | H |

II-3-55
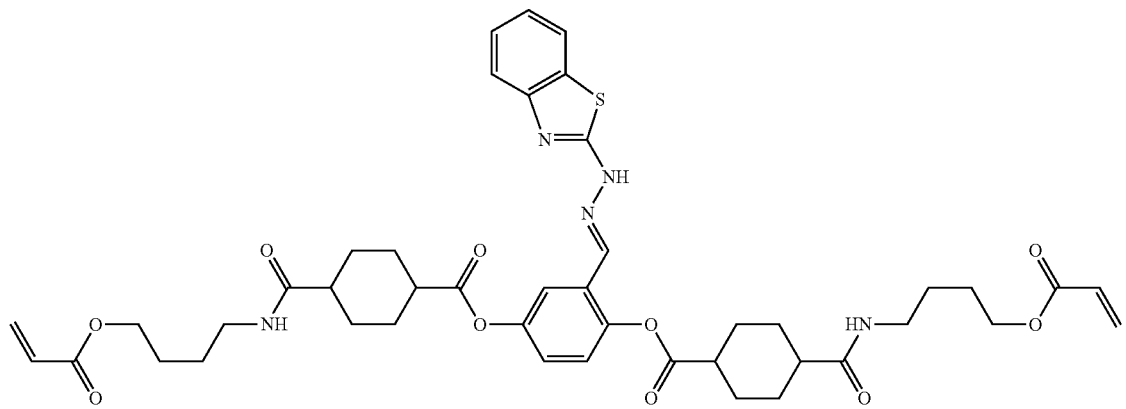
II-4-1
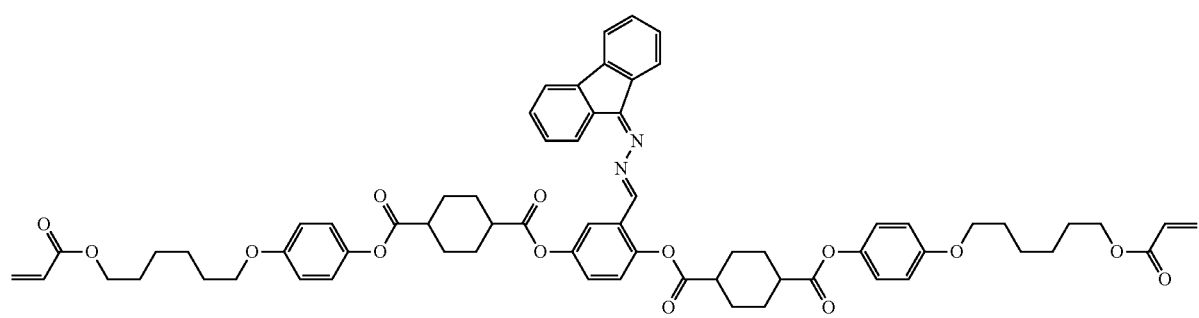
II-4-2
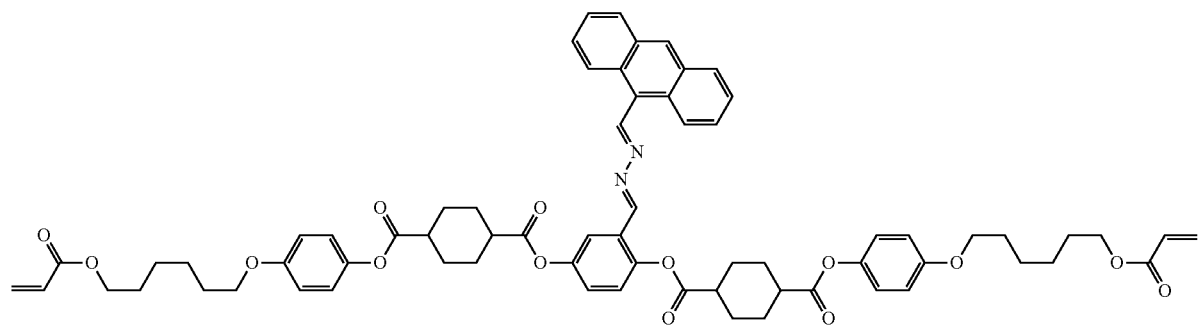
II-4-3
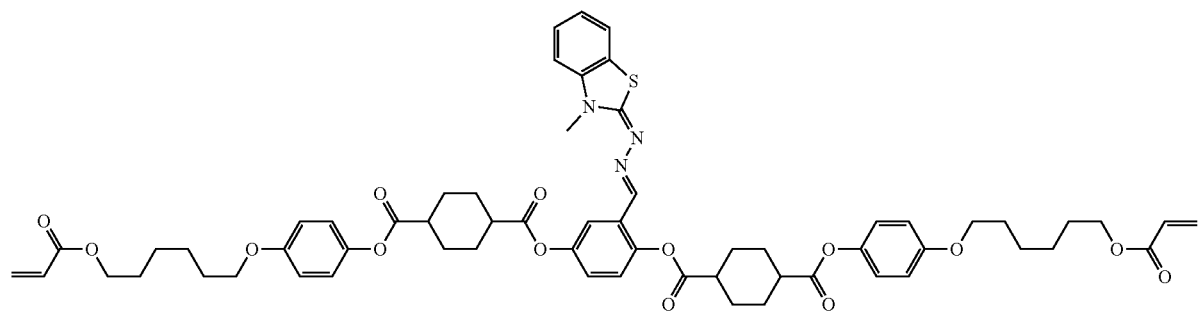

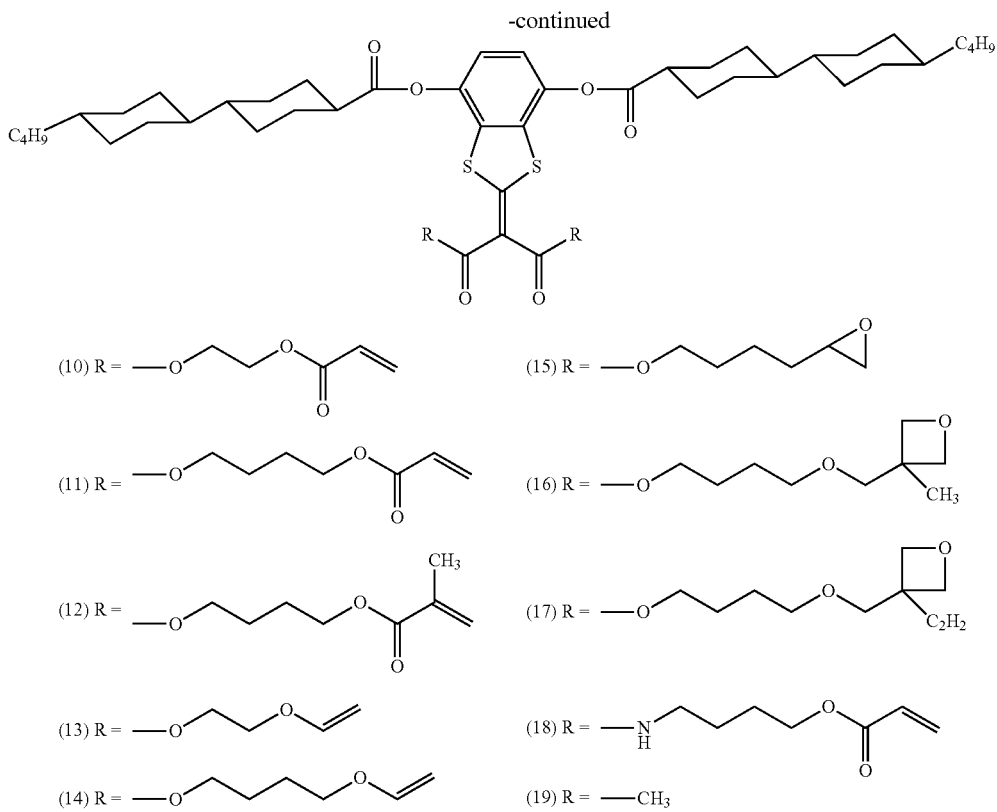

-continued

(10) R = 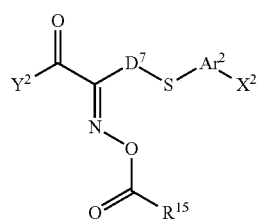

(Structures 10-19 showing various R groups)

[Polymerization Initiator]

The polymerizable liquid crystal composition of the embodiment of the present invention preferably contains a polymerization initiator.

The polymerization initiator to be used is preferably a photopolymerization initiator capable of initiating a polymerization reaction upon irradiation with ultraviolet rays.

Examples of the photopolymerization initiator include α-carbonyl compounds (described in each of the specifications of U.S. Pat. Nos. 2,367,661A and 2,367,670A), acyloin ethers (described in U.S. Pat. No. 2,448,828A), α-hydrocarbon-substituted aromatic acyloin compounds (described in U.S. Pat. No. 2,722,512A), multinuclear quinone compounds (as described in each of the specifications of U.S. Pat. Nos. 3,046,127A and 2,951,758A), combinations of triarylimidazole dimer and p-aminophenyl ketone (as described in U.S. Pat. No. 3,549,367A), acridine and phenazine compounds (described in JP1985-105667A (JP-S60-105667A) and U.S. Pat. No. 4,239,850A), oxadiazole compounds (described in U.S. Pat. No. 4,212,970A), and acyl phosphine oxide compounds (described in JP1988-040799B (JP-S63-040799B), JP1993-029234B (JP-H05-029234B), JP1998-095788A (JP-H10-095788A), and JP1998-029997A (JP-H10-029997A)).

In the present invention, for a reason that the durability becomes better, the polymerization initiator is preferably an oxime-type polymerization initiator, and specifically, a polymerization initiator represented by Formula (PI) is more preferable.

(PI)

In Formula (PI), $X^2$ represents a hydrogen atom or a halogen atom.

Furthermore, in Formula (PI), $Ar^2$ represents a divalent aromatic group, and $D^7$ represents a divalent organic group having 1 to 12 carbon atoms.

In addition, in Formula (PI), $R^{15}$ represents an alkyl group having 1 to 12 carbon atoms, and $Y^2$ represents a monovalent organic group.

In Formula (PI), examples of the halogen atom represented by $X^2$ include a fluorine atom, a chlorine atom, a bromine atom, and an iodine atom, and among those, the chlorine atom is preferable.

Furthermore, in Formula (PI), examples of the divalent aromatic group represented by $Ar^2$ include aromatic hydrocarbon rings such as a benzene ring, a naphthalene ring, an anthracene ring, and a phenanthroline ring; and divalent groups having an aromatic heterocycle, such as a furan ring, a pyrrole ring, a thiophene ring, a pyridine ring, a thiazole ring, and a benzothiazole ring.

Incidentally, in Formula (PI), examples of the divalent organic having 1 to 12 carbon atoms represented by $D^7$ include a linear or branched alkylene group having 1 to 12 carbon atoms, and specific suitable examples thereof include a methylene group, an ethylene group, and a propylene group.

Moreover, in Formula (PI), specific suitable examples of the alkyl group having 1 to 12 carbon atoms represented by $R^{15}$ include a methyl group, an ethyl group, and a propyl group.

In addition, in Formula (PI), examples of the monovalent organic group represented by $Y^2$ include a functional group including a benzophenone skeleton (($C_6H_5$)$_2$CO). Specifically, as with groups represented by Formula (PIa) and Formula (PIb), a functional group including a benzophenone skeleton in which a benzene ring at a terminal is unsubstituted or mono-substituted is preferable. Further, in Formula (PIa) and Formula (PIb), * represents a bonding position, and that is, a bonding position to a carbon atom of a carbonyl group in Formula (PI).

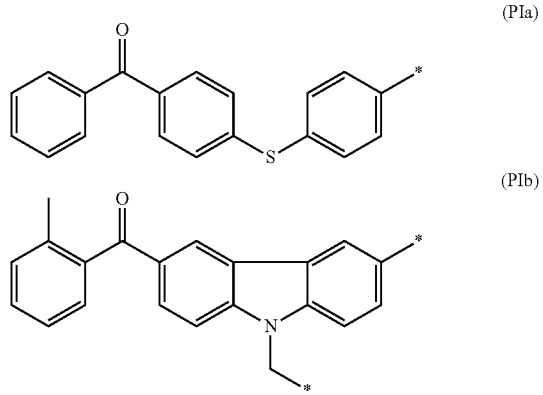

Examples of the oxime-type polymerization initiator represented by Formula (PI) include a compound represented by Formula (PI-1) and a compound represented by Formula (PI-2).

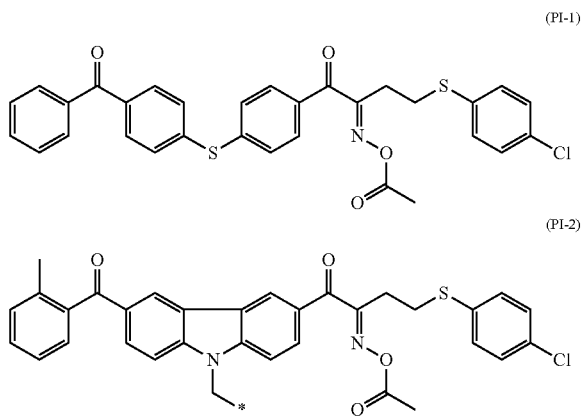

[Solvent]

The polymerizable liquid crystal composition of the embodiment of the present invention preferably contains a solvent from the viewpoint of workability for forming an optically anisotropic film, and the like.

Specific examples of the solvent include ketones (for example, acetone, 2-butanone, methyl isobutyl ketone, and cyclohexanone), ethers (for example, dioxane and tetrahydrofuran), aliphatic hydrocarbons (for example, hexane), alicyclic hydrocarbons (for example, cyclohexane), aromatic hydrocarbons (for example, toluene, xylene, and trimethylbenzene), halogenated carbons (for example, dichloromethane, dichloroethane, dichlorobenzene, and chlorotoluene), esters (for example, methyl acetate, ethyl acetate, and butyl acetate), water, alcohols (for example, ethanol, isopropanol, butanol, and cyclohexanol), cellosolves (for example, methyl cellosolve and ethyl cellosolve), cellosolve acetates, sulfoxides (for example, dimethyl sulfoxide), and amides (for example, dimethylformamide and dimethylacetamide), and these may be used alone or in combination of two or more kinds thereof.

[Leveling Agent]

From the viewpoint that the surface of the optically anisotropic film is maintained smooth and alignment is easily controlled, the polymerizable liquid crystal composition of the embodiment of the present invention preferably contains a leveling agent.

For a reason that a leveling effect on the addition amount is high, such the leveling agent is preferably a fluorine-based leveling agent or a silicon-based leveling agent, and from the viewpoint that it is less likely to cause bleeding (bloom or bleed), the fluorine-based leveling agent is more preferable.

Specific example of the leveling agent include the compounds described in paragraphs [0079] to [0102] of JP2007-069471A, the compound represented by General Formula (I) described in JP2013-047204A (in particular, the compounds described in paragraphs [0020] to [0032]), the compound represented by General Formula (I) described in JP2012-211306A (in particular, the compounds described in paragraphs [0022] to [0029]), the liquid crystal alignment accelerator represented by General Formula (I) described in JP2002-129162A (in particular, the compounds described in paragraphs [0076] to [0078] and to [0084]), and the compound represented by General Formulae (I) and (II) or (III) described in 22005-099248A (in particular, the compounds described in paragraphs [0092] to [0096]). Further, the leveling agent may also function as an alignment control agent which will be described later.

[Alignment Control Agent]

The polymerizable liquid crystal composition of the embodiment of the present invention can contain an alignment control agent, as desired.

With the alignment control agent, various alignment states such as homeotropic alignment (vertical alignment), inclined alignment, hybrid alignment, and cholesteric alignment, in addition to the other homogeneous alignment, can be formed, and specific alignment states can be more uniformly and more accurately controlled and achieved.

As an alignment control agent that accelerates the homogeneous alignment, for example, a low-molecular-weight alignment control agent or a high-molecular-weight alignment control agent can be used.

With regard to the low-molecular-weight alignment control agent, reference can be made to the description in, for example, paragraphs [0009] to [0038] of JP2002-020363A, paragraphs [0111] to [0120] of JP2006-106662A, and paragraphs [0021] to [0029] of JP2012-211306A, the contents of which are incorporated herein by reference.

In addition, with regard to the high-molecular-weight alignment control agent, reference can be made to the description in, for example, paragraphs [0021] to [0057] of JP2004-198511A and paragraphs [0121] to [0167] of JP2006-106662A, the contents of which are incorporated herein by reference.

Furthermore, examples of the alignment control agent that forms or accelerates the homeotropic alignment include a boronic acid compound and an onium salt compound, and specifically, reference can be made to the compounds described in paragraphs [0023] to [0032] of JP2008-225281A, paragraphs [0052] to [0058] of JP2012-208397A, paragraphs [0024] to of JP2008-026730A, paragraphs [0043] to [0055] of JP2016-193869A, and the like, the contents of which are incorporated herein by reference.

On the other hand, cholesteric alignment can be achieved by adding a chiral agent to the polymerizable composition of the embodiment of the present invention, and it is possible to control the turning direction of the cholesteric alignment by its chiral direction. Incidentally, it is possible to control the pitch of the cholesteric alignment in accordance with the alignment regulating force of the chiral agent.

In a case where an alignment control agent is contained, a content of the alignment control agent is preferably 0.01% to 10% by mass, and more preferably 0.05% to 5% by mass, with respect to the total solid content mass of the polymerizable liquid crystal composition. In a case where the content is within the range, precipitation or phase separation, alignment defects, or the like does not occur while achieving a desired alignment state, and an optically anisotropic film which is uniform and highly transparent can be obtained.

These alignment control agents can further impart a polymerizable functional group, in particular, a polymerizable functional group which can be polymerized with a polymerizable liquid crystal compound constituting the polymerizable liquid crystal composition of the embodiment of the present invention.

[Other Components]

The polymerizable liquid crystal composition of the embodiment of the present invention may contain components other than the above-mentioned components, and examples thereof include a liquid crystal compound, a surfactant, a tilt angle control agent, an alignment aid, a plasticizer, and a crosslinking agent, each of which is other than the above-mentioned polymerizable liquid crystal compound.

[Optically Anisotropic Film]

An optically anisotropic film of an embodiment of the present invention is an optically anisotropic film obtained by polymerization of the above-mentioned polymerizable liquid crystal composition of the above-mentioned embodiment of the present invention.

Examples of the method for forming the optically anisotropic film include a method in which the above-mentioned polymerizable liquid crystal composition of the embodiment of the present invention is used to form a desired alignment state and then fixed by polymerization.

Here, the polymerization condition is not particularly limited, but in the polymerization by irradiation with light, ultraviolet rays are preferably used. The irradiation dose is preferably 10 mJ/cm$^2$ to 50 J/cm$^2$, more preferably 20 mJ/cm$^2$ to 5 J/cm$^2$, still more preferably 30 mJ/cm$^2$ to 3 J/cm$^2$, and particularly preferably 50 mJ/cm$^2$ to 1,000 mJ/cm$^2$. In addition, the polymerization may be carried out under a heating condition in order to accelerate the polymerization reaction.

Moreover, in the present invention, the optically anisotropic film can be formed on an optional support in the optical film of an embodiment of the present invention which will be described later or a polarizer in a polarizing plate of an embodiment of the present invention which will be described later.

The optically anisotropic film of the embodiment of the present invention is preferably a positive A plate or a positive C plate, and more preferably the positive A plate.

Here, the positive A plate (A plate which is positive) and the positive C plate (C plate which is positive) are defined as follows.

In a case where a refractive index in the slow phase axis direction in a film plane (in the direction in which the in-plane refractive index is maximum) is defined as nx, a refractive index in an in-plane direction perpendicular in the in-plane slow axis is defined as ny, and a refractive index in the thickness direction is defined as nz, the positive A plate satisfies the relationship of Formula (A1) and the positive C plate satisfies the relationship of Formula (C1). Incidentally, the positive A plate shows a positive value as the Rth and the positive C plate shows a negative value as the Rth.

$$nx > ny \approx nz \qquad \text{Formula (A1)}$$

$$nz > nx \approx ny \qquad \text{Formula (C1)}$$

Furthermore, "≈" encompasses not only a case where the both are completely the same but also a case where the both are substantially the same.

The expression, "substantially the same", means that in the positive A plate, for example, a case where (ny−nz)×d (in which d is the thickness of a film) is −10 to 10 nm, and preferably −5 to 5 nm is also included in "ny=nz" and a case where (nx−nz)×d is −10 to 10 nm, and preferably −5 to 5 nm is also included in "nx=nz". In addition, in the positive C plate, for example, a case where (nx−ny)×d (in which d is the thickness of a film) is 0 to 10 nm, and preferably 0 to 5 nm is also included in "nx=ny".

In a case where the optically anisotropic film of the embodiment of the present invention is a positive A plate, from the viewpoint that it functions as a λ/4 plate, the Re (550) is preferably 100 to 180 nm, more preferably 120 to 160 nm, still more preferably 130 to 150 nm, and particularly preferably 130 to 140 nm.

Here, the "λ/4 plate" is a plate having a λ/4 function, specifically, a plate having a function of converting a linear polarized light at a specific wavelength into a circularly polarized light (or converting a circularly polarized light to a linear polarized light).

[Optical Film]

The optical film of the embodiment of the present invention is an optical film having the optically anisotropic film of the embodiment of the present invention.

Figure 1B:
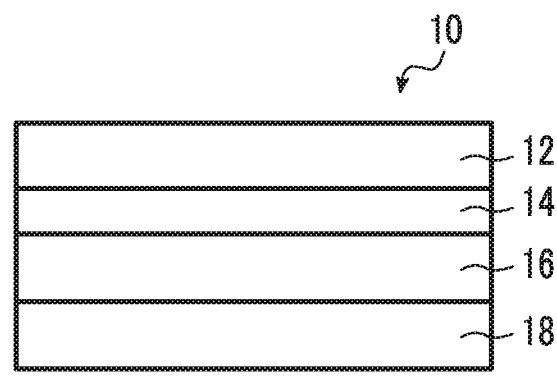
FIG. 1B is a schematic cross-sectional view showing an example of the optical film of the embodiment of the present invention.
Figure 1C:
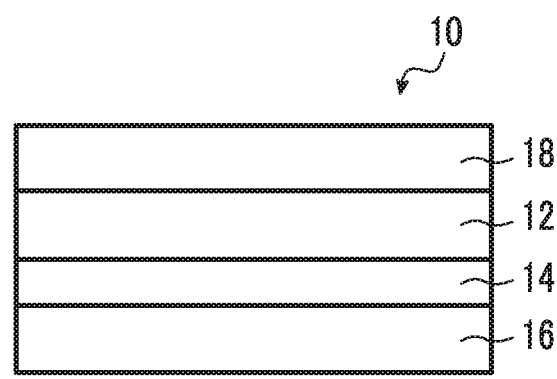
FIG. 1C is a schematic cross-sectional view showing an example of the optical film of the embodiment of the present invention.

FIG. 1A, FIG. 1B, and FIG. 1C (these drawings are hereinafter simply abbreviated as "FIG. 1" unless it is necessary that they are particularly distinguished from each other) are each a cross-sectional view schematically showing an example of the optical film of the embodiment of the present invention.

Furthermore, FIG. 1 is a schematic view, and the thicknesses relationship, the positional relationship, and the like among the respective layers do not necessarily coincide with actual ones. Any of the support, the alignment film and the hard coat layer shown in FIG. 1 are both optional constitutional members.

An optical film 10 shown in FIG. 1 has a support 16, an alignment film 14, and an optically anisotropic film 12 in this order.

In addition, the optical film 10 may have a hard coat layer 18 on the side of the support 16 opposite to the side on which the alignment film 14 is provided as shown in FIG. 1B, and may have the hard coat layer 18 on the side of the optically anisotropic film 12 opposite to the side on which the alignment film 14 is provided as shown in FIG. 1C.

Hereinafter, various members used for the optical film of the embodiment of the present invention will be described in detail.

[Optically Anisotropic Film]

The optically anisotropic film contained in the optical film of the embodiment of the present invention is the above-mentioned optically anisotropic film of the embodiment of the present invention.

In the optical film of the embodiment of the present invention, the thickness of the optically anisotropic film is not particularly limited, but is preferably 0.1 to 10 µm, and more preferably 0.5 to 5 µm.

[Support]

The optical film of the embodiment of the present invention may have a support as a base material for forming an optically anisotropic film as described above.

Such a support is preferably transparent, and specifically, the support preferably has a light transmittance of 80% or more.

Examples of such a support include a glass substrate and a polymer film. Examples of the material for the polymer film include cellulose-based polymers; acrylic polymers having acrylic acid ester polymers such as polymethyl methacrylate and a lactone ring-containing polymer; thermoplastic norbornene-based polymers; polycarbonate-based polymers; polyester-based polymers such as polyethylene terephthalate and polyethylene naphthalate; styrene-based polymers such as polystyrene and an acrylonitrile-styrene copolymer (AS resin); polyolefin-based polymers such as polyethylene, polypropylene, and an ethylene-propylene copolymer; vinyl chloride-based polymers; amide-based polymers such as nylon and aromatic polyamide; imide-based polymers; sulfone-based polymers; polyether sulfone-based polymers; polyether ether ketone-based polymers; polyphenylene sulfide-based polymers; vinylidene chloride-based polymers; vinyl alcohol-based polymers; vinyl butyral-based polymers; arylate-based polymers; polyoxymethylene-based polymers; epoxy-based polymers; and polymers containing a mixture of these polymers.

In addition, an aspect in which the polarizer which will be described later may also function as such a support is also available.

In the present invention, the thickness of the support is not particularly limited, but is preferably 5 to 60 µm, and more preferably 5 to 30 µm.

[Alignment Film]

In a case where the optical film of the embodiment of the present invention has the above-mentioned optional support, it is preferable that the optical film has an alignment film between the support and the optically anisotropic film. Further, in an aspect, the above-mentioned support may also function as an alignment film.

The alignment film generally has a polymer as a main component. The materials for the polymer material for an alignment film are described in many documents, and many commercially available products can be used.

The polymer material used in the present invention is preferably a polyvinyl alcohol or a polyimide, or a derivative thereof. Particularly, a modified or non-modified polyvinyl alcohol is preferable.

Examples of the alignment film that can be used in the present invention include the alignment films described in Line 24 on Page 43 to Line 8 on Page 49 of WO01/088574A; the modified polyvinyl alcohols described in paragraphs [0071] to [0095] of JP3907735B; and the liquid crystal alignment film formed by a liquid crystal aligning agent described in JP2012-155308A.

In the present invention, for a reason that deterioration in the surface state can be prevented by avoiding a contact with the surface of the alignment film upon formation of the alignment film, an optical alignment film is also preferably used as the alignment film.

The optical alignment film is not particularly limited, but the polymer materials such as a polyamide compound and a polyimide compound described in paragraphs [0024] to [0043] of WO2005/096041A; the liquid crystal alignment film formed by a liquid crystal aligning agent having a photoalignable group described in JP2012-155308A; LPP-JP265CP, trade name, manufactured by Rolic technologies Ltd.; or the like can be used.

In addition, in the present invention, the thickness of the alignment film is not particularly limited, but from the viewpoint of forming an optically anisotropic film having a uniform film thickness by alleviating the surface roughness present on the support, the thickness is preferably 0.01 to 10 µm, more preferably 0.01 to 1 µm, and still more preferably 0.01 to 0.5 µm.

[Hard Coat Layer]

The optical film of the embodiment of the present invention preferably has a hard coat layer in order to impart film physical strength. Specifically, the hard coat layer may be provided on the side of the support opposite to the side on which the alignment film is provided (refer to FIG. 1B) or may be provided on the side of the optically anisotropic film opposite to the side on which the alignment film is provided (refer to FIG. 1C).

As the hard coat layer, those described in paragraphs [0190] to [0196] of JP2009-098658A can be used.

[Other Optically Anisotropic Films]

The optical film of the embodiment of the present invention may have other optically anisotropic films, in addition to the optically anisotropic film of the embodiment of the present invention.

That is, the optical film of the embodiment of the present invention may have a laminated structure having the optically anisotropic film of the embodiment of the present invention and other optically anisotropic films.

Such other optically anisotropic films are not particularly limited as long as the optically anisotropic films are optically anisotropic films by not blending the polymerizable liquid crystal compound represented by Formula (1), and by using the such other polymerizable compounds (particularly, liquid crystal compounds) as described above.

Here, the liquid crystal compounds are generally classified into a rod-like type and a disk-like type according to the shape thereof. Further, each includes a low-molecular-weight type and a high-molecular-weight type. The term "high-molecular-weight" generally refers to having a degree of polymerization of 100 or more (Polymer Physics-Phase Transition Dynamics, by Masao Doi, page. 2, published by Iwanami Shoten, Publishers, 1992). In the present invention, any type of liquid crystal compound can be used, but a rod-like liquid crystal compound or a discotic liquid crystal compound (disk-like liquid crystal compound) is preferably used. Two or more kinds of rod-like liquid crystal compounds, two or more kinds of disk-like liquid crystal compounds, or a mixture of the rod-like liquid crystal compound and the disk-like liquid crystal compound may be used. In order to fix the above-mentioned liquid crystal compound, it is more preferable that the liquid crystal compound is formed of a rod-like liquid crystal compound or disk-like liquid crystal compound having a polymerizable group, and it is still more preferable that the liquid crystal compound has two or more polymerizable groups in one molecule. In the case of a mixture of two or more kinds of the liquid crystal compounds, at least one kind of the liquid crystal compound preferably has two or more polymerizable groups in one molecule.

As the rod-like liquid crystal compound, for example, the rod-like liquid crystal compounds described in claim 1 of JP1999-513019A (JP-H11-513019A) or paragraphs [0026] to [0098] of JP2005-289980A can be preferably used, and as the discotic liquid crystal compounds, for example, the discotic liquid crystal compounds described in paragraphs [0020] to [0067] of JP2007-108732A and paragraphs [0013] to [0108] of JP2010-244038A can be preferably used, but the liquid crystal compounds are not limited thereto.

[Ultraviolet Absorber]

The optical film of the embodiment of the present invention preferably includes an ultraviolet (UV) absorber, taking the effect of external light (particularly ultraviolet rays) into consideration.

The ultraviolet absorber may be contained in the optically anisotropic film of the embodiment of the present invention or may also be contained in a member other than an optically anisotropic film constituting the optical film of the embodiment of the present invention. Suitable examples of the member other than the optically anisotropic film include a support.

As the ultraviolet absorber, any of ultraviolet absorbers known in the related art, which can express ultraviolet absorptivity, can be used. Among such the ultraviolet absorbers, a benzotriazole-based or hydroxyphenyltriazine-based ultraviolet absorber is preferably used from the viewpoint that it has high ultraviolet absorptivity and ultraviolet absorbing ability (ultraviolet-shielding ability) used for an image display device is obtained.

In addition, in order to broaden ultraviolet absorbing ranges, two or more of ultraviolet absorbers having different maximum absorption wavelengths can be used in combination.

Specific examples of the ultraviolet absorber include the compounds described in paragraphs [0255] and [0259] of JP2012-018395A and the compounds described in paragraphs [0055] to [0105] of JP2007-072163A.

In addition, as a commercially available product thereof, for example, Tinuvin 400, Tinuvin 405, Tinuvin 460, Tinuvin 477, Tinuvin 479, and Tinuvin 1577 (all manufactured by BASF) can be used.

[Polarizing Plate]

A polarizing plate of an embodiment of the present invention has the above-mentioned optical film of the embodiment of the present invention and a polarizer.

Furthermore, in a case where the above-mentioned the optically anisotropic film of the embodiment of the present invention is a λ/4 plate (positive A plate), the polarizing plate of the embodiment of the present invention can be used as a circularly polarizing plate.

Incidentally, in a case where the above-mentioned the optically anisotropic film of the embodiment of the present invention is a λ/4 plate (positive A plate), an angle between the slow phase axis of the λ/4 plate and the absorption axis of a polarizer which will be described later polarizer in the polarizing plate of the embodiment of the present invention is preferably 30° to 60°, more preferably 40° to 50°, still more preferably 42° to 48°, and particularly preferably 45°.

Here, the "slow phase axis" of the λ/4 plate means a direction such that the refractive index in the plane of the λ/4 plate becomes maximum, and the "absorption axis" of the polarizer means a direction such that the absorbance is highest.

[Polarizer]

A polarizer contained in a polarizing plate of an embodiment of the present invention is not particularly limited as long as it is a member having a function of converting light into specific linearly polarized light, and an absorptive type polarizer and a reflective type polarizer, which are known in the related art, can be used.

An iodine-based polarizer, a dye-based polarizer using a dichroic dye, a polyene-based polarizer, or the like is used as the absorptive type polarizer. The iodine-based polarizer and the dye-based polarizer encompass a coating type polarizer and a stretching type polarizer, any of which can be applied, but a polarizer which is manufactured by allowing polyvinyl alcohol to adsorb iodine or a dichroic dye and performing stretching is preferable.

In addition, examples of a method of obtaining a polarizer by performing stretching and dyeing in a state of a laminated film in which a polyvinyl alcohol layer is formed on a basic material include the methods disclosed in JP5048120B, JP5143918B, JP4691205B, JP4751481B, and JP4751486B, and known technologies related to these polarizers can also be preferably used.

A polarizer in which thin films having different birefringence are laminated, a wire grid type polarizer, a polarizer in which a cholesteric liquid crystal having a selective reflection range and a ¼ wavelength plate are combined, or the like is used as the reflective type polarizer.

Among these, a polarizer including a polyvinyl alcohol-based resin (a polymer including —$CH_2$—CHOH— as a repeating unit, in particular, at least one selected from the group consisting of a polyvinyl alcohol and an ethylene-vinyl alcohol copolymer) is preferable from the viewpoint that the adhesiveness is more excellent.

In the present invention, the thickness of the polarizer is not particularly limited, but is preferably 3 µm to 60 µm, more preferably 5 µm to 30 µm, and still more preferably 5 µm to 15 µm.

[Adhesive Layer]

The polarizing plate of the embodiment of the present invention may have an adhesive layer arranged between the optically anisotropic film in the optical film of the embodiment of the present invention and the polarizer.

The adhesive layer used for the lamination of the optically anisotropic film and the polarizer represents, for example, a substance in which a ratio (tan δ=G"/G') between a storage elastic modulus G' and a loss elastic modulus G", each measured with a dynamic viscoelastometer, is 0.001 to 1.5, and examples thereof include a so-called adhesive or readily creepable substance. Examples of the adhesive that can be used in the present invention include a polyvinyl alcohol-based adhesive may be used, but the adhesive is not limited thereto.

[Image Display Device]

An image display device of an embodiment of the present invention is an image display device having the optical film of the embodiment of the present invention or the polarizing plate of the embodiment of the present invention.

The display element used in the image display device of the embodiment of the present invention is not particularly limited, and examples thereof include a liquid crystal cell, an organic electroluminescent (hereinafter abbreviated as "EL") display panel, and a plasma display panel.

Among those, the liquid crystal cell and the organic EL display panel are preferable, and the liquid crystal cell is more preferable. That is, as the image display device of the embodiment of the present invention, a liquid crystal display device using a liquid crystal cell as a display element or an organic EL display device using an organic EL display panel as a display element is preferable, and the liquid crystal display device is more preferable.

[Liquid Crystal Display Device]

A liquid crystal display device that is an example of the image display device of the embodiment of the present invention is a liquid crystal display device having the above-mentioned polarizing plate of the embodiment of the present invention and a liquid crystal cell.

Furthermore, in the present invention, it is preferable that the polarizing plate of the embodiment of the present invention is used as the polarizing plate of the front side, out of the polarizing plates provided on the both sides of the liquid crystal cell, and it is more preferable that the polarizing plate of the embodiment of the present invention is used as the polarizing plates on the front and rear sides.

Hereinafter, the liquid crystal cell constituting the liquid crystal display device will be described in detail.

<Liquid Crystal Cell>

A liquid crystal cell for use in the liquid crystal display device is preferably in a vertical alignment (VA) mode, an optically compensated bend (OCB) mode, an in-plane-switching (IPS) mode, or a twisted nematic (TN) mode, but is not limited thereto.

In the liquid crystal cell in a TN mode, rod-like liquid crystal molecules are aligned substantially horizontally in a case where no voltage is applied and are further aligned in a twisted manner in a range of 60º to 120º. The liquid crystal cell in a TN mode is most often used in a color TFT liquid crystal display device and described in many literatures.

In the liquid crystal cell in a VA mode, rod-like liquid crystal molecules are aligned substantially vertically in a case where no voltage is applied. Examples of the liquid crystal cells in a VA mode include (1) a narrowly defined VA mode liquid crystal cell (described in JP1990-176625A (JP-H02-176625A)) in which rod-like liquid crystal molecules are aligned substantially vertically in a case where no voltage is applied and are aligned substantially horizontally in a case where a voltage is applied, (2) a multi-domain VA mode (MVA mode) liquid crystal cell for enlarging the viewing angle (SID97, described in Digest of tech. Papers (Proceedings) 28 (1997) 845), (3) a liquid crystal cell in a mode (n-ASM mode) in which rod-like liquid crystal molecules are aligned substantially vertically in a case where no voltage is applied and are aligned in twisted multi-domain alignment in a case where a voltage is applied (Proceedings of Japanese Liquid Crystal Conference, 58 and 59 (1998)), and (4) a liquid crystal cell in a SURVIVAL mode (presented in LCD International 98). Further, the liquid crystal cell may be of any of a patterned vertical alignment (PVA) type, an optical alignment type, and a polymer-sustained alignment (PSA) type. Details of these modes are described in detail in JP2006-215326A and JP2008-538819A.

In the liquid crystal cell in an IPS mode, rod-like liquid crystal molecules are aligned substantially parallel with respect to a substrate and application of an electric field parallel to the substrate surface causes the liquid crystal molecules to respond planarly. The IPS mode displays black in a case where no electric field is applied and a pair of upper and lower polarizing plates have absorption axes which are orthogonal to each other. A method of improving the viewing angle by reducing light leakage during black display in an oblique direction using an optical compensation sheet is disclosed in JP1998-054982A (JP-H10-054982A), JP1999-202323A (JP-H11-202323A), JP1997-292522A (JP-H09-292522A), JP1999-133408A (JP-H11-133408A), JP1999-305217A (JP-H11-305217A), JP1998-307291A (JP-H10-307291A), and the like.

[Organic EL Display Device]

Suitable examples of the organic EL display device which is an example of the image display device of the embodiment of the present invention include an aspect which includes, from the visible side, a polarizer, a λ/4 plate (a positive A plate) including the optically anisotropic film of the embodiment of the present invention, and an organic EL display panel in this order.

Furthermore, the organic EL display panel is a display panel configured using an organic EL device in which an organic light emitting layer (organic electroluminescent layer) is sandwiched between electrodes (between a cathode and an anode). The configuration of the organic EL display panel is not particularly limited but any known configuration is adopted.

EXAMPLES

Hereinafter, the present invention will be described in more detail with reference to Examples. The materials, the amounts of materials used, the proportions, the treatment details, the treatment procedure, and the like shown in Examples below may be modified, as appropriate, as long as the modifications do not depart from the spirit of the present invention. Therefore, the scope of the present invention should not be construed as being limited to Examples shown below.

Example 1

Synthesis of Compound (I-1c)

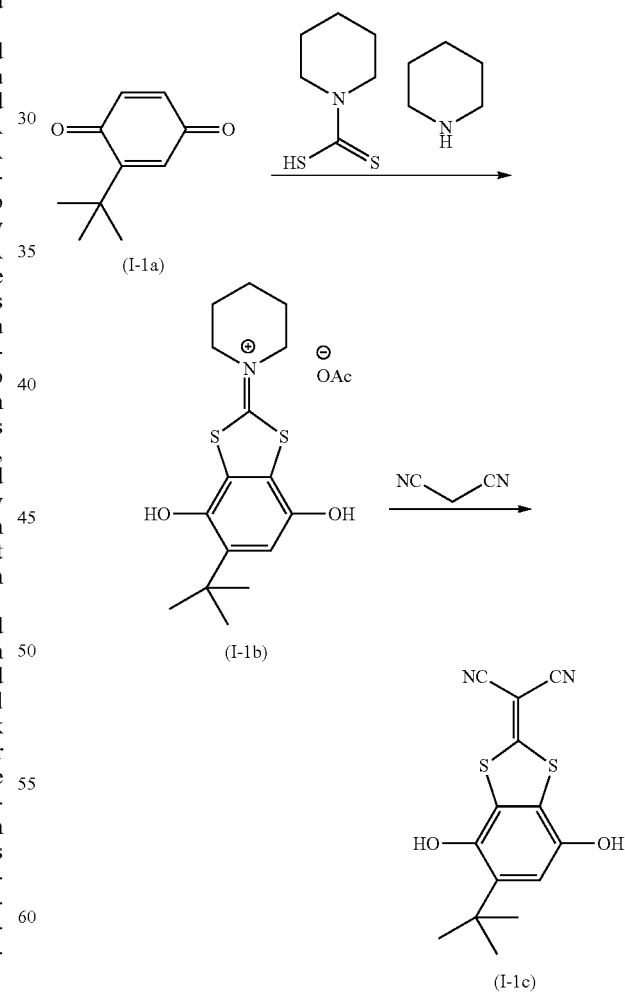

As shown in the scheme, a compound (I-1c) was synthesized according to the method described in paragraph (Example 17) of JP2016-081035A.

Synthesis of Compound (I-1e)

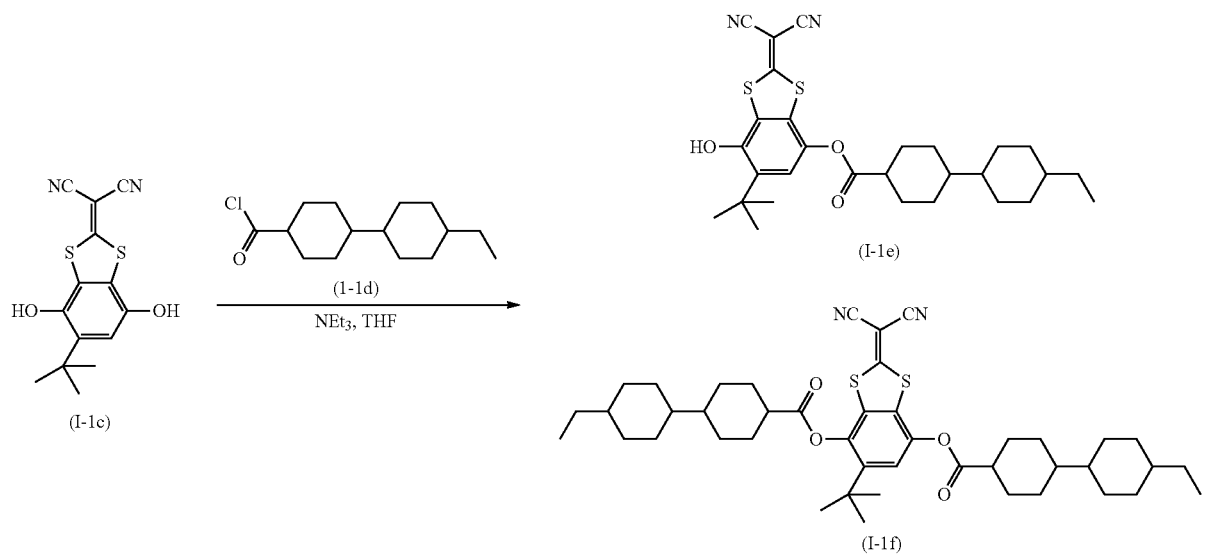 [SMILES: CC(C)(C)c1cc(O)c2c(c1O)SC(=C(C#N)C#N)S2 ; CCC1CCC(C2CCC(C(=O)Cl)CC2)CC1 ; CCC1CCC(C2CCC(C(=O)Oc3cc(C(C)(C)C)c(OC(=O)C4CCC(C5CCC(CC)CC5)CC4)c4c3SC(=C(C#N)C#N)S4)CC2)CC1 ; CCC1CCC(C2CCC(C(=O)Oc3cc(C(C)(C)C)c(O)c4c3SC(=C(C#N)C#N)S4)CC2)CC1]

Subsequently, as shown in the scheme, in a nitrogen atmosphere, 10 g (0.0329 mol) of the compound (I-1c), 3.7 g (0.0361 mol) of triethylamine (NEt₃), and 70 ml of tetrahydrofuran (THF) were mixed, and then a THF solution (20 ml) of 7.6 g of the compound (I-1d) was added dropwise to the mixture at −5° C. or lower for 30 minutes. After stirring the mixture at −5° C. or lower for 30 minutes, 5 ml of methanol, 50 ml of 1 M aqueous hydrochloric acid, and 20 ml of ethyl acetate were added thereto, and the mixture was extracted with ethyl acetate.

The extracted organic layer was washed with 10% physiological saline, the organic layer was dried over magnesium sulfate, and the solvent was evaporated under reduced pressure.

Subsequently, 60 ml of methanol and 20 ml of water were added thereto, and the precipitated solid was filtered to obtain 11.8 g (0.0225 mol) of a compound (I-1e), and a compound (I-1f) (yield 76%).

Furthermore, the ratio of the compound (I-1e) to the compound (I-1f) was measured by means of high performance liquid chromatography, and as a result, it was found to be (I-1e):(I-1f)=96.9:3.1.

Synthesis of Compound (I-1)

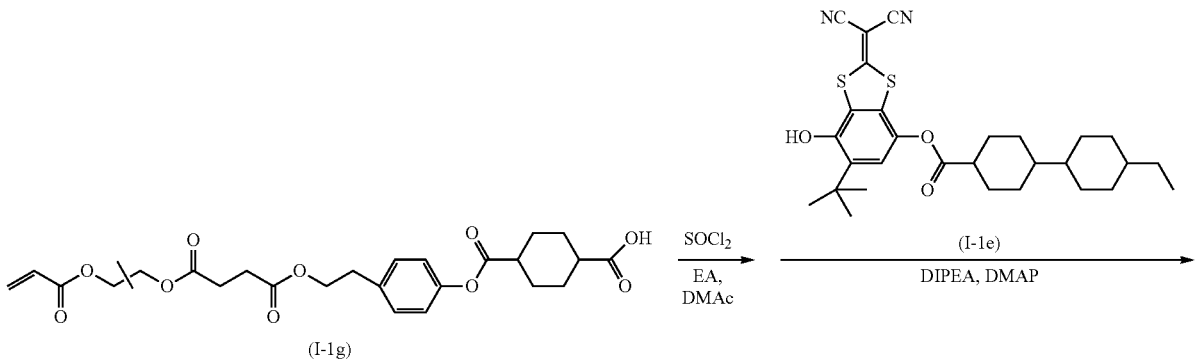

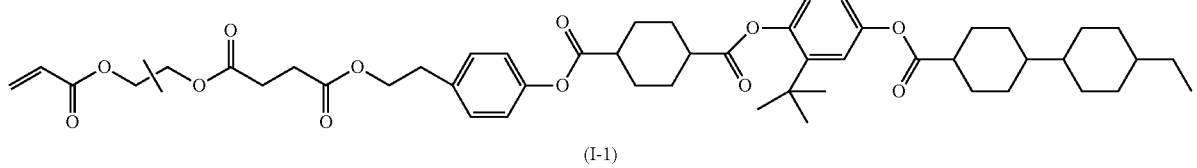

(I-1)

A compound (I-1g) shown in the scheme, that is, the mixture (I-4C) described in paragraph [0122] of JP2016-081035A was synthesized by the method described in paragraphs [0123] to [0125] of the same publication.

Subsequently, as shown by the scheme, 4.62 g (9.15 mmol) of the compound (I-1g), 20 mL of ethyl acetate (EA), 8 mL of N,N-dimethylacetamide (DMAc), and 80 mg of 2,6-di-t-butyl-4-methylphenol were mixed at room temperature, and the inner temperature was lowered to 5° C. To the mixture was added dropwise 1.27 g (10.6 mmol) of thionyl chloride (SOCl$_2$) while the inner temperature was not raised to 10° C. or higher. After stirring the mixture at 5° C. for 1 hour, 4.0 g (7.62 mmol) of the compound (I-1e) and 46 mg (0.38 mmol) of N,N-dimethylaminopyridine (DMAP) were added thereto. 2.46 g (19.1 mmol) of N,N-diisopropylethylamine (DIPEA) was added dropwise thereto, and then the mixture was stirred at room temperature for 6 hours. After stirring, 20 ml of 1 N hydrochloric acid, 20 ml of ethyl acetate, and 20 ml of THF were added thereto to stop the reaction and perform liquid separation. The organic layer was washed with 10% physiological saline and then dried over magnesium sulfate, and the solvent was evaporated under reduced pressure. 40 ml of methanol was added thereto and the precipitated solid was filtered to obtain 6.55 g (6.48 mmol) of a compound (I-1) (yield 85%).

$^1$H-Nuclear Magnetic Resonance (NMR) of the obtained compound (I-1) is shown below.

$^1$H-NMR (solvent: CDCl$_3$) δ (ppm): 0.8-1.3 (m, 19H), 1.3 (s, 9H), 1.7-1.8 (m, 8H), 1.9 (m, 2H), 2.2 (m, 2H), 2.3 (m, 4H), 2.5-2.6 (m, 7H), 2.9 (t, 2H), 4.1-4.3 (m, 4H), 5.2 (m, 1H), 5.8 (dd, 1H), 6.1 (dd, 1H), 6.4 (dd, 1H), 7.0 (d, 2H), 7.3 (m, 3H)

Example 2

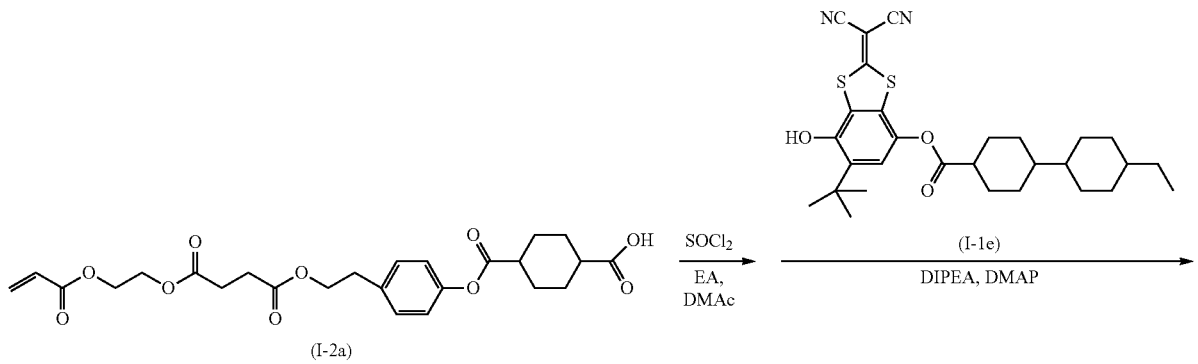

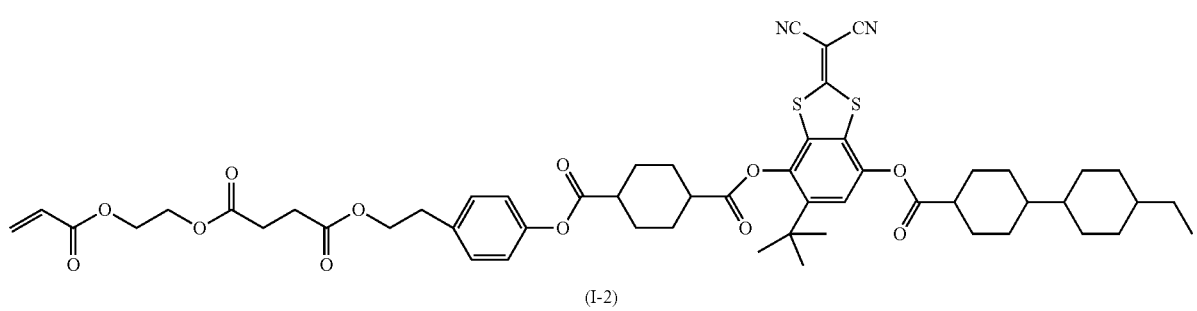

(I-2)

A compound (I-2a) shown in the scheme was synthesized by the method described in paragraph [0109] of JP2016-081035A.

Subsequently, a compound (I-2) was synthesized (yield of 85%) by the same method as for the compound (I-1), except that the compound (I-1g) was changed to the compound (I-2a) in the synthesis method for the compound (I-1), as shown in the scheme.

$^1$H-NMR of the obtained compound (I-2) is shown below.

$^1$H-NMR (solvent: CDCl$_3$) δ (ppm): 0.8-1.3 (m, 16H), 1.4 (s, 9H), 1.5 (m, 2H), 1.7-1.8 (m, 6H), 1.9 (m, 2H), 2.2 (m, 2H), 2.3 (m, 4H), 2.5 (m, 1H), 2.6-2.7 (m, 6H), 2.9 (t, 2H), 4.3-4.4 (m, 6H), 5.9 (dd, 1H), 6.1 (dd, 1H), 6.4 (dd, 1H), 7.0 (d, 2H), 7.2 (d, 2H), 7.3 (s, 1H)

Example 3

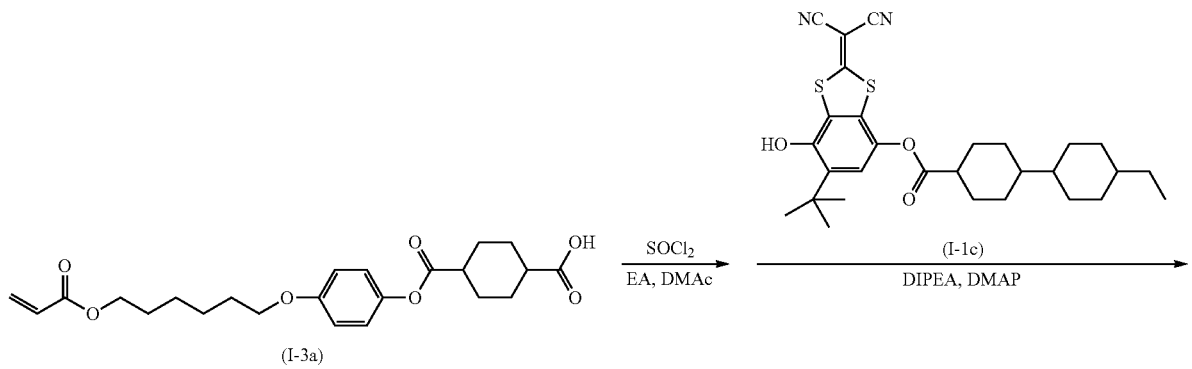

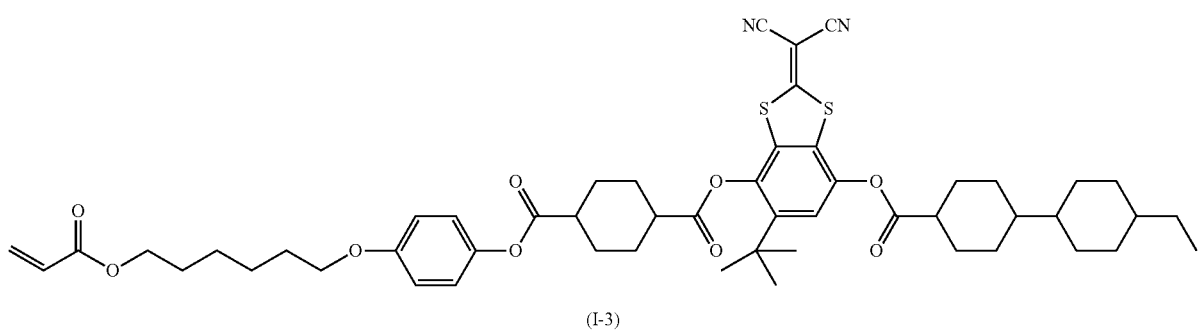

A compound (I-3a) shown in the scheme was synthesized by the method described in paragraph [0392] of JP2010-031223A.

Subsequently, a compound (I-3) was synthesized (yield of 88%) by the same method as for the compound (I-1), except that the compound (I-1g) was changed to the compound (I-3a) in the synthesis method for the compound (I-1), as shown in the scheme.

$^1$H-NMR of the obtained compound (I-3) is shown below.

$^1$H-NMR (solvent: CDCl$_3$) δ (ppm): 0.8-1.3 (m, 16H), 1.3 (s, 9H), 1.4-1.6 (m, 4H), 1.7-1.8 (m, 12H), 1.9 (m, 2H), 2.2 (m, 2H), 2.3 (m, 4H), 2.5-2.7 (m, 3H), 3.9 (t, 2H), 4.2 (t, 2H), 5.8 (dd, 1H), 6.1 (dd, 1H), 6.4 (dd, 1H), 6.9 (d, 2H), 7.0 (d, 2H), 7.3 (s, 1H)

Example 4

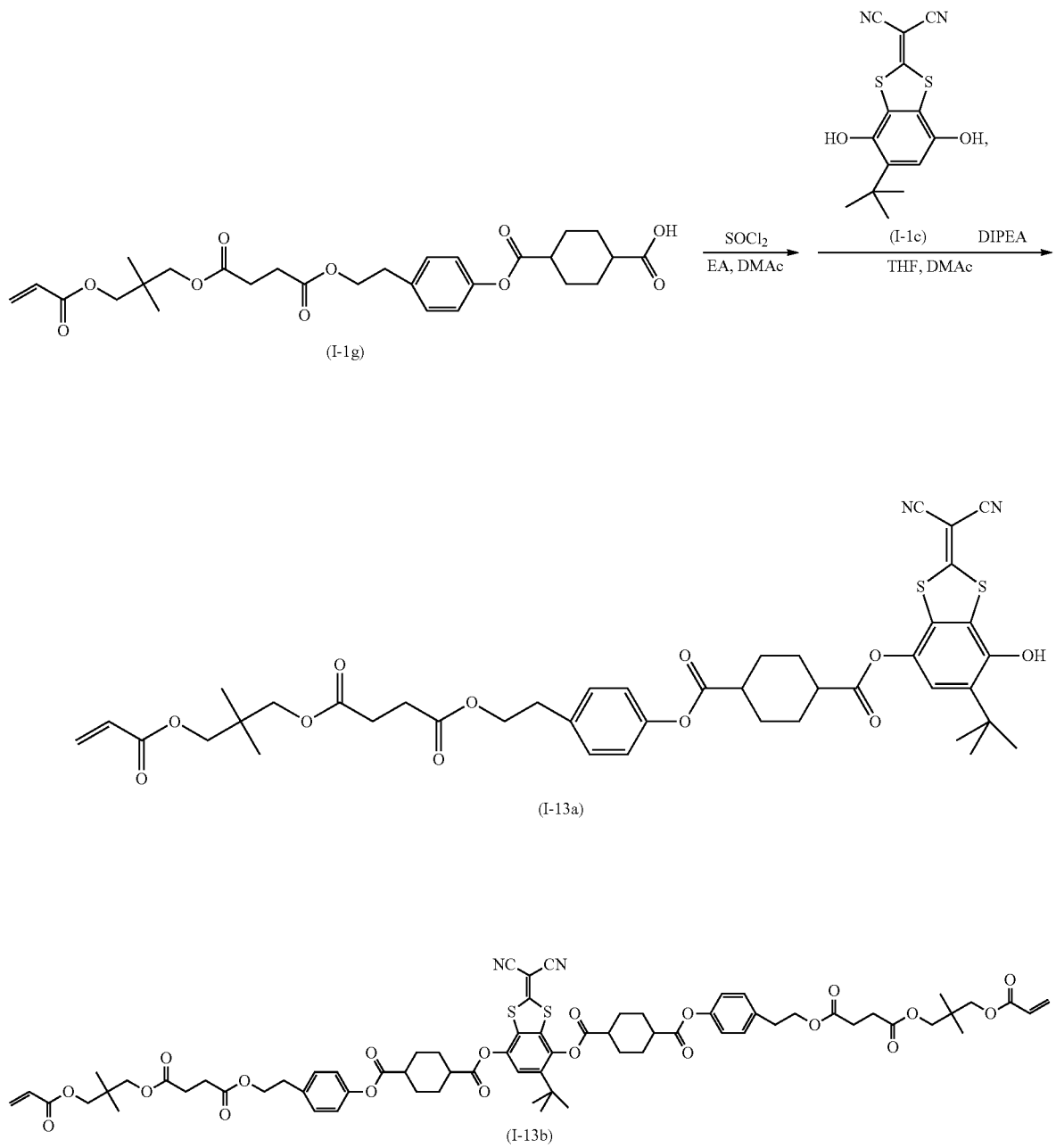

As shown in the scheme, 3.01 g (5.97 mmol) of the compound (I-1g), 15 mL of ethyl acetate (EA), 4.5 mL of N,N-dimethylacetamide (DMAc), and 65 mg of 2,6-di-t-butyl-4-methylphenol were mixed at room temperature, and the inner temperature was lowered to 5° C. To the mixture was added dropwise 0.52 ml (7.17 mmol) of thionyl chloride (SOCl$_2$) while the inner temperature was adjusted not to be 10° C. or higher. After stirring the mixture at 5° C. for 1 hour, a THF solution (8 ml) of 2.0 g (6.57 mmol) of the compound (I-1c) was added dropwise thereto. 2.6 ml (14.9 mmol) of N,N-diisopropylethylamine (DIPEA) was added dropwise thereto while the inner temperature was adjusted not to be higher than −5° C., and then the mixture was stirred at −5° C. or lower for 30 minutes. After stirring, 10 ml of 1 N hydrochloric acid and 10 ml of ethyl acetate were added thereto to stop the reaction and perform liquid separation. The organic layer was washed with 10% physiological saline and then dried over magnesium sulfate, and the solvent was evaporated under reduced pressure.

The ratio of the obtained crude compound (I-13a) to the obtained crude compound (I-13b) was measured by means of high performance liquid chromatography, and as a result, it was found to be (I-13a):(I-13b)=97:3. The obtained crude products were purified by silica gel column chromatography to obtain 2.83 g (3.58 mmol) of a compound (I-13a) (yield of 65%).

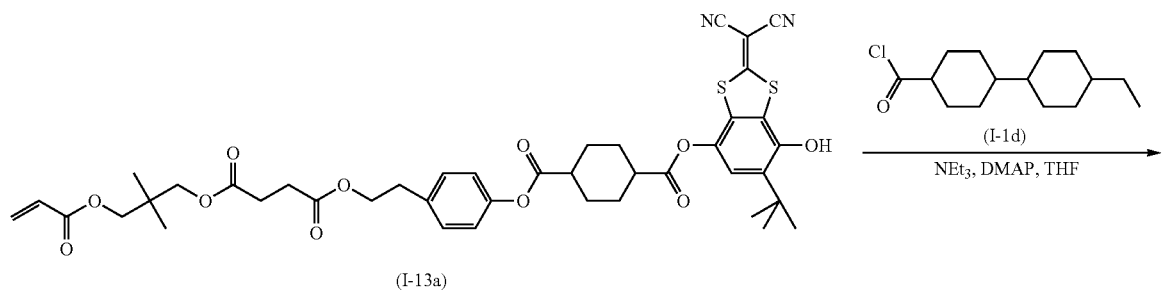

(I-13a)

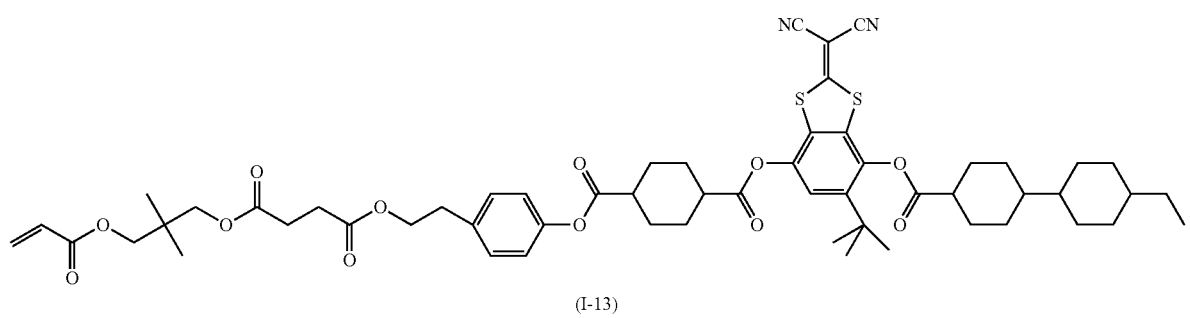

(I-13)

As shown in the scheme, 2.47 g (3.13 mmol) of the compound (I-13a), 0.88 g (3.44 mmol) of the compound (I-1d), 38 mg (0.32 mmol) of N,N-dimethylaminopyridine (DMAP), 40 mg of 2,6-di-t-butyl-4-methylphenol, and THF (15 ml) were mixed, and then 0.53 ml (3.76 mmol) of triethylamine (NEt₃) was added dropwise thereto under ice cooling. After stirring the mixture at room temperature for 4 hours, 20 ml of 1 M aqueous hydrochloric acid and 15 ml of ethyl acetate were added thereto, and the mixture was extracted with ethyl acetate. The organic layer was washed with 10% physiological saline and then dried over magnesium sulfate, and the solvent was evaporated under reduced pressure. 40 ml of methanol was added thereto and the precipitated solid was filtered to obtain 2.53 g (2.50 mmol) of a compound (I-13) (yield of 80%).

The ¹H-NMR of the obtained compound (I-13) is shown below.

¹H-NMR (solvent: CDCl₃) δ (ppm): 0.8-1.3 (m, 19H), 1.3 (s, 9H), 1.7-1.8 (m, 8H), 1.9 (m, 2H), 2.2 (m, 2H), 2.3 (m, 4H), 2.5-2.6 (m, 7H), 2.9 (t, 2H), 4.1-4.3 (m, 4H), 5.2 (m, 1H), 5.8 (dd, 1H), 6.1 (dd, 1H), 6.4 (dd, 1H), 7.0 (d, 2H), 7.3 (m, 3H)

Example 5

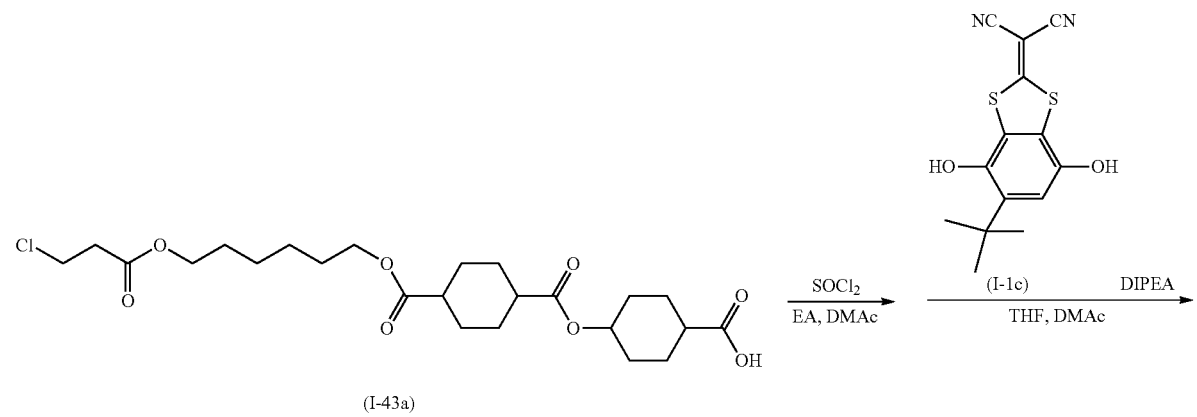

(I-43a)

-continued
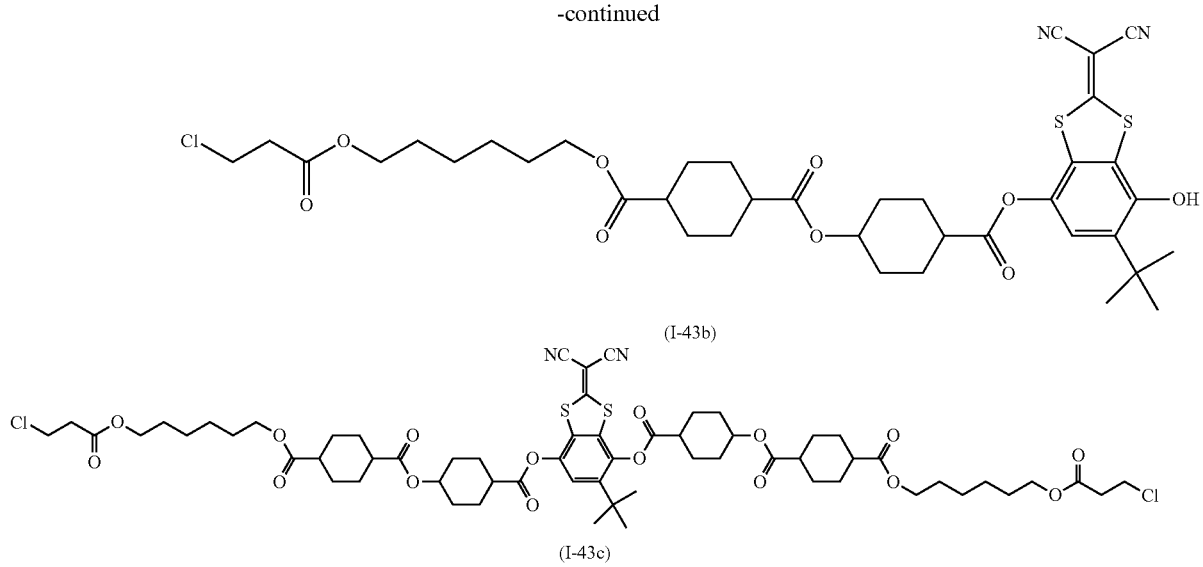
(I-43b)
(I-43c)
A compound (I-43a) shown in the scheme was synthesized by the method described in paragraphs [0128] to [0132] of JP2009-179563A. The compound (I-43b) was synthesized (yield of 72%) by the same method as for the compound (I-13a), except that the compound (I-1g) was changed to the compound (I-43a) in the synthesis method for the compound (I-13a), as shown in the scheme.
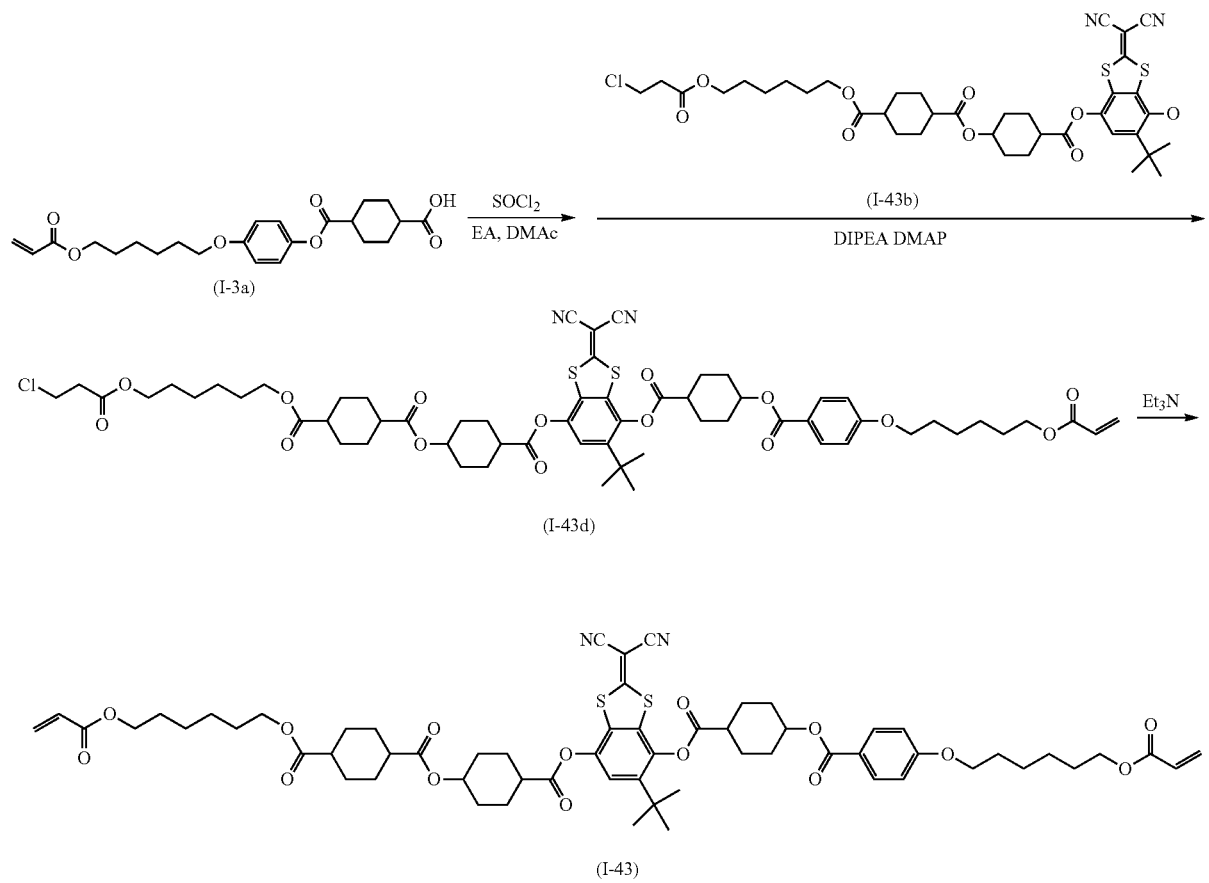

Subsequently, a compound (I-43d) was synthesized by the same method as for the compound (I-1), except that the compound (I-1g) was changed to the compound (I-3a) and the compound (I-1e) was changed to the compound (I-43b) in the synthesis method for the compound (I-1), as shown in the scheme.

Purification was not performed, 0.90 g (0.77 mmol) of a crude product of the compound (I-43d), 5 mL of acetonitrile, and 10 mg of 2,6-di-t-butyl-4-methylphenol were mixed at room temperature, 0.21 ml (1.51 mmol) of triethylamine was added to the mixture, and then the mixture was stirred under heating for 2 hours while the reaction temperature was warmed to 50° C. After completion of the reaction, the mixture was cooled to room temperature, and then 10 ml of 1 N hydrochloric acid and 10 ml of ethyl acetate were added thereto to stop the reaction and perform liquid separation. The organic layer was washed with 10% physiological saline and then dried over magnesium sulfate, and the solvent was evaporated under reduced pressure. The obtained crude product was purified by silica gel column chromatography to obtain 0.69 g (0.61 mmol) of a compound (I-43) (yield of 71%).

$^1$H-NMR of the obtained compound (I-43) is shown below.

$^1$H-NMR (solvent: $CDCl_3$) δ (ppm): 1.3 (s, 9H), 1.3-1.8 (m, 30H), 2.1-2.4 (m, 13H), 2.6-2.7 (m, 3H), 3.9 (t, 2H), 4.1 (t, 2H), 4.2 (m, 4H), 4.8 (m, 1H), 5.8 (dd, 2H), 6.1 (dd, 2H), 6.4 (d, 2H), 6.9 (d, 2H), 7.0 (d, 2H), 7.3 (s, 1H)

Comparative Example 1

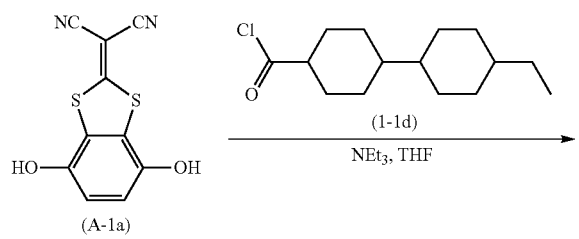
(A-1a)                 (1-1d)
                       NEt$_3$, THF

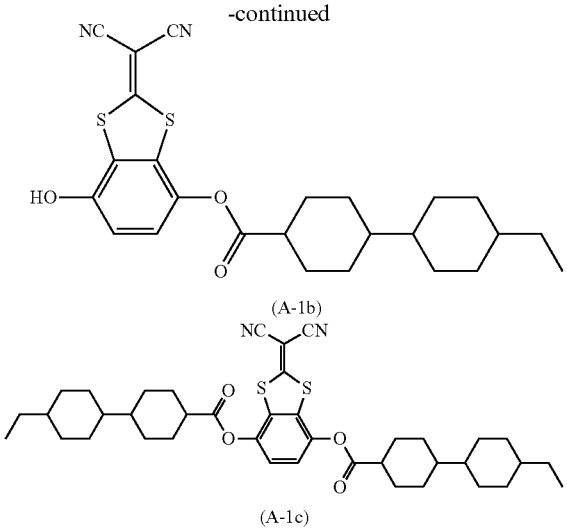
(A-1b)

(A-1c)

As shown in the scheme, in a nitrogen atmosphere, 8.2 g (0.0329 mol) of a compound (A-1a), 3.7 g (0.0361 mol) of triethylamine (NEt$_3$), and THF (70 ml) were mixed, and then a THF solution (20 ml) of 7.6 g (0.0296 mol) of the compound (I-1d) was added dropwise thereto at −5° C. or lower for 30 minutes. After stirring the mixture at −5° C. or lower for 30 minutes, 5 ml of methanol, 50 ml of 1 M aqueous hydrochloric acid, and 20 ml of ethyl acetate were added thereto, and the mixture was extracted with ethyl acetate. The organic layer was washed with 10% physiological saline and then dried over magnesium sulfate and the solvent was evaporated under reduced pressure. 60 ml of methanol and 20 ml of water were added thereto, and the precipitated solid was filtered to obtain a mixture of compounds (A-1a), (A-1b), and (A-1c).

The ratio of the compound (A-1a) to the compound (A-1b) to the compound (A-1c) was measured by high performance liquid chromatography, and as a result, it was found to be (A-1a):(A-1b):(A-1c)=33.1:47.9:19.0. The crude product was purified by silica gel column chromatography to isolate the compound (A-1b) (yield of 38%).

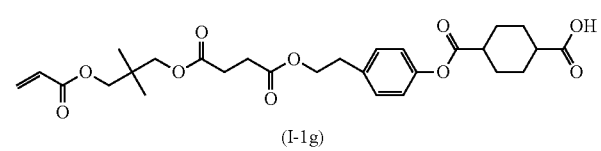
(I-1g)

SOCl$_2$
EA, DMAc

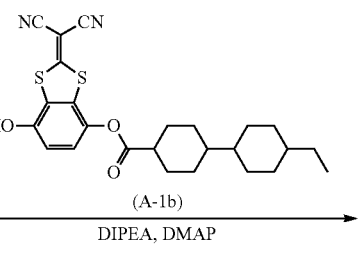
(A-1b)
DIPEA, DMAP

-continued

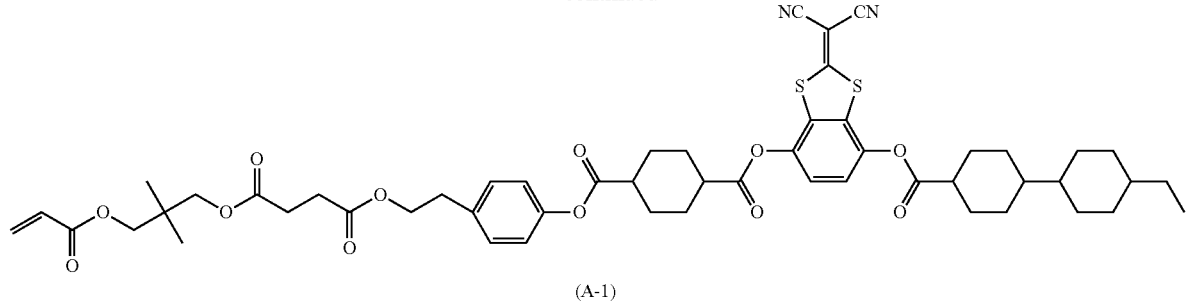

(A-1)

Subsequently, a compound (A-1) was synthesized (yield of 87%) by the same method as for the compound (I-1), except that the compound (I-1e) was changed to a compound (A-1b) in the synthesis method for the compound (I-1), as shown in the scheme.

Comparative Example 2

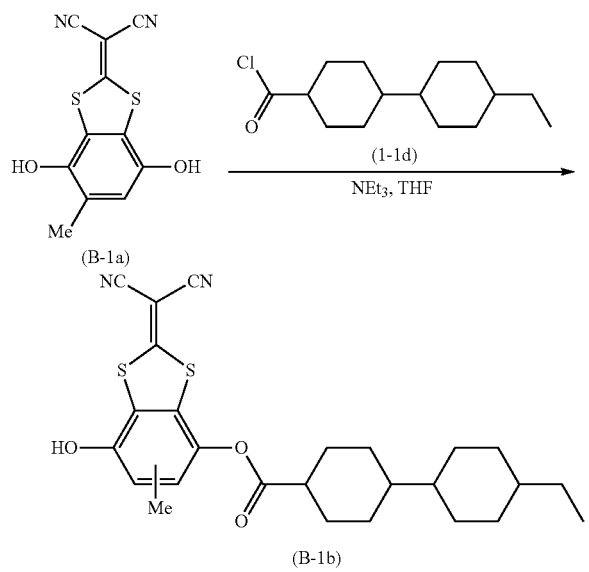

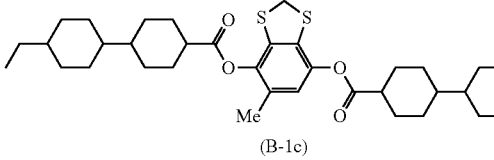

As shown in the scheme, in a nitrogen atmosphere, 8.6 g (0.0329 mol) of a compound (B-1a), 3.7 g (0.0361 mol) of triethylamine (NEt$_3$), and THF (70 ml) were mixed, and then a THF solution (20 ml) of 7.6 g of the compound (I-1d) was added dropwise thereto at −5° C. or lower for 30 minutes. After stirring the mixture at −5° C. or lower for 30 minutes, 5 ml of methanol, 50 ml of 1 M aqueous hydrochloric acid, and 20 ml of ethyl acetate were added thereto and the mixture was extracted with ethyl acetate. The organic layer was washed with 10% physiological saline and then dried over magnesium sulfate, and the solvent was evaporated under reduced pressure. 60 ml of methanol and 20 ml of water were added thereto, and the precipitated solid was filtered to obtain a mixture of compounds (B-1a), (B-1b), and (B-1c). The ratio of (B-1a):(B-1b):(B-1c) was measured by high performance liquid chromatography, and as a result, it was found to be (B-1a):(B-1b):(B-1c)=34.4:48.2:17.4. The crude product was purified by silica gel column chromatography to isolate the compound (B-1b) (yield of 39%).

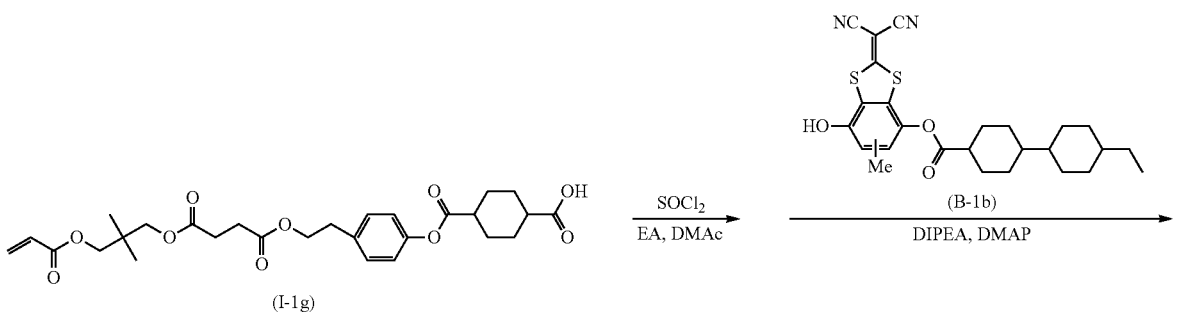

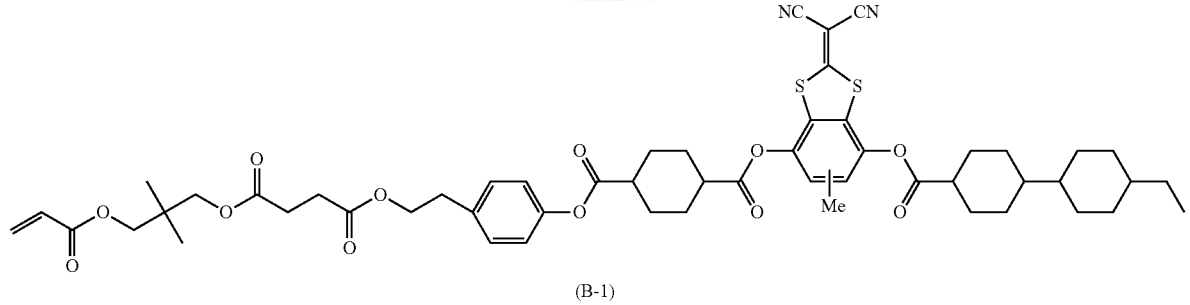

(B-1)

Subsequently, a compound (B-1) was synthesized (yield of 85%) by the same method as for the compound (I-1), except that the compound (I-1e) was changed to the compound (B-1b) in the synthesis method for the compound (I-1), as shown in the scheme.

Comparative Example 3

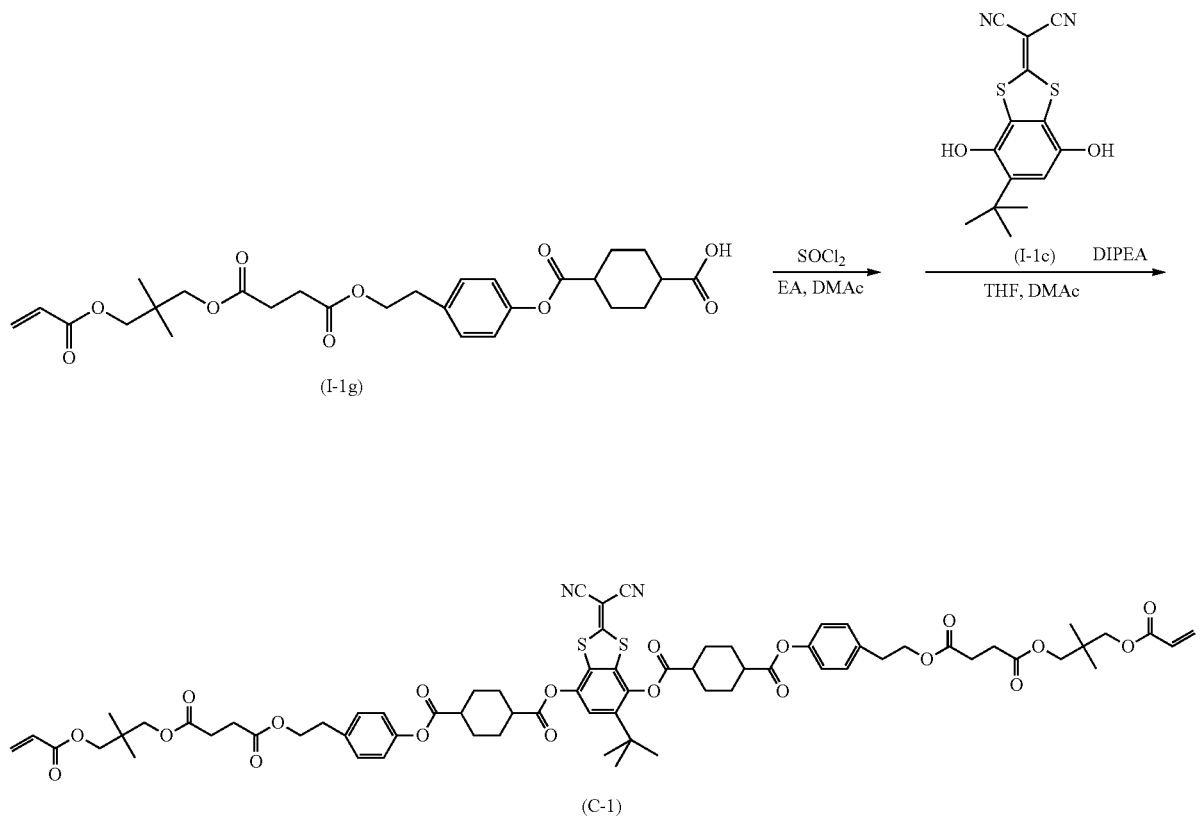

As shown in the scheme, 3.01 g (5.97 mmol) of the compound (I-1g), 15 mL of ethyl acetate (EA), 4.5 mL of N,N-dimethylacetamide (DMAc), and 65 mg of 2,6-di-t-butyl-4-methylphenol were mixed at room temperature, and the inner temperature was lowered to 5° C. To the mixture was added dropwise 0.52 ml (7.17 mmol) of thionyl chloride (SOCl$_2$) while the inner temperature was adjusted not to be 10° C. or higher. After stirring the mixture at 5° C. for 1 hour, a THF solution (5 ml) of 0.826 g (2.71 mmol) of the compound (I-1c) and 16.6 mg (0.136 mmol) and N,N-dimethylaminopyridine were added thereto. 2.6 ml (14.9 mmol) of N,N-diisopropylethylamine (DIPEA) was added dropwise thereto, and then the mixture was stirred at room temperature for 6 hours. After stirring, 10 ml of 1 N hydrochloric acid and 10 ml of ethyl acetate were added thereto to stop the reaction and perform liquid separation. The organic layer was washed with 10% physiological saline and then dried over magnesium sulfate, and the solvent was evaporated under reduced pressure. The obtained crude products were purified by silica gel column chromatography to obtain 2.25 g (1.76 mmol) of a compound (C-1) (yield of 65%).

Comparative Example 4
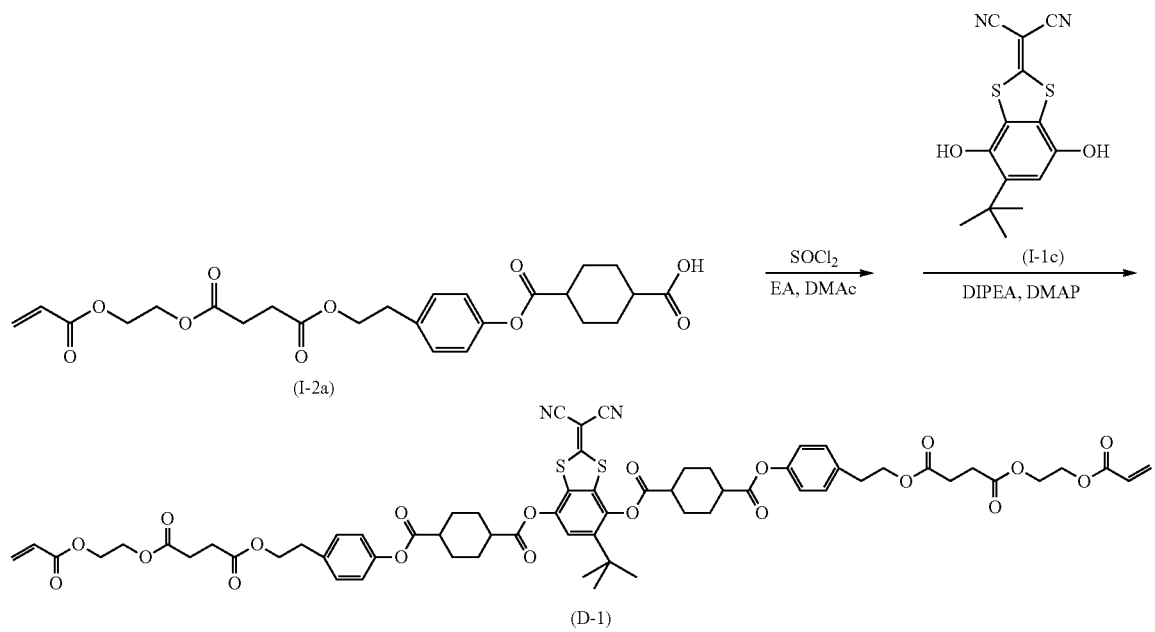
As shown in the scheme, a compound (D-1) was synthesized (yield of 64%) was synthesized by the same method as for the compound (C-1), except that the compound (I-1g) was changed to the compound (I-2a) in the synthesis method for the compound (C-1).
Comparative Example 5
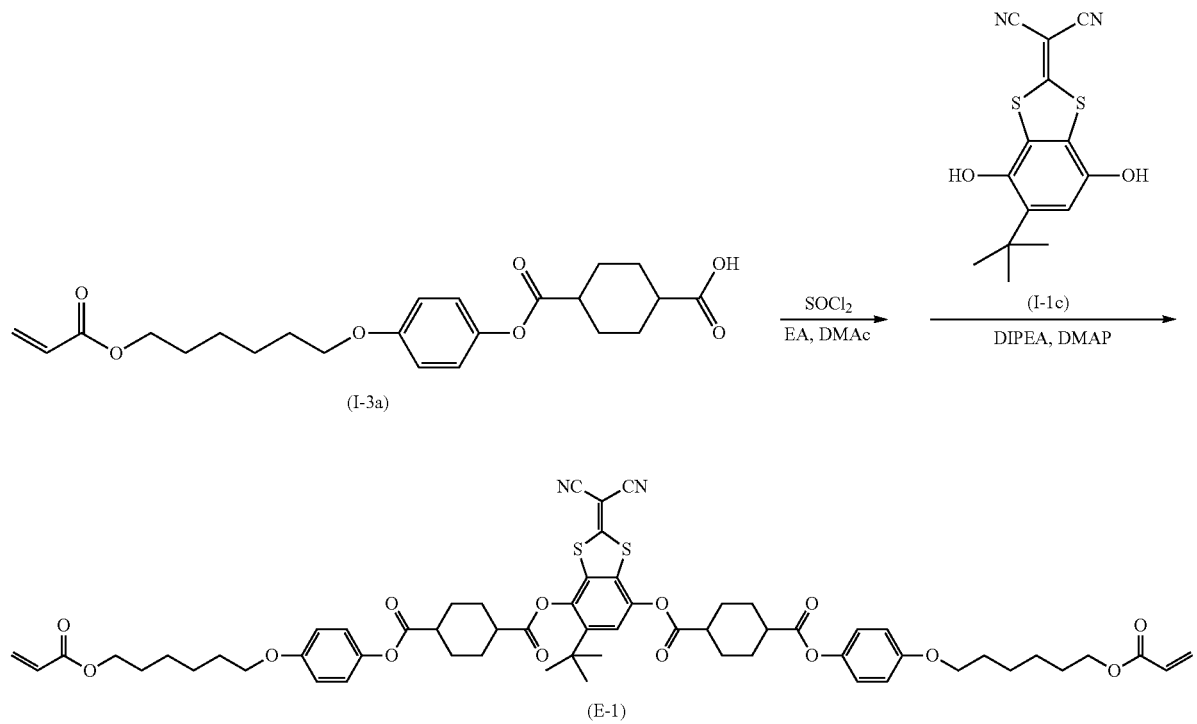

As shown in the scheme, 2.50 g (5.97 mmol) of the compound (I-3a), 15 mL of ethyl acetate (EA), 4.5 mL of N,N-dimethylacetamide (DMAc), and 65 mg of 2,6-di-t-butyl-4-methylphenol were mixed at room temperature, and the inner temperature was lowered to 5° C. To the mixture was added dropwise 0.52 ml (7.17 mmol) of thionyl chloride (SOCl$_2$) while the inner temperature was adjusted not to be 10° C. or higher. After stirring the mixture at 5° C. for 1 hour, a THF solution (5 ml) of 0.826 g (2.71 mmol) of the compound (I-1c) and 16.6 mg (0.136 mmol) of N,N-dimethylaminopyridine (DMAP) were added thereto. 2.6 ml (14.9 mmol) of N,N-diisopropylethylamine (DIPEA) was added dropwise thereto, and then the mixture was stirred at room temperature for 6 hours. After stirring, 10 ml of 1 N hydrochloric acid and 10 ml of ethyl acetate were added thereto to stop the reaction and perform liquid separation. The organic layer was washed with 10% physiological saline and then dried over magnesium sulfate, and the solvent was evaporated under reduced pressure. 40 ml of methanol was added thereto, and the precipitated solid was filtered to obtain 2.03 g (1.82 mmol) of a compound (E-1) (yield of 67%).

Comparative Example 6

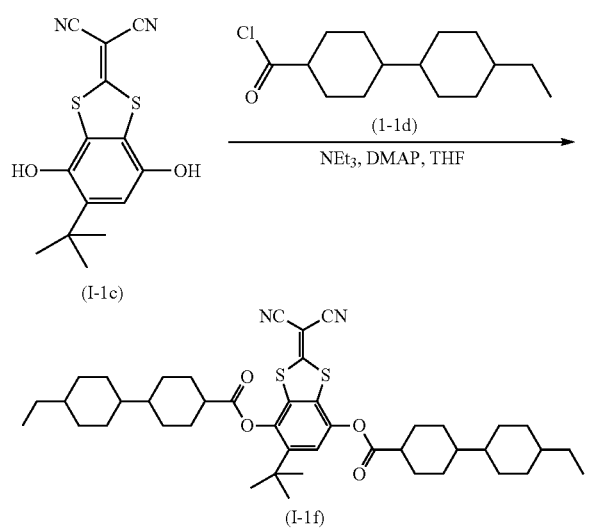

As shown in the scheme, in a nitrogen atmosphere, 1 g (3.29 mmol) of the compound (I-1c), 0.370 g (3.61 mol) of triethylamine (NEt$_3$), 16.6 mg (0.165 mmol) of N,N-dimethylaminopyridine (DMAP), and THF (20 ml) were mixed, and the inner temperature was lowered to 5° C. To the mixture was added dropwise a THF solution (5 ml) of 1.86 g (7.23 mmol) of the compound (I-1d) for 30 minutes, and then the mixture was stirred at room temperature for 6 hours. After stirring, 50 ml of methanol was added thereto, and the precipitated solid was filtered to obtain 1.47 g (1.97 mmol) of a compound (I-1f) (yield of 60%).

Synthesis Suitability

The synthesis suitability of the polymerizable liquid crystal compounds synthesized in Examples and Comparative Examples was evaluated based on the following standard. The results are shown in Table 6 below.

A: The yield from the phenol intermediate (referring to any one compound of the compound (I-1c), the compound (A-1a), and the compound (B-1a), which applies in this paragraph) is 50% or more, and column purification is not required.

B: The yield from the phenol intermediate is 50% or more, but column purification is required.

C: The yield from the phenol intermediate is less than 50%.

<Phase Transition Temperature>

The phase transition temperatures of the polymerizable liquid crystal compounds synthesized in Examples and Comparative Examples were measured using a polarization microscope. The results are shown in Table 6 below.

Here, in Table 6 below, "C 100 N 155 I" of Example 1 indicates that a phase transition temperature from a crystalline state to a nematic phase is 100° C. and a phase transition temperature from a nematic phase to an isotropic liquid is 155° C.; the "C 179 (N 144) I" of Example 4 indicates that there is a transition from an isotropic liquid to a nematic phase at 144° C. a temperature lowering process, but liquid crystallinity is not exhibited a temperature rising process and a monotropic liquid crystal with transition from a crystalline state to an isotropic liquid at 179° C. is exhibited; and "<25 I" of Comparative Example 3 indicates an isotropic liquid at 25° C. or lower.

<Solubility>

The solubility of the polymerizable liquid crystal compounds synthesized in Examples and Comparative Examples was measured by the method shown below. The results are shown in Table 6 below.

Specifically, 50 mg of the compound was weighed into a 1.5-mL sample bottle, and a solvent was added thereto until the solid content became 40% by weight (75 mg).

The mixture was thoroughly shaken by the hand at 50° C. and left to stand at room temperature (23° C.) for 10 minutes. Then, this operation was stopped in a case where the mixture was clear upon visual observation, and it was determined that the solubility was 40% by weight. A solvent was added so that the solid content became 35% by weight in a case where there were undissolved residues (+18 mg). The mixture was thoroughly shaken by the hand at 50° C. and left to stand at room temperature (23° C.) for 10 minutes. Then, this operation was stopped in a case where the mixture was clear upon visual observation, and it was determined that the solubility was 35% by weight. A solvent was added so that the solid content became 30% by weight in a case where there were undissolved residues. The same operation was performed in 5%-by-weight steps and repeated up to 5% by weight. In a case where there were undissolved residues, it was determined that the solubility was less than 5% by weight (<5% by weight), and the operation was stopped. Methyl ethyl ketone (MEK) and cyclopentanone (CPN) were used as solvents for solubility measurement.

A: A solubility in any one of MEK or CPN is 30% or more.

B: A solubility in any one of MEK or CPN is 15% or more and less than 30%.

C: A solubility in any one of MEK or CPN is less than 15%.

<Durability>

A polymerizable composition (a coating liquid for an optically anisotropic film) having the following composition was prepared and applied through spin coating onto on a glass substrate having a polyimide alignment film (SE-150 manufactured by Nissan Chemical Industries, Ltd.) which had been subjected to a rubbing treatment. The coated film was subjected to an alignment treatment at a temperature shown in Table 5 below to form a liquid crystal layer. Thereafter, the liquid crystal layer was cooled to an exposure temperature, described in Table 5 below and subjected to alignment fixation by ultraviolet irradiation of 1,000 mJ/cm² to form an optically anisotropic film, thereby obtaining an optical film for wavelength dispersion measurement.

In addition, since in Comparative Example 3, there was alignment failure and in Comparative Example 6, crystals precipitated, whereby it was not possible to obtain an optical film.

| Optical film isotropic layer film coating liquid | |
|---|---|
| Polymerizable liquid crystal compound (compound described in Table 6 below) | 15.00 parts by mass |
| Photopolymerization initiator (IRGACURE 819, manufactured by BASF) | 0.45 parts by mass |
| Fluorine-containing compound A below | 0.12 parts by mass |
| Chloroform | 35.00 parts by mass |

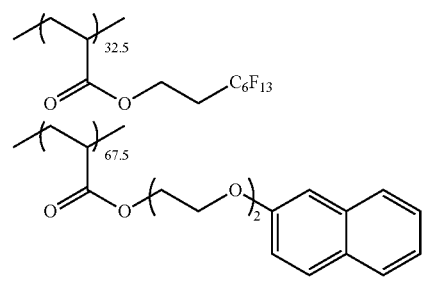

Fluorine-containing compound A

With regard to the prepared optical film, a retardation value (Re (450)) at a wavelength of 450 nm and a retardation value (Re (550)) at a wavelength of 550 nm were measured using an automatic birefringence meter (KOBRA-21ADH, manufactured by Oji Scientific Instruments Co., Ltd.), and Re (450)/Re (550) was calculated. The results are shown in Table 5 below.

TABLE 5

| | Polymerizable liquid crystal compound | Alignment treatment temperature (° C.) | Exposure temperature (° C.) | Re (450) | Re (550) | Re (450)/ Re (550) |
|---|---|---|---|---|---|---|
| Example 1 | I-1 | 157 | 113 | 85 | 113 | 0.75 |
| Example 2 | I-2 | 155 | 113 | 91 | 121 | 0.75 |
| Example 3 | I-3 | 182 | 113 | 110 | 143 | 0.77 |
| Example 4 | 1-13 | 131 | 113 | 112 | 151 | 0.74 |
| Example 5 | 1-43 | 131 | 100 | 97 | 120 | 0.81 |
| Comparative Example 1 | A-1 | 200 | 150 | 102 | 143 | 0.71 |
| Comparative Example 2 | B-1 | 200 | 150 | 96 | 132 | 0.73 |
| Comparative Example 4 | D-1 | 60 | 50 | 73 | 86 | 0.85 |
| Comparative Example 5 | E-1 | 180 | 140 | 123 | 145 | 0.85 |

With regard to a test condition for durability, a test in which the film was left to stand for 144 hours in an environment of a relative humidity of 95% at 100° C. was performed as described in Table 6 below.

A: A variation in Re (550) after the test with respect to the initial retardation value is less than 15% of the initial value.

B: A variation in Re (550) after the test with respect to the initial retardation value is 15% or more and less than 30% of the initial value.

C: A variation in Re (550) after the test with respect to the initial retardation value is 30% or more.

TABLE 6

| Compound No. | Z¹ | X Group OR¹ = | ClogP value | Y Group OR² = | ClogP value |
|---|---|---|---|---|---|
| Example 1 | I-1 | tBu | [structure] | 0.156 | [structure] | 5.189 |
| Example 2 | I-2 | tBu | [structure] | 2.847 | [structure] | 5.189 |

TABLE 6-continued

| | | | Structure 1 | ClogP 1 | Structure 2 | ClogP 2 |
|---|---|---|---|---|---|---|
| Example 3 | I-3 | tBu | 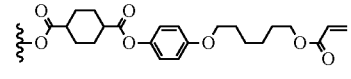 [SMILES: *OC(=O)C1CCC(C(=O)Oc2ccc(OCCCCCCOC(=O)C=C)cc2)CC1] | 4.057 | 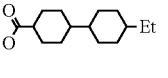 | 5.189 |
| Example 4 | I-13 | tBu | 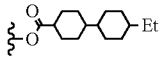 | 5.189 | 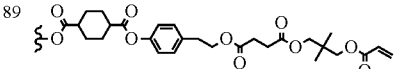 | 3.156 |
| Example 5 | I-43 | tBu | 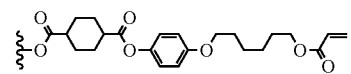 [SMILES: *OC(=O)C1CCC(C(=O)Oc2ccc(OCCCCCCOC(=O)C=C)cc2)CC1] | 4.057 | 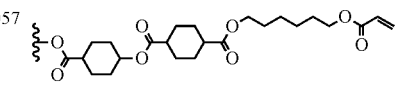 | 3.559 |
| Comparative Example 1 | A-1 | H | 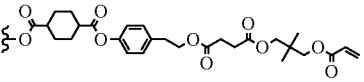 [SMILES: *OC(=O)C1CCC(C(=O)Oc2ccc(CCOC(=O)CCC(=O)OCC(C)(C)COC(=O)C=C)cc2)CC1] | 3.156 | 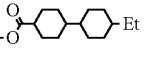 | 5.189 |
| Comparative Example 2 | B-1 | Me | 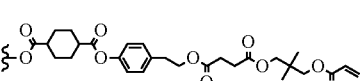 | 3.156 | 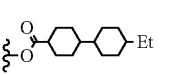 | 5.189 |
| Comparative Example 3 | C-1 | tBu | 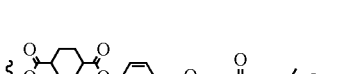 | 3.156 |  | 3.156 |
| Comparative Example 4 | D-1 | tBu |  | 2.847 |  | 2.847 |
| Comparative Example 5 | E-1 | tBu |  | 4.057 |  | 4.057 |
| Comparative Example 6 | I-1f | tBu | 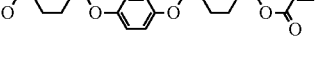 | 5.189 | 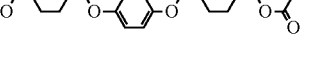 | 5.189 |

| | Synthesis suitability | Phase transition temperature | 溶解性 (wt %) | | 100° C. Relatibe 144 hours |
|---|---|---|---|---|---|
| | | | MEK | CPO Evaluation | |
| Example 1 | A | C 100 N 155 I | 40 | 40 A | A |
| Example 2 | A | C 103 N 165 I | 35 | 30 A | A |
| Example 3 | A | C 154 N 210 I | 10 | 20 B | A |
| Example 4 | B | C 110 N 143 I | 5 | 15 B | B |
| Example 5 | B | C 120 N 145 I | 40 | 40 A | A |
| Comparative Example 1 | C | C 138 N 240 I | 1 | 10 C | C |
| Comparative Example 2 | C | C 210 N 235 I | 5 | 15 B | C |
| Comparative Example 3 | B | <25 I | 40 | 40 A | |
| Comparative Example 4 | B | C <30 N 58 I | 40 | 40 A | C |
| Comparative Example 5 | A | C 127 N 178 I | 8 | 10 C | C |
| Comparative Example 6 | A | C 257 N 274 I | <1 | 1 C | |

From the results shown in Table 6, it was found that even in a case where the structures of two groups extending in the long-axis direction from a center at the reverse-wavelength dispersion expressing portion of the polymerizable liquid crystal compound are different from each other, the durability of an optically anisotropic film thus formed was deteriorated in a case where an aromatic ring constituting a reverse-wavelength dispersion expressing portion of the polymerizable liquid crystal compound does not have a sterically hindered group (Comparative Examples 1 and 2).

It was found that even in a case where the structures of two groups extending in the long-axis direction from a center at the reverse-wavelength dispersion expressing portion of the polymerizable liquid crystal compound are the same as each other, it was not possible to form an optically anisotropic film (Comparative Examples 3 and 6) or the durability of an optically anisotropic film thus formed is deteriorate (Comparative Examples 4 and 5) in a case where the aromatic ring constituting the reverse-wavelength dispersion expressing portion of the polymerizable liquid crystal compound has a sterically hindered group.

In contrast, it was found that in a case of using a polymerizable liquid crystal compound in which the C log P value of the group represented by $L^1$-$SP^1$-$A^1$-$D^3$-$G^1$-$D^1$ and the C log P value of the group represented by L²-SP²-A²-D⁴-G²-D² are different from each other and at least one of the C log P values is 3.3 or more in Formula (1), the solubility is excellent and the durability of an optically anisotropic film thus formed also becomes good (Examples 1 to 5).

In addition, from the comparison between Example 1 and Example 4, it was found that the C log P value of the group represented by L²-SP²-A²-D⁴-G²-D² (Y group) is higher than the C log P value of the group represented by L¹-SP¹-A¹-D³-G¹-D¹ (X group) in Formula (1), the durability of an optically anisotropic film thus formed is further improved.

EXPLANATION OF REFERENCES

10 optical film
12 optically anisotropic film
14 alignment film
16 support
18 hard coat layer

What is claimed is:
1. A polymerizable liquid crystal compound represented by Formula (1),

L¹-SP¹-A¹-D³-G¹-D¹-Ar-D²-G²-D⁴-A²-SP²-L² (1)

in Formula (1), the ClogP value of the group represented by L¹-SP¹-A¹-D³-G¹-D¹ and the ClogP value of the group represented by L²-SP²-A²-D⁴-G²-D² are different from each other, and at least one of the ClogP values is 3.3 or more, wherein in Formula (1), D¹, D², D³, and D⁴ each independently represent a single bond, —O—CO—, —C(=S)O—, —CR¹R²—, —CR¹R²—CR³R⁴—, —O—CR¹R²—, —CR¹R²—O—CR³R⁴—, —CO—O—CR¹R²—, —O—CO—CR¹R²—, —CR¹R²—O—CO—CR³R⁴—, —CR¹R²—CO—O—CR³R⁴—, —NR¹—CR²R³—, or —CO—NR¹—, and R¹, R², R³, and R⁴ each independently represent a hydrogen atom, a fluorine atom, or an alkyl group having 1 to 4 carbon atoms, G¹ and G² each independently represent a divalent alicyclic hydrocarbon group having 5 to 8 carbon atoms, which may have a substituent, and one or more of —CH₂-'s constituting the alicyclic hydrocarbon group may be substituted with —O—, —S—, or —NH—, A¹ and A² each independently represent an aromatic ring having 6 or more carbon atoms, which may have a substituent, or a cycloalkane ring having 6 or more carbon atoms, which may have a substituent, SP¹ and SP² each independently represent a single bond, a linear or branched alkylene group having 1 to 12 carbon atoms, or a divalent linking group in which one or more of —CH₂-'s constituting the linear or branched alkylene group having 1 to 12 carbon atoms are substituted with —O—, —S—, —NH—, —N(Q)-, or —CO—, and Q represents a substituent, L¹ and L² each independently represent a monovalent organic group, and at least one of L¹ or L² represents a polymerizable group, provided that in a case where Ar is an aromatic ring represented by Formula (Ar-4), at least one of L¹, L², or L³ or L⁴ in Formula (Ar-4) represents a polymerizable group, and Ar represents any one aromatic ring selected from the group consisting of groups represented by Formulae (Ar-1) to (Ar-8),

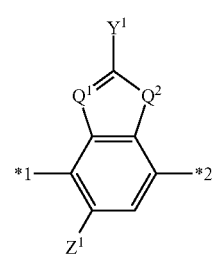
(Ar-1)

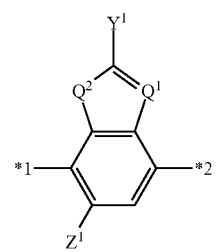
(Ar-2)

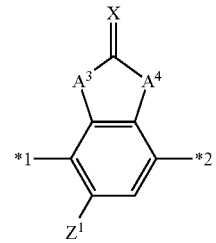
(Ar-3)

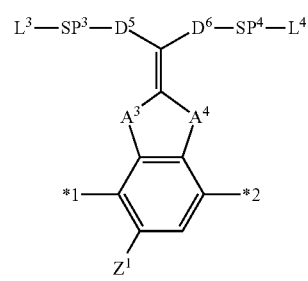
(Ar-4)

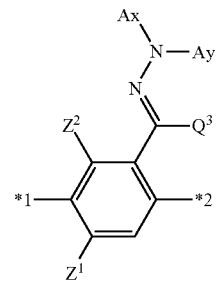
(Ar-5)

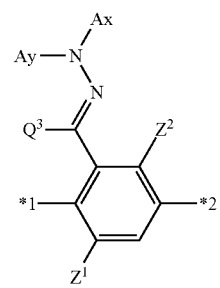
(Ar-6)

-continued

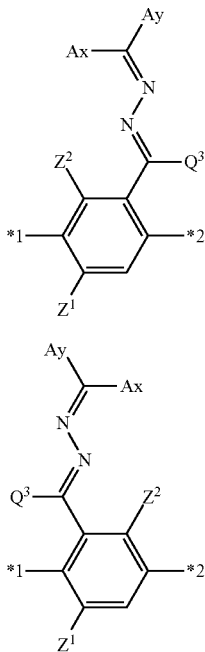

(Ar-7)

(Ar-8)

in Formulae (Ar-1) to (Ar-8), *1 represents a bonding position with $D^1$ and *2 represents a bonding position with $D^2$, $Q^1$ represents N or CH, $Q^2$ represents —S—, —O—, or —N($R^5$)—, and $R^5$ represents a hydrogen atom or an alkyl group having 1 to 6 carbon atoms, $Y^1$ represents an aromatic hydrocarbon group having 6 to 12 carbon atoms or an aromatic heterocyclic group having 3 to 12 carbon atoms, each of which may have a substituent, $Z^1$ represents a monovalent aliphatic hydrocarbon group having 3 to 20 carbon atoms, a monovalent aromatic hydrocarbon group having 6 to 20 carbon atoms, a halogen atom, —$OR^6$, —$NR^7R^8$, or —$SR^9$, and $R^6$ to $R^9$ each independently represent a monovalent aliphatic hydrocarbon group having 3 to 20 carbon atoms or a monovalent aromatic hydrocarbon group having 6 to 20 carbon atoms, $Z^2$ represents a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$OR^{10}$, —$NR^{11}R^{12}$, or —$SR^{13}$, and $R^{10}$ to $R^{13}$ each independently represent a hydrogen atom or an alkyl group having 1 to 6 carbon atoms, $A^3$ and $A^4$ each independently represent a group selected from the group consisting of —O—, —N($R^{14}$)—, —S—, and —CO—, and $R^{14}$ represents a hydrogen atom or a substituent, X represents a non-metal atom of Groups 14 to 16 to which a hydrogen atom or a substituent may be bonded, $D^5$ and $D^6$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO— O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $SP^3$ and $SP^4$ each independently represent a single bond, a linear or branched alkylene group having 1 to 12 carbon atoms, or a divalent linking group in which one or more of —$CH_2$-'s constituting the linear or branched alkylene group having 1 to 12 carbon atoms are substituted with —O—, —S—, —NH—, —N(Q)-, or —CO—, and Q represents a substituent, $L^3$ and $L^4$ each independently represent a monovalent organic group, and at least one of $L^3$, $L^4$, or $L^1$ or $L^2$ in Formula (1) represents a polymerizable group, Ax represents an organic group having 2 to 30 carbon atoms, which has at least one aromatic ring selected from the group consisting of an aromatic hydrocarbon ring and an aromatic heterocyclic ring, Ay represents a hydrogen atom, an alkyl group having 1 to 12 carbon atoms which may have a substituent, or an organic group having 2 to 30 carbon atoms, which has at least one aromatic ring selected from the group consisting of an aromatic hydrocarbon ring and an aromatic heterocyclic ring, the aromatic rings in Ax and Ay may have a substituent, and Ax and Ay may be bonded to each other to form a ring, and $Q^3$ represents a hydrogen atom or an alkyl group having 1 to 6 carbon atoms which may have a substituent.

2. The polymerizable liquid crystal compound according to claim 1,
wherein in Formula (1), the ClogP value of the group represented by $L^2$-$SP^2$-$A^2$-$D^4$-$G^2$-$D^2$ is higher than the ClogP value of the group represented by $L^1$-$SP^1$-$A^1$-$D^3$-$G^1$-$D^1$.

3. The polymerizable liquid crystal compound according to claim 1,
wherein in Formulae (Ar-1) to (Ar-8), $Z^1$ represents a monovalent aliphatic hydrocarbon group having 3 to 20 carbon atoms.

4. The polymerizable liquid crystal compound according to claim 2,
wherein in Formulae (Ar-1) to (Ar-8), $Z^1$ represents a monovalent aliphatic hydrocarbon group having 3 to 20 carbon atoms.

5. A method for producing a polymerizable liquid crystal compound, used to synthesize the polymerizable liquid crystal compound according to claim 1, comprising:
a first esterification step of reacting a compound represented by Formula (2) with a compound represented by Formula (3) to produce a phenol compound; and
a second esterification step of reacting the phenol compound obtained in the first esterification step with a compound represented by Formula (4) to obtain the polymerizable liquid crystal compound according to claim 1, HO—Ar—OH  (2)

$L^1$-$SP^1$-$A^1$-$D^3$-$G^1$-COOH  (3)

$L^2$-$SP^2$-$A^2$-$D^4$-$G^2$-COOH  (4), in Formula (2), Ar represents any one aromatic ring selected from the group consisting of groups represented by Formulae (Ar-1) to (Ar-8), (Ar-1)
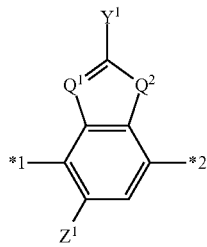

(Ar-2)
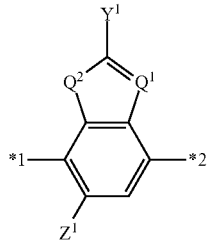

(Ar-3)
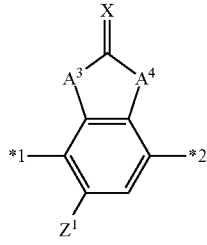

(Ar-4)
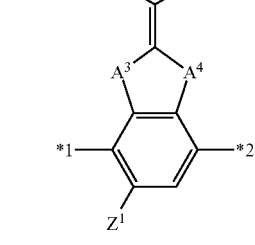

(Ar-5)
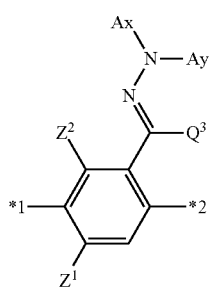

(Ar-6)
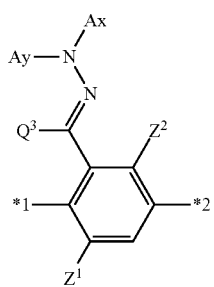

(Ar-7)
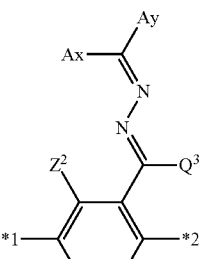

(Ar-8)
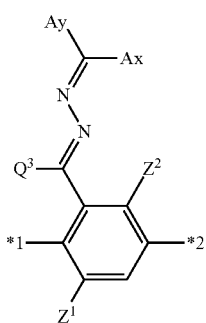

in Formulae (Ar-1) to (Ar-8), *1 and *2 each represent a bonding position with a hydroxyl group, $Q^1$ represents N or CH, $Q^2$ represents —S—, —O—, or —N($R^5$)—, and $R^5$ represents a hydrogen atom or an alkyl group having 1 to 6 carbon atoms, $Y^1$ represents an aromatic hydrocarbon group having 6 to 12 carbon atoms or an aromatic heterocyclic group having 3 to 12 carbon atoms, each of which may have a substituent, $Z^1$ represents a monovalent aliphatic hydrocarbon group having 3 to 20 carbon atoms, a monovalent aromatic hydrocarbon group having 6 to 20 carbon atoms, a halogen atom, —$OR^6$, —$NR^7R^8$, or —$SR^9$, and $R^6$ to $R^9$ each independently represent a monovalent aliphatic hydrocarbon group having 3 to 20 carbon atoms or a monovalent aromatic hydrocarbon group having 6 to 20 carbon atoms, $Z^2$ represents a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$OR^{10}$, —$NR^{11}R^{12}$, or —$SR^{13}$, and $R^{10}$ to $R^{13}$ each independently represent a hydrogen atom or an alkyl group having 1 to 6 carbon atoms, $A^3$ and $A^4$ each independently represent a group selected from the group consisting of —O—, —N($R^{14}$)—, —S—, and —CO—, and $R^{14}$ represents a hydrogen atom or a substituent, X represents a non-metal atom of Groups 14 to 16 to which a hydrogen atom or a substituent may be bonded, $D^5$ and $D^6$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $SP^3$ and $SP^4$ each independently represent a single bond, a linear or branched alkylene group having 1 to 12 carbon atoms, or a divalent linking group in which one or more of —$CH_2$-'s constituting the linear or branched alkylene group having 1 to 12 carbon atoms are substituted with —O—, —S—, —NH—, —N(Q)-, or —CO—, and Q represents a substituent, $L^3$ and $L^4$ each independently represent a monovalent organic group, and at least one of $L^3$, $L^4$, or $L^1$ or $L^2$ in Formula (1) represents a polymerizable group, Ax represents an organic group having 2 to 30 carbon atoms, which has at least one aromatic ring selected from the group consisting of an aromatic hydrocarbon ring and an aromatic heterocyclic ring, Ay represents a hydrogen atom, an alkyl group having 1 to 12 carbon atoms which may have a substituent, or an organic group having 2 to 30 carbon atoms, which has at least one aromatic ring selected from the group consisting of an aromatic hydrocarbon ring and an aromatic heterocyclic ring, the aromatic rings in Ax and Ay may have a substituent, and Ax and Ay may be bonded to each other to form a ring, $Q^3$ represents a hydrogen atom or an alkyl group having 1 to 6 carbon atoms which may have a substituent, in Formulae (3) and (4), $D^3$ and $D^4$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, and $R^1$, $R^2$, $R^3$, and $R^4$ each independently represent a hydrogen atom, a fluorine atom, or an alkyl group having 1 to 4 carbon atoms, $G^1$ and $G^2$ each independently represent a divalent alicyclic hydrocarbon group having 5 to 8 carbon atoms, which may have a substituent, and one or more of —$CH_2$-'s constituting the alicyclic hydrocarbon group may be substituted with —O—, —S—, or —NH—, $A^1$ and $A^2$ each independently represent an aromatic ring having 6 or more carbon atoms, which may have a substituent, or a cycloalkane ring having 6 or more carbon atoms, which may have a substituent, $SP^1$ and $SP^2$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent, and $L^1$ and $L^2$ each independently represent a monovalent organic group, and at least one of $L^1$ or $L^2$ represents a polymerizable group, provided that in a case where Ar in Formula (2) is an aromatic ring represented by Formula (Ar-4), at least one of $L^1$, $L^2$, or $L^3$ or $L^4$ in Formula (Ar-4) represents a polymerizable group.

6. A polymerizable liquid crystal composition comprising: the polymerizable liquid crystal compound according to claim 1.

7. A polymerizable liquid crystal composition comprising: the polymerizable liquid crystal compound according to claim 2.

8. A polymerizable liquid crystal composition comprising: the polymerizable liquid crystal compound according to claim 3.

9. The polymerizable liquid crystal composition according to claim 6, further comprising:
a polymerizable compound having two or more polymerizable groups, which is different from the polymerizable liquid crystal compound.

10. The polymerizable liquid crystal composition according to claim 7, further comprising:
a polymerizable compound having two or more polymerizable groups, which is different from the polymerizable liquid crystal compound.

11. The polymerizable liquid crystal composition according to claim 8, further comprising:
a polymerizable compound having two or more polymerizable groups, which is different from the polymerizable liquid crystal compound.

12. An optically anisotropic film obtained by polymerization of the polymerizable liquid crystal composition according to claim 6.

13. An optically anisotropic film obtained by polymerization of the polymerizable liquid crystal composition according to claim 9.

14. An optical film comprising:
the optically anisotropic film according to claim 12.

15. An optical film comprising:
the optically anisotropic film according to claim 13.

16. A polarizing plate comprising:
the optical film according to claim 14; and
a polarizer.

17. A polarizing plate comprising:
the optical film according to claim 15; and
a polarizer.

18. An image display device comprising:
the optical film according to claim 14.

19. An image display device comprising:
the optical film according to claim 15.

20. An image display device comprising:
the polarizing plate according to claim 16.

* * * * *